(12) United States Patent
Wischik et al.

(10) Patent No.: US 10,188,658 B2
(45) Date of Patent: *Jan. 29, 2019

(54) THERAPEUTIC USE OF DIAMINOPHENOTHIAZINES

(71) Applicant: WisTa Laboratories Ltd., Singapore (SG)

(72) Inventors: Claude Michel Wischik, Aberdeen (GB); Damon Jude Wischik, London (GB); John Mervyn David Storey, Old Aberdeen (GB); Charles Robert Harrington, Aberdeen (GB)

(73) Assignee: WisTa Laboratories Ltd., Singapore (SG)

( * ) Notice: Subject to any disclaimer, the term of this patent is extended or adjusted under 35 U.S.C. 154(b) by 238 days.

This patent is subject to a terminal disclaimer.

(21) Appl. No.: 14/866,035

(22) Filed: Sep. 25, 2015

(65) Prior Publication Data

US 2016/0030444 A1    Feb. 4, 2016

Related U.S. Application Data

(62) Division of application No. 12/681,511, filed as application No. PCT/GB2008/003315 on Oct. 1, 2008, now Pat. No. 9,149,481.

(60) Provisional application No. 60/960,544, filed on Oct. 3, 2007.

(51) Int. Cl.
| | |
|---|---|
| A61K 51/00 | (2006.01) |
| A61M 36/14 | (2006.01) |
| A61K 31/5415 | (2006.01) |
| A61K 31/542 | (2006.01) |
| A61K 9/00 | (2006.01) |
| A61K 45/06 | (2006.01) |

(52) U.S. Cl.
CPC ........ *A61K 31/5415* (2013.01); *A61K 9/0065* (2013.01); *A61K 31/542* (2013.01); *A61K 45/06* (2013.01)

(58) Field of Classification Search
CPC .............. A61K 31/5415; A61K 31/542; A61K 9/0065; A61K 45/06
USPC ....................................................... 424/1.65
See application file for complete search history.

(56) References Cited

U.S. PATENT DOCUMENTS

| | | | | |
|---|---|---|---|---|
| 5,972,389 A | * | 10/1999 | Shell et al. | 424/501 |
| 7,888,350 B2 | * | 2/2011 | Wischik et al. | 514/226.2 |
| 8,710,051 B2 | * | 4/2014 | Wischik et al. | 514/226.2 |
| 9,149,481 B2 | * | 10/2015 | Wischik et al. | |
| 9,211,294 B2 | * | 12/2015 | Wischik et al. | |
| 2003/0181389 A1 | | 9/2003 | Wulfert et al. | |
| 2004/0110250 A1 | | 6/2004 | Wischik et al. | |
| 2005/0136110 A1 | * | 6/2005 | Bartholomaeus | A61K 31/13 424/468 |
| 2006/0014216 A1 | | 1/2006 | Wischik et al. | |
| 2006/0287523 A1 | | 12/2006 | Wischik et al. | |
| 2007/0116757 A1 | | 5/2007 | Rariy et al. | |
| 2009/0054419 A1 | * | 2/2009 | Wischik et al. | 514/226.2 |
| 2011/0118242 A1 | * | 5/2011 | Wischik et al. | 514/226.2 |

FOREIGN PATENT DOCUMENTS

| | | |
|---|---|---|
| WO | WO 9206680 A1 * | 4/1992 |
| WO | WO-02/055720 A2 | 7/2002 |
| WO | WO 2007056439 A1 * | 5/2007 |
| WO | WO-2007/110627 A2 | 10/2007 |
| WO | WO-2008/007074 A2 | 1/2008 |

OTHER PUBLICATIONS

Berge et al. J., Pharm. Sci. 1977, 66, 1-19.*
International Search Report of the corresponding application PCT/GB2008/003315, dated Jan. 22, 2009.
Notification Concerning Transmittal of International Preliminary Report on Patentability (IPRP) (Chapter 1 of the Patent Cooperation Treaty) received in the corresponding application PCT/GB2008/003315, dated Apr. 7, 2010. (8 pgs.).
H.D.K. Drew et al., Derivatives of Methylene-blue, Journal of the Chemical Society (1933) pp. 248-253.
M. Contineanu, et al., Radiochem.Radioanal.Letters, 57/ 1/ 9-22 / 1983, pp. 9-22.

* cited by examiner

*Primary Examiner* — Michael G. Hartley
*Assistant Examiner* — Sean R Donohue
(74) *Attorney, Agent, or Firm* — Foley & Lardner LLP; Benjamin Berkowitz

(57) ABSTRACT

Described are methods and materials for use in the treatment or prophylaxis of diseases, for example cognitive disorders, using diaminophenothiazines. In particular it relates to treatments having optimized pharmacokinetic properties, and dosage forms are intended to improve the relative cognitive or CNS benefits of the diaminophenothiazines, for instance compared to haematological effects.

29 Claims, 43 Drawing Sheets

Fig. 37
Fig.37A
Fig.37B
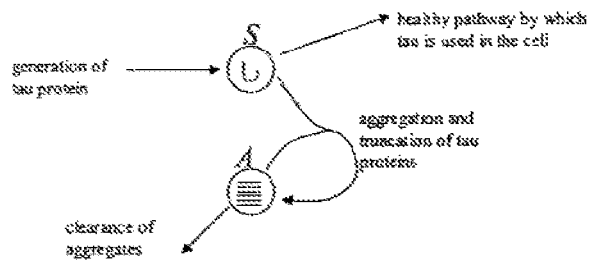
Fig.37C
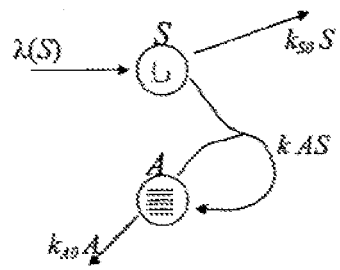
Fig.37D

Fig. 37 (continued)
Fig. 37E
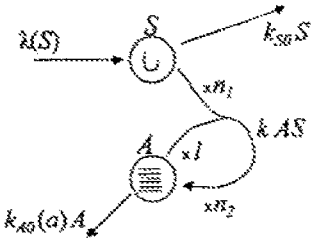
Fig. 37F
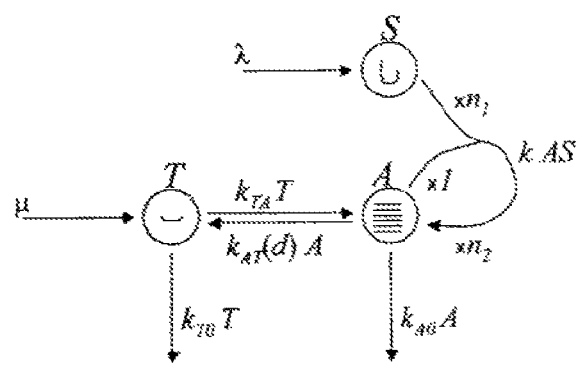
Fig. 37G
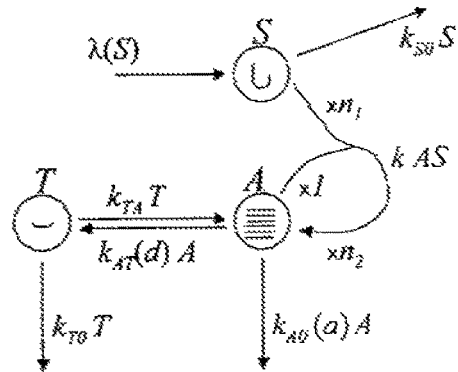

Fig. 37 (continued)
Fig. 37H
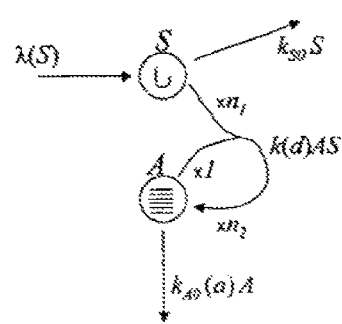
Fig. 37I
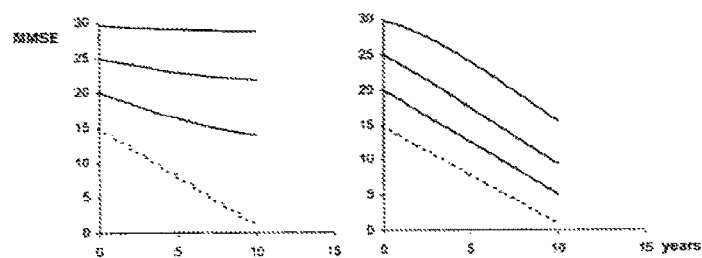

THERAPEUTIC USE OF DIAMINOPHENOTHIAZINES

CROSS-REFERENCE TO RELATED PATENT APPLICATIONS

This application is a Divisional of U.S. application Ser. No. 12/681,511, to issue on Oct. 6, 2015 as U.S. Pat. No. 9,149,481; which is the U.S. National Stage of PCT/GB2008/003315, filed Oct. 1, 2008; which claims priority to the filing date of Provisional Application U.S. Application 60/960,544, filed Oct. 3, 2007. The foregoing are incorporated herein by reference in their entirety.

TECHNICAL FIELD

The present invention relates generally to methods and materials for use in the treatment or prophylaxis of diseases, for example cognitive disorders, using diaminophenothiazines. In particular it relates to treatments having optimised pharmacokinetic properties.

BACKGROUND 3,7-diaminophenothiazine (DAPTZ) compounds have previously been shown to inhibit tau protein aggregation and to disrupt the structure of PHFs, and reverse the proteolytic stability of the PHF core (see WO96/30766, F Hoffman-La Roche). Such compounds were disclosed for use in the treatment and prophylaxis of various diseases, including AD and Lewy Body Disease, and included methylthioninium chloride ("MTC").

WO96/30766 describes, in the case of oral administration, a daily dosage of about 50 mg to about 700 mg, preferably about 150 mg to about 300 mg, divided in preferably 1-3 unit doses.

Other disclosures of phenothiazines in the area of neurodegenerative disorders include WO 02/075318, WO 2005/030676.

It was known in the art that DAPTZ compounds can occur in a charged (oxidised) form and an uncharged (reduced or "leuko") form. It was also known that the cellular absorption of these differed. Additionally, it was known that such compounds could in principle have adverse haematological effects and other side effects at certain doses.

WO 02/055720 (The University Court of the University of Aberdeen) discusses the use of reduced forms of diaminophenothiazines specifically for the treatment of a variety of protein aggregating diseases, although the disclosure is primarily concerned with tauopathies. WO 02/055720 discusses a preliminary pharmacokinetic model based on studies of urinary excretion data sets in humans, dogs and rats by DiSanto and Wagner, J Pharm Sci 1972, 61:1086-1090 and 1972, 61:1090-1094 and Moody et al., Biol Psych 1989, 26: 847-858. It further notes that the only form of methylene blue which crosses the blood-brain barrier after iv administration is the reduced form. Based on in vitro activity for the reduced forms of diaminophenothiazines therein, a suggested daily dosage was 3.2-3.5 mg/kg, and dosages of 20 mg tds, 50 mg tds or 100 mg tds, combined with 2× mg ratio of ascorbic acid in such a manner as to achieve more than 90% reduction prior to ingestion were also described.

However WO 02/055720 did not provide a model which integrated blood level data such as that described by Peter et al. (2000) Eur J Clin Pharmacol 56: 247-250 or provide a model validated by clinical trial data. Indeed, as described below, the Peter et al. data contradicted the earlier data from DiSanto and Wagner as regards terminal elimination half-life.

May et al. (Am J Physiol Cell Physiol, 2004, Vol. 286, pp. C1390-C1398) showed that human erythrocytes sequentially reduce and take up MTC i.e. that MTC itself is not taken up by the cells but rather that it is the reduced from of MTC that crosses the cell membrane. They also showed that the rate of uptake is enzyme dependent; and that both MTC and reduced MTC are concentrated in cells (reduced MTC re-equilibrates once inside the cell to form MTC).

Nevertheless, the optimisation of an appropriate therapeutic dose of DAPTZ compounds such as MTC, and their formulation, in particular to optimise desired activity or minimise adverse side affects are complex problems. A major barrier to this is the lack of a suitable pharmacokinetic model. Thus it can be seen that the provision of such a model, and hence teaching about addressing one or more of these problems, would provide a contribution to the art.

Prior filed, unpublished, application PCT/GB2007/001103 discloses compounds including:

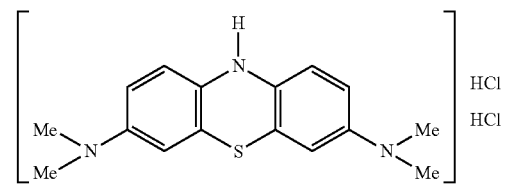

These compounds may be considered to be a stabilized reduced form by comparison with, for example, MTC.

PCT/GB2007/001103 describes dosage units comprising 20 to 300 mg of the DAPTZ compounds described therein e.g. 30 to 200 mg, for example 30 mg, 60 mg, 100 mg, 150 mg, 200 mg. A suitable dose of the DAPTZ compound is suggested in the range of about 100 ng to about 25 mg (more typically about 1 µg to about 10 mg) per kilogram body weight of the subject per day e.g. 100 mg, 3 times daily, 150 mg, 2 times daily, 200 mg, 2 times daily.

DISCLOSURE OF THE INVENTION

Methylthioninium chloride ("MTC") is the active ingredient of a proprietary therapeutic preparation (designated "REMBER™") being developed for the treatment of AD and related dementias. A clinical trial has been conducted in which therapeutic efficacy has been demonstrated over 50 weeks of treatment in mild and moderate AD.

Utilising the results of this trial, the present inventors have developed a completely novel integrated pharmacokinetic model applicable to the human oral dosage of DAPTZ compounds including, but not limited to, MTC. The model has major implications for defining the parameters that determine optimal oral dosing in terms of safety and efficacy, and implies novel treatment modalities for the treatment of cognitive disorders. The new model is shown to be accurate in that it predicts urinary excretion, and correctly predicts kinetics of the brain tissue compartment verified by the pig study.

Briefly, the clinical trial showed that MTC has two systemic pharmacological actions: cognitive effects and haematological effects, but that unexpectedly these actions are separable. Specifically the cognitive effects do not show a monotonic dose-response relationship, whereas the haematological effects do. The inventors propose that two distinct species are responsible for the two types of pharmacological activity: MTC absorbed as the uncharged Leuco-MT form being responsible for the beneficial cognitive activity, and MTC absorbed as an oxidised dimeric species being responsible for the oxidation of haemoglobin. Since these effects are mechanistically distinct, they may be separately manipulated such as to maximising the bioavailability of the therapeutically active (cognitively effective) species.

Thus these findings have profound implications for the dosing of both oxidised and leuco-DAPTZ compounds, in each case such as to maximise therapeutic activity and therefore reducing side effects by optimisation of dosing regime and formulation relevant to the agent in question.

Oxidised DAPTZ Compounds—Rapid Dissolution Forms

As can be seen from FIG. 31A, there is a steep loss of predicted efficacy as the observed percentage capsule dissolution at 30 minutes drops below 20%. This confirms that rapid dissolution is critical for therapeutic activity and can be explained by the critical role of the stomach in the absorption of the Methylthioninium (MT)-moiety in its therapeutically active form.

Specifically, according to the delayed dissolution hypothesis, a quite distinct form of MT is responsible for haematological side effects. This was postulated to be a dimer, the formation of which is favoured in the alkaline conditions of the small intestine and lower gut. Therefore, the haematological side effects observed in the clinical trial were a specific consequence of the gelatine capsule formulation used in the study (and in particular its rate of dissolution—see FIG. 7) rather than an inherent feature of the MT moiety itself, if absorbed via the stomach.

Therefore, in the design of an improved formulation of MTC or other DAPTZ compounds, the attainment of predicted efficacy is critically determined by the requirement that the dissolution of the investigational medicinal product (i.e. tablet or capsule) be greater than 50% in 30 minutes in standard conditions.

Thus in one aspect there is disclosed a method of treatment of a cognitive or CNS disorder in a patient, wherein said disorder is one which is susceptible to treatment by a DAPTZ compound, which method comprises orally administering to said patient a dosage unit containing said DAPTZ compound in oxidised form as active ingredient, wherein said dosage unit releases at least 50% of said active ingredient within 30 minutes under standard conditions.

The treatment of the cognitive or CNS disorder will be such as to maximise the relative cognitive or CNS benefit vs. haematological effects of the DAPTZ compound (see e.g. FIG. 7).

Capsule dissolution is determined by the amount of DAPTZ released into the aqueous phase of simulated gastric fluid (SGF) under standard US/EU Pharmacopoeia dissolution conditions. This is described in Example 11.

Dosage units of this form will therefore maximise absorption in the stomach, and more critically minimise formation of dimers which is favoured in the alkaline conditions of the small intestine and lower gut.

Preferably greater than 95%, 90%, 85%, 80%, 75%, 70%, 60% or 50% will be absorbed by the stomach in less than 30 minutes.

Formulations and delivery vehicles suitable for this rapid dissolution are discussed in more detail below.

The amount of oxidised DAPTZ in the dosage form will be a therapeutically-effective amount. However based on the disclosure herein it can be seen that very high doses (where dissolution is delayed) will lead to only limited absorption of the nominal dose in the stomach via the reductase mechanism leading to undesirable delayed absorption from the small intestine at higher pH via formation of dimers.

Thus preferably the dosage unit comprises less than 120 mg, less than 100, less than 70, most preferably from 40-70 mg (e.g. 40, 45, 50, 55, 60, 65, or 70) and is administered 3/day or 4/day (see e.g. FIGS. 29 & 30 & 32 & 36).

Oxidised DAPTZ Compounds—Gastric Retention Forms

Thus in one aspect there is disclosed a method of treatment of a cognitive or CNS disorder in a patient, wherein said disorder is one which is susceptible to treatment by a DAPTZ compound, which method comprises orally administering to said patient a dosage unit containing said DAPTZ compound in oxidised form as active ingredient, wherein said dosage unit is gastroretained.

The treatment of the cognitive or CNS disorder will be such as to maximise the relative cognitive or CNS benefit vs. haematological effects of the DAPTZ compound (see e.g. FIG. 7).

A gastroretained form will preferably be held in the stomach for at least 30 minutes, more preferably at least 1, 2, 3, 4, 5, 6, 8, 12 hours or more.

Formulations and delivery vehicles suitable for gastroretention are discussed in more detail below.

The amount of oxidised DAPTZ in the gastroretained dosage form will be a therapeutically-effective amount. By minimising transit to the small intestine (and hence formation of therapeutically inactive dimers) higher loadings of oxidised DAPTZ are feasible. Thus preferably the dosage unit comprises at least 50, 60, 70, 80, 90 or 100 mg, or more e.g. 200, 300, 400, 500 mg.

Reduced DAPTZ Compounds

The relationships described herein have implications as regards the conventional approach to achieving using a more convenient dosing regime, ie 2/day or 1/day. These dosing regimes are in principle more desirable in patients with dementia, who are forgetful and hence need prompting to take medication. The conventional approach to achieving a more convenient dosing regime is to create a slow-release formulation. However, the present analysis indicates that, on the contrary, a standard slow-release formulation of an oxidised DAPTZ form of a therapeutic product would essentially eliminate efficacy, as illustrated conveniently by the properties of the 100 mg capsule in TRx-014-001 in the Examples hereinafter.

Thus, for the reasons discussed above, it would not be feasible to generate a delayed-release formulation of an oxidised DAPTZ-based medicinal product. However, this would not be the case for drug products where the DAPTZ compound is in reduced form. This is because the leuco-forms of such compounds cannot dimerise, since they are not 'flat' molecule do not have the charge which permits stabilisation of the dimeric form by charge neutralisation.

Thus in a further aspect there is disclosed a method of treatment of a cognitive or CNS disorder in a patient, wherein said disorder is one which is susceptible to treatment by a DAPTZ compound, which method comprises orally administering to said patient a dosage unit containing said DAPTZ compound in stable crystalline reduced form as active ingredient.

As described below preferably the compound is such as to treat the cognitive or CNS disorder and to maximise the relative cognitive or CNS benefits vs. haematological effects of the DAPTZ compound.

In particular, based on the teaching herein, loss due to initial non-absorption from the stomach would be greatly reduced since the stably reduced crystalline forms have greater solubility than the oxidised equivalents and would not require the activity of the thiazine-dye reductase (May et al., 2004) which is presumed to exist in the stomach and is presumed to be necessary for absorption (see predicted absorption in FIG. 33).

It is therefore inferred that substantially higher efficacy and superior dosing regime could be achieved using the L-MTx form of the methylthioninium moiety. The amount of reduced DAPTZ in the dosage form will be a therapeutically-effective amount.

In particular a delayed-release formulation (e.g. 1/day) of the reduced DAPTZ compound at between 100-1000 mg would in principle not lead to the adverse consequences of delayed absorption (see FIG. 38). Thus in the light of the disclosure herein dosages of up to 1000 mg or more (e.g. 100, 200, 300, 400, 500, 600, 700, 800, 900 or 1000 mg) given 1/day or more may be considered.

Preferably this is a slow or delayed release formulation i.e. release of less than <50% in 1 hour, 2 hours, 3 hours, 4 hours, 5 hours, 6 hours, 7 hours, 8 hours.

As can be seen from FIGS. 34 & 35, it is predicted that a level of efficacy of −8.1 ADAS-cog units could be achieved on a dosing regime of 100 mg of the reduced DAPTZ (described as "L-MTx form") administered twice daily. This could also be achieved by dosing with 60 mg 3 times per day. Even higher efficacy levels would be expected using 100 mg or higher administered 3 times per day.

The preferred reduced DAPTZ compounds of the present invention may conveniently be described as being in a "stabilized crystalline reduced form" and are described in prior filed, unpublished, application PCT/GB2007/001103. It will appreciated, however, that even these compounds may autoxidize to some extent to give the corresponding oxidized forms. Thus, it is likely, if not inevitable, that compositions comprising the stabilized crystalline reduced form DAPTZ compounds of the present invention will contain, as an impurity, as least some of the corresponding oxidized compound.

In aspects of the present invention pertaining to these stabilized crystalline reduced form DAPTZ compounds, these oxidised DAPTZ compounds may represent no more than 50% by weight, e.g., no more than 40% by weight, e.g., no more than 30% by weight, preferably e.g., no more than 20% by weight, e.g., no more than 10% by weight, e.g., no more than 5% by weight, e.g., no more than 3% by weight, e.g., no more than 2% by weight, e.g., no more than 1% by weight of the total DAPTZ content of the dosage form.

Treatment

The term "treatment," as used herein in the context of treating a condition, pertains generally to treatment and therapy of a human, in which some desired therapeutic effect is achieved, for example, the inhibition of the progress of the condition, and includes a reduction in the rate of progress, a halt in the rate of progress, regression of the condition, amelioration of the condition, and cure of the condition.

The present invention further includes prophylactic measures (i.e., prophylaxis, prevention).

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Combination treatments are discussed in more detail hereinafter.

Cognitive or CNS Disorders

Preferred cognitive or CNS disorders are described below. Further neurodegenerative disorders are described in the Examples hereinafter.

The cognitive disorder may be a tauopathy condition in a patient (see e.g. WO96/30766). As well as Alzheimer's disease (AD), the pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Other dementias include fronto-temporal dementia (FTD); parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD) and others (see Wischik et al. 2000, loc. cit, for detailed discussion—especially Table 5.1). All of these diseases, which are characterized primarily or partially by abnormal tau aggregation, are referred to herein as "tauopathies".

In this and all other aspects of the invention relating to tauopathies, preferably the tauopathy is selected from the list consisting of the indications above, i.e., AD, Pick's disease, PSP, FTD, FTDP-17, DDPAC, PPND, Guam-ALS syndrome, PNLD, and CBD.

In one preferred embodiment the tauopathy is Alzheimer's disease (AD).

Where the disease is any tauopathy, the method of treatment of the tauopathy may be such that the DAPTZ compound causes inhibition of the aggregation of the tau protein associated with said disease state and also dissolution of tau aggregates in the brain of the patient or subject. As described in the Examples below, the present inventors have shown that dissolution of such aggregates is key effect in opening a clearance pathway (see e.g. FIGS. 6A and 6B).

In one embodiment the cognitive disorder may be mild cognitive impairment (MCI) e.g. amnestic MCI. Prior filed U.S. provisional application 60/945,006 (herein specifically incorporated by reference) describes the use of DAPTZ compounds for MCI. While there is still discussion in the literature as to the nature of the MCI concept (see Gauthier et al., Lancet, 2006; 367: 1262-1270; Petersen R C et al. Neuropathological features of amnestic mild cognitive impairment. Arch Neurol 2006; 63: 665-672) MCI is recognised as a valid disease target by the FDA. It is defined by having a minor degree of cognitive impairment not yet meeting clinical criteria for a diagnosis of dementia.

In one embodiment the CNS disorder may be a synucleinopathy such as Parkinson's Disease (PD).

Prior filed PCT application PCT/GB2007/001105 (herein specifically incorporated by reference) describes the use of DAPTZ compounds for the treatment of PD and other synucleinopathies.

The synucleinopathies currently consist of the following disorders: PD, dementia with Lewy bodies (DLB), multiple system atrophy (MSA), drug-induced parkinsonism (e.g.

produced by 1-methyl-4-phenyl-1,2,3,6-tetrahydropyridine [MPTP] or pesticides such as rotenone), and pure autonomic failure (PAF).

Patient Groups

Suitable subjects for the method may be selected on the basis of conventional factors.

Thus, for example, for AD the initial selection of a patient may involve any one or more of: rigorous evaluation by experienced clinician; exclusion of non-AD diagnosis as far as possible by supplementary laboratory and other investigations; objective evaluation of level of cognitive function using neuropathologically validated battery.

For MCI, representative criteria for syndromal MCI include features: A. The patient is neither normal nor demented; B. There is evidence of cognitive deterioration shown by either objectively measured decline over time and/or subjective report of decline by self and/or informant in conjunction with objective cognitive tests (e.g. secondary tests if memory); C. Activities of daily living are preserved and complex instrumental functions are either intact or minimally impaired (see also Winblad, B. et al. (2004) Mild cognitive impairment—beyond controversies, towards a consensus: report of the International Working Group on Mild Cognitive Impairment. J. Intern. Med. 256: 240-246). The patient will generally be one diagnosed with MCI, but be one not diagnosed with AD (i.e. will not show dementia). The patient may, for example, be aged over 45, 50, 55 years. The patient may be one meeting one or all of the following criteria in respect of: (i) Braak stage 3 or less, 2 or less, 1 or less; (ii) MMSE score less than or equal to MMSE 24, 25, 26, 27, 28 or 29, more preferably less than or equal to MMSE 24, 25, 26, most preferably less than or equal to MMSE 24 or 25.

Diagnosis of PD is well known to those skilled in the art.

As noted above, the methods of the present invention are intended to treat a cognitive or CNS disorder in a patient such as to maximise the relative cognitive or CNS benefit vs. haematological effects of the DAPTZ compound.

In various aspects of the invention the patient may be one whom is believed to be at above average risk of a haematological disorder, the effects of which may otherwise be exacerbated by the DAPTZ compound. Thus (without limitation) the patient may be one known or believed to be suffering from a haemoglobinopathy such as Sickle-cell disease, Thalassemia, Methaemoglobinemia; an anemia (e.g. a haemolytic anemia); a haematological malignancy (e.g. lymphoma, myeloma, plasmacytoma or leukemia); a coagulopathy such as hemophilia; and so on. Above average risk of such diseases may be assessed using conventional criteria e.g. symptomatic, genetic, age, lifestyle, ethnicity (for example Sickle-cell disease occurs more commonly in people—or their descendants—from parts of the world such as sub-Saharan Africa). A particular class of patient at risk of a haematological disorder would be those aged over 70 years old, who may be subject to age-related anemic conditions (e.g. myeloid dysplasia).

Dosage, Formulations and Delivery Vehicles

Within the disclosure herein, the precise selected dosage level will depend on a variety of factors including, but not limited to, the activity of the particular DAPTZ compound, the duration of the treatment, other drugs, compounds, and/or materials used in combination, the severity of the condition, and the species, sex, age, weight, condition, general health, and prior medical history of the patient.

Drug or dosage units (e.g., a pharmaceutical tablet or capsule) with the appropriate loading, dissolution, or gastroretention properties described above can be provided by those skilled in the art based on the disclosure herein using conventional technologies, and those conventional technologies do not per se form part of the present invention.

For example rapid dissolution drug units (for oxidised or reduced DAPTZ compounds) or slow or delayed release dissolution units (for reduced DAPTZ compounds) can be provided and tested to order from commercial sources e.g. Encap Drug Delivery (Units 4, 5 & 6, Oakbank Park Way, Livingston, West Lothian, EH53 0TH, Scotland, UK); Eurand (Via Martin Luther King, 13 20060, Pessano con Bornago, Milan) and so on.

Gastro-retained drug units are also widely known in the patent literature (e.g. U.S. Pat. No. 6,207,197, U.S. Pat. No. 5,972,389) and general literature, and have been for many years—see e.g. Davis, et al., "Transit of pharmaceutical dosage forms through the small intestine", Gut, 27 (8):886-892 (1986); Fara, "Physiological limitations: gastric emptying and transit of dosage forms" in: Rate Control in Drug Therapy, L. F. Prescott, et al., Eds., Churchill Livingstone, N.Y. (1985); Davis, S. S. (2005) Formulation strategies for absorption windows Drug Discovery Today 10:249-257. This latter notes that the process of GI transit in humans and its implications for drug delivery are now well understood. Dosage forms administered to a fed stomach will have delayed emptying. A multiparticulate system, such as one containing microspheres or pellets, can become mixed with the food and, as a consequence, will usually empty with the food over an extended period of time. If the administered particles are large, they will not be able to pass through the constricted pylorus with the digested food, and will have to wait until the stomach is empty and in the fasted state. In general, particles up to 10 mm in size can be expected to empty from the fed stomach. Exactly when the particles empty will also depend on their number and their relative positions within the stomach. Hence, a dosage form larger than 15-20 mm and administered with food is expected to achieve gastroretention. Such a dosage form will then have an opportunity to empty after the food has left the stomach when the fasted state occurs.

A single unit system (or a multiparticulate) can empty rapidly from the fasted stomach. Exactly when it will empty will also depend on the timing of the housekeeper wave in relation to dosing. The open pylorus has a diameter of 15 mm in humans. An object greater than this size will have difficulty in passing into the small intestine in the fasted (or fed) state. Based on this knowledge, various approaches have been devised for gastroretention. These fall into two main classes: (i) small particles that have bioadhesive properties (and also a propensity to float on the stomach contents); and (ii) large swelling objects that will be retained in the stomach because of their size. These swelling systems might also have floating characteristics, usually provided by the generation of carbon dioxide.

The drug delivery company Depomed have described gastroretentive tablets 'that swell in the stomach which treats the tablet like undigested food, and won't let it pass into the small intestine. The tablet is retained by the stomach for several hours, where it can deliver its payload of drug as quickly or slowly as desired' (www[dot]depomedinc[dot]com/products_pipeline.htm).

These systems are based on polyethylene oxide (PEO) in combination with hydroxypropyl methylcellulose (HPMC) to produce a sustained-release matrix tablet that can swell. According to the company, candidate molecules include metformin, gabapentin ciprofloxacin and furosemide. Recent press releases state that Depomed has completed Phase III clinical trials with once-daily metformin for the treatment of Type II diabetes and with once-daily ciprofloxacin for the treatment of urinary tract infections, and that new drug applications (NDA) for both products have been filed with the FDA. The company is also conducting a Phase II trial with the diuretic furosemide.

A recent abstract has described a dual-labelled scintigraphic study of controlled release furosemide gastric retentive tablets in healthy volunteers. The dual-labelling procedure permitted separate characterization of the erosion and swelling. The tablets (and an immediate release control) were administered after a high-fat breakfast. Gastric residence of the swelling tablets was sufficiently long to deliver the drug to the upper GI tract. Consequently, the plasma concentration of the drug was extended and, furthermore, unlike previous slow release formulations reported in the literature, there was no reduction in bioavailability. From a standpoint of patient compliance, the gastroretentive tablet provided gradual diuresis and natriuresis, rather than the brief and intense diuresis of short onset time experienced by patients taking conventional immediate release furosemide tablets.

Thus known gastroretained dosage forms may be applicable to the present invention, and in particular for use with oxidised DAPTZ forms.

While it is possible for the diaminophenothiazinium compound to be used (e.g., administered) alone, it is often preferable to present it as a composition or formulation.

Preferably the drug or dosage unit is provided as a pharmaceutical composition (e.g., formulation, preparation, medicament) comprising the DAPTZ compound, as described herein, and a pharmaceutically acceptable carrier, diluent, or excipient.

In one embodiment, the composition is a pharmaceutical composition comprising at least one diaminophenothiazinium compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, N.Y., USA), Remington's Pharmaceutical Sciences, 20th edition, pub. Lippincott, Williams & Wilkins, 2000; and Handbook of Pharmaceutical Excipients, 2nd edition, 1994.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients.

In general, the formulations are prepared by uniformly and intimately bringing into association the active compound with carriers (e.g., liquid carriers, finely divided solid carrier, etc.), and then shaping the product, if necessary.

As noted above, the formulation may be prepared to provide for rapid or slow release; immediate, delayed, timed, or sustained release; or a combination thereof.

Combination Therapies

Combination treatments and therapies, in which two or more treatments or therapies are combined, for example, sequentially or simultaneously, are discussed in more detail hereinafter. Thus it will be understood that any of the medical uses or methods described herein may be used in a combination therapy e.g. another treatment for AD, MCI, or PD respectively. For example a treatment of the invention for AD (e.g., employing a compound of the invention) is in combination with a cholinesterase inhibitor such as Donepezil (Aricept™), Rivastigmine (Exelon™) or Galantamine (Reminyl™).

In one embodiment, a treatment of the invention (e.g., employing a compound of the invention) is in combination with an NMDA receptor antagonist such as Memantine (Ebixa™, Namenda™).

In one embodiment, a treatment of the invention (e.g. employing a compound of the invention) is in combination with a muscarinic receptor agonist.

In one embodiment, a treatment of the invention (e.g. employing a compound of the invention) is in combination with an inhibitor of amyloid precursor protein to beta-amyloid (e.g., an inhibitor of amyloid precursor protein processing that leads to enhanced generation of beta-amyloid).

Example DAPTZ Compounds

The relationship between oxidised and reduced DAPTZ compounds can be conveniently illustrated using MTC, a phenothiazin-5-ium salt. This may conveniently be considered to be an "oxidized form" when considered in respect of the corresponding 10H-phenothiazine compound, N,N,N', N'-tetramethyl-10H-phenothiazine-3,7-diamine, which may conveniently be considered to be a "reduced form":

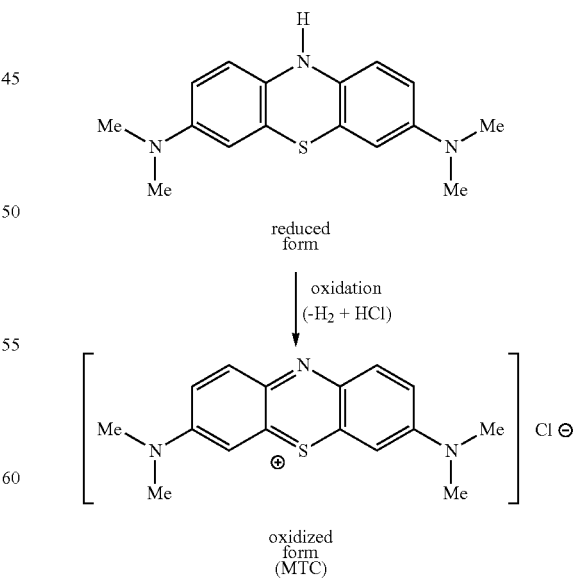

This aspect of the invention pertains to certain diaminophenothiazine compounds and analogs thereof, having one of the following formulae, and pharmaceutically acceptable salts, hydrates, and solvates thereof (collectively referred to herein as "diaminophenothiazines" or "diaminophenothiazine compounds"):

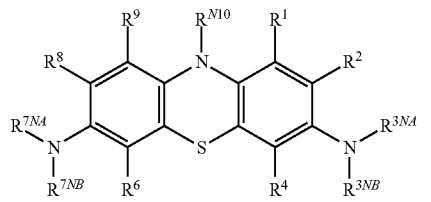
(1)

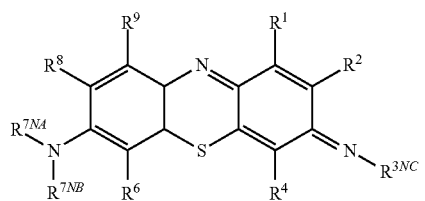
(2)

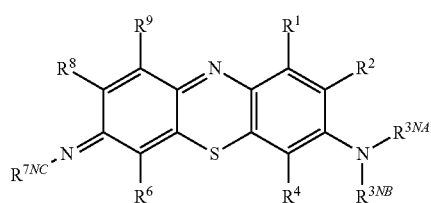
(3)

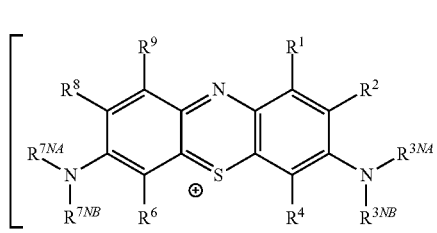
(4)

Formula (1) depicts compounds in a reduced form, whereas each of Formulae (2), (3), and (4) depicts compounds in an oxidized form.

In one embodiment, the compounds are selected from compounds of formula (1), and pharmaceutically acceptable salts, hydrates, and solvates thereof.

In one embodiment, the compounds are selected from compounds of formula (2) or (3), and pharmaceutically acceptable salts, hydrates, and solvates thereof.

In one embodiment, the compounds are selected from compounds of formula (4), and pharmaceutically acceptable salts, hydrates, and solvates thereof.

Each one of the above structures is only one of many equivalent resonance structures, and all of which are intended to be encompassed by that representative structure. For example, structure (4) is only one of many equivalent resonance structures, some of which are shown below, and all of which are intended to be encompassed by structure (4):

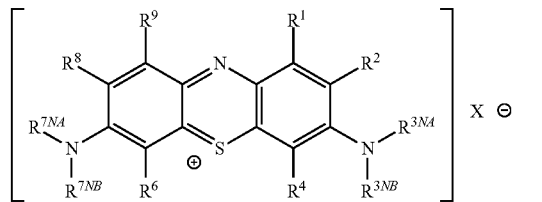
(4-B)

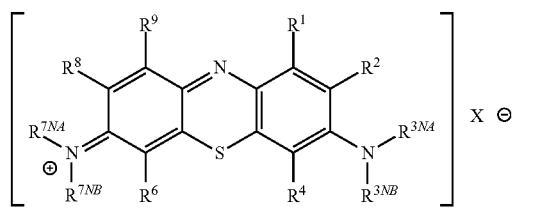
(4-C)

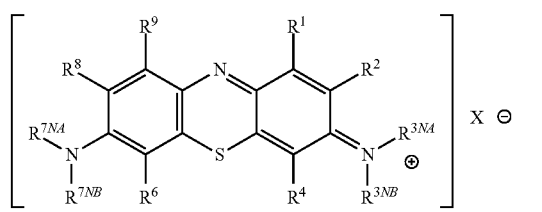
(4-D)

Carbon Ring Atom Substituents

In each one of the above formulae, each one of $R^1$, $R^2$, $R^4$, $R^6$, $R^8$, and $R^9$ is independently selected from:
—H;
—F; —Cl; —Br; —I;
—OH; —OR;
—SH; —SR;
—NO$_2$;
—C(=O)R;
—C(=O)OH; —C(=O)OR;
—C(=O)NH$_2$; —C(=O)NHR; —C(=O)NR$_2$;
—C(=O)NR$^{N1}$R$^{N2}$;
—NH$_2$; —NHR; —NR$_2$; —NR$^{N1}$R$^{N2}$;
—NHC(=O)H; —NRC(=O)H; —NHC(=O)R; —NRC(=O)R;
—R;
wherein each R is independently selected from:
 unsubstituted aliphatic $C_{1-6}$alkyl; substituted aliphatic $C_{1-6}$alkyl;
 unsubstituted aliphatic $C_{2-6}$alkenyl; substituted aliphatic $C_{2-6}$alkenyl;
 unsubstituted $C_{3-6}$cycloalkyl; substituted $C_{3-6}$cycloalkyl;
 unsubstituted $C_{6-10}$carboaryl; substituted $C_{6-10}$carboaryl;
 unsubstituted $C_{5-10}$heteroaryl; substituted $C_{5-10}$heteroaryl;
 unsubstituted $C_{6-10}$carboaryl-$C_{1-4}$alkyl; substituted $C_{6-10}$carboaryl-$C_{1-4}$alkyl;
wherein, in each group —NR$^{N1}$R$^{N2}$, independently, R$^{N1}$ and R$^{N2}$ taken together with the nitrogen atom to which they are attached form a ring having from 3 to 7 ring atoms.

Examples of groups —NR$^{N1}$R$^{N2}$, wherein R$^{N1}$ and R$^{N2}$ taken together with the nitrogen atom to which they are attached form a ring having from 3 to 7 ring atoms, include: pyrrolidino, piperidino, piperazino, morpholino, pyrrolyl, and substituted forms, such as N-substituted forms, such as N-methyl piperazino.

In one embodiment, each one of $R^1$, $R^2$, $R^4$, $R^6$, $R^8$, and $R^9$ is independently selected from:
- —H;
- —F; —Cl; —Br; —I;
- —OH; —OR;
- —C(=O)OH; —C(=O)OR;
- —R.

In one embodiment, each one of $R^1$, $R^2$, $R^4$, $R^6$, $R^8$, and $R^9$ is independently selected from:
- —H;
- —R.

In one embodiment, each R is independently selected from:
- unsubstituted aliphatic $C_{1-6}$alkyl; substituted aliphatic $C_{1-6}$alkyl;
- unsubstituted aliphatic $C_{2-6}$alkenyl; substituted aliphatic $C_{2-6}$alkenyl;
- unsubstituted $C_{3-6}$cycloalkyl; substituted $C_{3-6}$cycloalkyl.

In one embodiment, each R is independently selected from:
- unsubstituted aliphatic $C_{1-6}$alkyl; substituted aliphatic $C_{1-6}$alkyl.

In one embodiment, each R is independently selected from: -Me, -Et, -nPr, and -iPr.

In one embodiment, each R is independently selected from: -Me and -Et.

In one embodiment, the $C_{1-6}$alkyl group is a $C_{1-4}$alkyl group.

In one embodiment, the $C_{2-6}$alkenyl group is a $C_{2-4}$alkenyl group.

In one embodiment, the $C_{3-6}$cycloalkyl group is a $C_{3-4}$cycloalkyl group.

Examples of unsubstituted aliphatic $C_{1-6}$alkyl groups include: methyl, ethyl, n-propyl, iso-propyl, n-butyl, iso-butyl, sec-butyl, tert-butyl, n-pentyl, iso-pentyl, tert-pentyl, neo-pentyl, hexyl, iso-hexyl, etc.

Examples of unsubstituted aliphatic $C_{2-6}$alkenyl groups include: propen-1-yl, propen-2-yl, buten-1-yl, buten-2-yl, buten-3-yl, etc.

Examples of unsubstituted $C_{3-6}$cycloalkyl groups include: cyclopropyl, cyclopropyl-methyl, cyclobutyl, cyclopentyl, cyclohexyl, etc.

In one embodiment, the $C_{6-10}$carboaryl group is a $C_6$carboaryl group.

In one embodiment, the $C_{5-10}$heteroaryl group is a $C_{5-6}$heteroaryl group.

In one embodiment, the $C_{6-10}$carboaryl-$C_{1-4}$alkyl group is a $C_6$carboaryl-$C_{1-2}$alkyl group.

Examples of unsubstituted $C_{6-10}$carboaryl groups include: phenyl, naphthyl.

Examples of unsubstituted $C_{5-10}$heteroaryl groups include: pyrrolyl, thienyl, furyl, imidazolyl, oxazolyl, isoxazolyl, thiazolyl, isothiazolyl, pyrazolyl, pyridyl, pyrazinyl, pyrimidinyl, pyridazinyl.

Examples of unsubstituted $C_{6-10}$carboaryl-$C_{1-4}$alkyl groups include: benzyl, phenylethyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are independently selected from:
- —F; —Cl; —Br; —I;
- —OH; —OR';
- —SH; —SR';
- —NO$_2$;
- —C(=O)R';
- —C(=O)OH; —C(=O)OR';
- —C(=O)NH$_2$; —C(=O)NHR'; —C(=O)NR'$_2$; —C(=O)NR'$^{N1}$R'$^{N2}$;
- —NH$_2$; —NHR'; —NR'$_2$; —NR'$^{N1}$R'$^{N2}$;
- —NHC(=O)H; —N'RC(=O)H; —NHC(=O)'R; —N'RC(=O)'R;
- —R';

wherein each R' is independently selected from:
- unsubstituted aliphatic $C_{1-6}$alkyl; substituted aliphatic $C_{1-6}$alkyl;
- unsubstituted aliphatic $C_{2-6}$alkenyl; substituted aliphatic $C_{2-6}$alkenyl;
- unsubstituted $C_{3-6}$cycloalkyl; substituted $C_{3-6}$cycloalkyl;
- unsubstituted $C_{6-10}$carboaryl; substituted $C_{6-10}$carboaryl;
- unsubstituted $C_{5-10}$heteroaryl; substituted $C_{5-10}$heteroaryl;
- unsubstituted $C_{6-10}$carboaryl-$C_{1-4}$alkyl; substituted $C_{6-10}$carboaryl-$C_{1-4}$alkyl;

wherein, in each group —NR'$^{N1}$R'$^{N2}$, independently, R'$^{N1}$ and R'$^{N2}$ taken together with the nitrogen atom to which they are attached form a ring having from 3 to 7 ring atoms.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are independently selected from:
- —F; —Cl; —Br; —I;
- —OH; —OR;
- —C(=O)OH; —C(=O)OR';
- —R'.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from:
- unsubstituted aliphatic $C_{1-6}$alkyl;
- unsubstituted aliphatic $C_{2-6}$alkenyl;
- unsubstituted $C_{3-6}$cycloalkyl;
- unsubstituted $C_{6-10}$carboaryl;
- unsubstituted $C_{5-10}$heteroaryl;
- unsubstituted $C_{6-10}$carboaryl-$C_{1-4}$alkyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from:
- unsubstituted aliphatic $C_{1-6}$alkyl;
- unsubstituted aliphatic $C_{2-6}$alkenyl;
- unsubstituted $C_{3-6}$cycloalkyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from:
- unsubstituted aliphatic $C_{1-6}$alkyl; substituted aliphatic $C_{1-6}$alkyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from: -Me, -Et, -nPr, and -iPr.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from: -Me and -Et.

In one embodiment, each one of $R^1$, $R^2$, $R^4$, $R^6$, and $R^9$ is independently selected from: —H, -Me, -Et, -nPr, and -iPr.

In one embodiment, each one of $R^1$, $R^2$, $R^4$, $R^6$, $R^8$, and $R^9$ is independently selected from: —H, -Me, and -Et.

In one embodiment, each one of $R^1$, $R^2$, $R^4$, $R^6$, $R^8$, and $R^9$ is independently selected from: —H and -Me.

In one embodiment, all except four of $R^1$, $R^2$, $R^4$, $R^6$, $R^8$, and $R^9$ is —H.

In one embodiment, all except two of $R^1$, $R^2$, $R^4$, $R^6$, $R^8$, and $R^9$ is —H.

In one embodiment, all except one of $R^1$, $R^2$, $R^4$, $R^6$, and $R^9$ is —H.

In one embodiment, each of $R^1$, $R^2$, $R^4$, $R^6$, $R^8$, and $R^9$ is —H.

Amino Groups

In each one of the above formulae, in each group —$NR^{3NA}R^{3NB}$, if present, each one of $R^{3NA}$ and $R^{3NB}$ is independently —H or as defined above for R; or $R^{3NA}$ and $R^{3NB}$ taken together with the nitrogen atom to which they are attached form a ring having from 3 to 7 ring atoms.

For example, in one embodiment, in each group —$NR^{3NA}R^{3NB}$, if present, each one of $R^{3NA}$ and $R^{3NB}$ is independently as defined above for R; or $R^{3NA}$ and $R^{3NB}$ taken together with the nitrogen atom to which they are attached form a ring having from 3 to 7 ring atoms.

For example, in one embodiment, in each group —$NR^{3NA}R^{3NB}$, if present, each one of $R^{3NA}$ and $R^{3NB}$ is independently selected from:
—H;
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
unsubstituted $C_{6-10}$carboaryl; substituted $C_{6-10}$carboaryl;
unsubstituted $C_{5-10}$heteroaryl; substituted $C_{5-10}$heteroaryl;
unsubstituted $C_{6-10}$carboaryl-$C_{1-4}$alkyl; substituted $C_{6-10}$carboaryl-$C_{1-4}$alkyl; or $R^{3NA}$ and $R^{3NB}$ taken together with the nitrogen atom to which they are attached form a ring having from 3 to 7 ring atoms.

For example, in one embodiment, in each group —$NR^{3NA}R^{3NB}$, if present, each one of $R^{3NA}$ and $R^{3NB}$ is independently selected from:
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
unsubstituted $C_{6-10}$carboaryl; substituted $C_{6-10}$carboaryl;
unsubstituted $C_{5-10}$heteroaryl; substituted $C_{5-10}$heteroaryl;
unsubstituted $C_{6-10}$carboaryl-$C_{1-4}$alkyl; substituted $C_{6-10}$carboaryl-$C_{1-4}$alkyl;
or $R^{3NA}$ and $R^{3NB}$ taken together with the nitrogen atom to which they are attached form a ring having from 3 to 7 ring atoms.

In another example, in one embodiment, in each group —$NR^{3NA}R^{3NB}$, if present, each one of $R^{3NA}$ and $R^{3NB}$ is independently selected from:
—H;
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
or $R^{3NA}$ and $R^{3NB}$ taken together with the nitrogen atom to which they are attached form a ring having from 3 to 7 ring atoms.

In another example, in one embodiment, in each group —$NR^{3NA}R^{3NB}$, if present, each one of $R^{3NA}$ and $R^{3NB}$ is independently selected from:
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
or $R^{3NA}$ and $R^{3NB}$ taken together with the nitrogen atom to which they are attached form a ring having from 3 to 7 ring atoms.

In another example, in one embodiment, in each group —$NR^{3NA}R^{3NB}$, if present, each one of $R^{3NA}$ and $R^{3NB}$ is independently selected from:
—H;
unsubstituted aliphatic $C_{1-6}$alkyl;
unsubstituted aliphatic $C_{2-6}$alkenyl;
unsubstituted $C_{3-6}$cycloalkyl;
or $R^{3NA}$ and $R^{3NB}$ taken together with the nitrogen atom to which they are attached form a ring having from 3 to 7 ring atoms.

In another example, in one embodiment, in each group —$NR^{3NA}R^{3NB}$, if present, each one of $R^{3NA}$ and $R^{3NB}$ is independently selected from:
unsubstituted aliphatic $C_{1-6}$alkyl;
unsubstituted aliphatic $C_{2-6}$alkenyl;
unsubstituted $C_{3-6}$cycloalkyl;
or $R^{3NA}$ and $R^{3NB}$ taken together with the nitrogen atom to which they are attached form a ring having from 3 to 7 ring atoms.

In another example, in one embodiment, in each group —$NR^{3NA}R^{3NB}$, if present, each one of $R^{3NA}$ and $R^{3NB}$ is independently selected from: —H, -Me, -Et, -nPr, and -iPr.

In another example, in one embodiment, in each group —$NR^{3NA}R^{3NB}$, if present, each one of $R^{3NA}$ and $R^{3NB}$ is independently selected from: —H, -Me, and -Et (e.g., —$NR^{3NA}R^{3NA}$ is —$NH_2$, —NHMe, —$NMe_2$, —NHEt, —$NEt_2$, or —NMeEt).

In another example, in one embodiment, in each group —$NR^{3NA}R^{3NB}$, if present, each one of $R^{3NA}$ and $R^{3NB}$ is independently selected from: —H and -Me (e.g., —$NR^{3NA}R^{3NA}$ is —$NH_2$, —NHMe, or —$NMe_2$).

In precise analogy, in each one of the above formulae, in each group —$NR^{7NA}R^{7NB}$, if present, each one of $R^{7NA}$ and $R^{7NB}$ is independently —H or as defined above for R; or $R^{7NA}$ and $R^{7NB}$ taken together with the nitrogen atom to which they are attached form a ring having from 3 to 7 ring atoms.

For example, in one embodiment, in each group —$NR^{7NA}R^{7NB}$, if present, each one of $R^{7NA}$ and $R^{7NB}$ is independently as defined above for R; or $R^{7NA}$ and $R^{7NB}$ taken together with the nitrogen atom to which they are attached form a ring having from 3 to 7 ring atoms.

In one embodiment, —$NR^{3NA}R^{3NB}$ and —$NR^{7NA}R^{7NB}$, if both present, are the same.

In one embodiment, —$NR^{3NA}R^{3NB}$ and —$NR^{7NA}R^{7NB}$, if both present, are different.

In each one of the above formulae, in each group =$NR^{3NC}$, if present, $R^{3NC}$ is independently —H or as defined above for R.

For example, in one embodiment, in each group =$NR^{3NC}$, if present, $R^{3NC}$ is independently as defined above for R.

For example, in one embodiment, in each group =NR$^{3NC}$, if present, R$^{3NC}$ is independently selected from:

—H;

unsubstituted aliphatic C$_{1-6}$alkyl; substituted aliphatic C$_{1-6}$alkyl;

unsubstituted aliphatic C$_{2-6}$alkenyl; substituted aliphatic C$_{2-6}$alkenyl;

unsubstituted C$_{3-6}$cycloalkyl; substituted C$_{3-6}$cycloalkyl;

unsubstituted C$_{6-10}$carboaryl; substituted C$_{6-10}$carboaryl;

unsubstituted C$_{5-10}$heteroaryl; substituted C$_{5-10}$heteroaryl;

unsubstituted C$_{6-10}$carboaryl-C$_{1-4}$alkyl; substituted C$_{6-10}$carboaryl-C$_{1-4}$alkyl.

For example, in one embodiment, in each group =NR$^{3NC}$, if present, R$^{3NC}$ is independently selected from:

unsubstituted aliphatic C$_{1-6}$alkyl; substituted aliphatic C$_{1-6}$alkyl;

unsubstituted aliphatic C$_{2-6}$alkenyl; substituted aliphatic C$_{2-6}$alkenyl;

unsubstituted C$_{3-6}$cycloalkyl; substituted C$_{3-6}$cycloalkyl;

unsubstituted C$_{6-10}$carboaryl; substituted C$_{6-10}$carboaryl;

unsubstituted C$_{5-10}$heteroaryl; substituted C$_{5-10}$heteroaryl;

unsubstituted C$_{6-10}$carboaryl-C$_{1-4}$alkyl; substituted C$_{6-10}$carboaryl-C$_{1-4}$alkyl.

In another example, in one embodiment, in each group =NR$^{3NC}$, if present, R$^{3NC}$ is independently selected from:

—H;

unsubstituted aliphatic C$_{1-6}$alkyl; substituted aliphatic C$_{1-6}$alkyl;

unsubstituted aliphatic C$_{2-6}$alkenyl; substituted aliphatic C$_{2-6}$alkenyl;

unsubstituted C$_{3-6}$cycloalkyl; substituted C$_{3-6}$cycloalkyl.

In another example, in one embodiment, in each group =NR$^{3NC}$, if present, R$^{3NC}$ is independently selected from:

unsubstituted aliphatic C$_{1-6}$alkyl; substituted aliphatic C$_{1-6}$alkyl;

unsubstituted aliphatic C$_{2-6}$alkenyl; substituted aliphatic C$_{2-6}$alkenyl;

unsubstituted C$_{3-6}$cycloalkyl; substituted C$_{3-6}$cycloalkyl.

In another example, in one embodiment, in each group =NR$^{3NC}$, if present, R$^{3NC}$ is independently selected from:

—H;

unsubstituted aliphatic C$_{1-6}$alkyl;

unsubstituted aliphatic C$_{2-6}$alkenyl;

unsubstituted C$_{3-6}$cycloalkyl.

In another example, in one embodiment, in each group =NR$^{3NC}$, if present, R$^{3NC}$ is independently selected from:

unsubstituted aliphatic C$_{1-6}$alkyl;

unsubstituted aliphatic C$_{2-6}$alkenyl;

unsubstituted C$_{3-6}$cycloalkyl.

In another example, in one embodiment, in each group =NR$^{3NC}$, if present, R$^{3NC}$ is independently selected from:

—H, -Me, -Et, -nPr, and -iPr.

In another example, in one embodiment, in each group =NR$^{3NC}$, if present, R$^{3NC}$ is independently selected from:

—H, -Me, and -Et (e.g., =NR$^{3NC}$ is =NH, =NMe, or =NEt).

In another example, in one embodiment, in each group =NR$^{3NC}$, if present, R$^{3NC}$ is independently selected from:

—H and -Me (e.g., =NR$^{3NC}$ is =NH or =NMe).

In precise analogy, in each one of the above formulae, in each group =NR$^{7NC}$, if present, R$^{7NC}$ is independently as defined above for R$^{3NC}$.

Nitrogen Ring Atom Substituent

Also, in precise analogy, in each one of the above formulae, R$^{N10}$, if present, is independently as defined above for R$^{3NC}$ (or R$^{7NC}$).

For example, in one embodiment, R$^{N10}$, if present, is independently selected from: —H and unsubstituted aliphatic C$_{1-6}$alkyl.

For example, in one embodiment, R$^{N10}$, if present, is independently selected from: —H, -Me, and -Et.

For example, in one embodiment, R$^{N10}$, if present, is independently selected from: —H and -Me.

For example, in one embodiment, R$^{N10}$, if present, is independently —H.

Counter Ion

X$^-$, if present, is one or more anionic counter ions to achieve electrical neutrality.

Examples of suitable anionic counter ions are discussed below under the heading "Salts".

In one embodiment, X$^-$ is independently a halogen anion (i.e., a halide).

In one embodiment, X$^-$ is independently Cl$^-$, Br$^-$, or I$^-$.

In one embodiment, X$^-$ is independently Cl$^-$.

In one embodiment, X$^-$ is independently NO$_3^-$.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

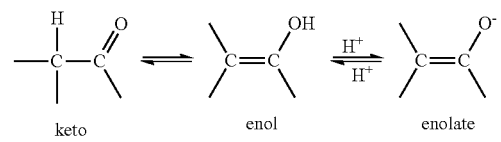

Note that specifically included in the term "isomer" are compounds with one or more isotopic substitutions. For example, H may be in any isotopic form, including $^1$H, $^2$H (D), and $^3$H (T); C may be in any isotopic form, including $^{11}$C, $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

The compound may also be provided in the form of a mixed salt (i.e., the compound in combination with a salt, or another salt). For example, methyl-thioninium chloride zinc chloride mixed salt (MTZ) is a mixed salt of methyl-thioninium chloride (MTC), a chloride salt, and another salt, zinc chloride. Such mixed salts are intended to be encompassed by the term "and pharmaceutically acceptable salts thereof".

Unless otherwise specified, a reference to a particular compound also includes salt forms thereof.

Hydrates and Solvates

It may be convenient or desirable to prepare, purify, and/or handle a corresponding solvate of the active compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate forms thereof.

In all embodiments, a preferred oxidised diaminophenothiazine is MTC.

Preferred Stable Crystalline Reduced DAPTZ Compounds

Preferred compounds are described in prior filed, unpublished, application PCT/GB2007/001103, and are 3,7-diamino-10H-phenothiazine compounds of the following formula:

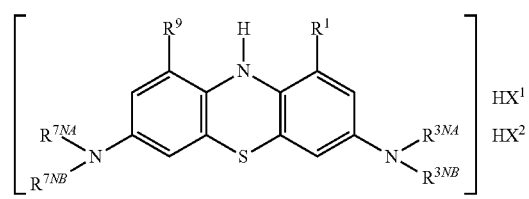

wherein:

each of R$^1$ and R$^9$ is independently selected from: —H, C$_{1-4}$alkyl, C$_{2-4}$alkenyl, and halogenated C$_{1-4}$alkyl;

each of R$^{3NA}$ and R$^{3NB}$ is independently selected from: —H, C$_{1-4}$alkyl, C$_{2-4}$alkenyl, and halogenated C$_{1-4}$alkyl;

each of R$^{7NA}$ and R$^{7NB}$ is independently selected from: —H, C$_{1-4}$alkyl, C$_{2-4}$alkenyl, and halogenated C$_{1-4}$alkyl;

each of HX$^1$ and HX$^2$ is independently a protic acid;

and pharmaceutically acceptable salts, solvates, and hydrates thereof.

Without wishing to be bound to any particular theory, the inventors believe that it is possible, if not likely, that the compounds exist in the following form:

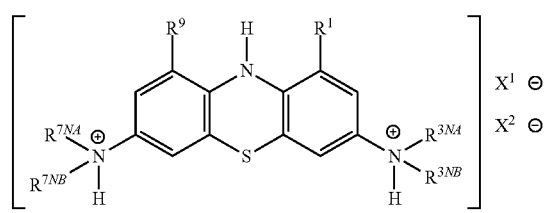

Although the DAPTZ compounds are themselves salts, they may also be provided in the form of a mixed salt (i.e., the DAPTZ in combination with another salt). Such mixed salts are intended to be encompassed by the term "and pharmaceutically acceptable salts thereof". Unless otherwise specified, a reference to a particular compound also includes salts thereof.

The DAPTZ compounds may also be provided in the form of a solvate or hydrate. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc. Unless otherwise specified, a reference to a particular compound also includes solvate forms thereof.

In one embodiment, the $C_{1-4}$alkyl groups are selected from: linear $C_{1-4}$alkyl groups, such as -Me, -Et, -nPr, -iPr, and -nBu; branched $C_{3-4}$alkyl groups, such as -iPr, -iBu, -sBu, and -tBu; and cyclic $C_{3-4}$alkyl groups, such as -cPr and -cBu.

In one embodiment, the $C_{2-4}$alkenyl groups are selected from linear $C_{1-4}$alkenyl groups, such as —CH=CH$_2$ (vinyl) and —CH$_2$—CH=CH$_2$ (allyl).

In one embodiment, the halogenated $C_{1-4}$alkyl groups are selected from: —CF$_3$, —CH$_2$CF$_3$, and —CF$_2$CF$_3$.

The Groups $R^1$ and $R^9$

In one embodiment, each of $R^1$ and $R^9$ is independently —H, -Me, -Et, or —CF$_3$.

In one embodiment, each of $R^1$ and $R^9$ is independently —H, -Me, or -Et.

In one embodiment, $R^1$ and $R^9$ are the same.

In one embodiment, $R^1$ and $R^9$ are different.

In one embodiment, each of $R^1$ and $R^9$ is independently —H.

In one embodiment, each of $R^1$ and $R^9$ is independently -Me.

In one embodiment, each of $R^1$ and $R^9$ is independently -Et.

The Groups $R^{3NA}$ and $R^{3NB}$

Each of $R^{3NA}$ and $R^{3NB}$ is independently selected from: —H, $C_{1-4}$alkyl, $C_{2-4}$alkenyl, and halogenated $C_{1-4}$alkyl.

In one embodiment, each of $R^{3NA}$ and $R^{3NB}$ is independently selected from: $C_{1-4}$alkyl, $C_{2-4}$alkenyl, and halogenated $C_{1-4}$alkyl.

In one embodiment, each of $R^{3NA}$ and $R^{3NB}$ is independently -Me, -Et, -nPr, -nBu, —CH$_2$—CH=CH$_2$, or —CF$_3$.

In one embodiment, each of $R^{3NA}$ and $R^{3NB}$ is independently -Me, -nPr, -nBu, —CH$_2$—CH=CH$_2$, or —CF$_3$.

In one embodiment, each of $R^{3NA}$ and $R^{3NB}$ is independently -Me or -Et.

In one embodiment, $R^{3NA}$ and $R^{3NB}$ are the same.

In one embodiment, $R^{3NA}$ and $R^{3NB}$ are different.

In one embodiment, each of $R^{3NA}$ and $R^{3NB}$ is independently -Me.

In one embodiment, each of $R^{3NA}$ and $R^{3NB}$ is independently -Et.

The Groups $R^{7NA}$ and $R^{7NB}$

Each of $R^{7NA}$ and $R^{7NB}$ is independently selected from: —H, $C_{1-4}$alkyl, $C_{2-4}$alkenyl, and halogenated $C_{1-4}$alkyl.

In one embodiment, each of $R^{7NA}$ and $R^{7NB}$ is independently selected from: $C_{1-4}$alkyl, $C_{2-4}$alkenyl, and halogenated $C_{1-4}$alkyl.

In one embodiment, each of $R^{7NA}$ and $R^{7NB}$ is independently -Me, -Et, -nPr, -nBu, —CH$_2$—CH=CH$_2$, or —CF$_3$.

In one embodiment, each of $R^{7NA}$ and $R^{7NB}$ is independently -Me, -nPr, -nBu, —CH$_2$—CH=CH$_2$, or —CF$_3$.

In one embodiment, each of $R^{7NA}$ and $R^{7NB}$ is independently -Me or -Et.

In one embodiment, $R^{7NA}$ and $R^{7NB}$ are the same.

In one embodiment, $R^{7NA}$ and $R^{7NB}$ are different.

In one embodiment, each of $R^{7NA}$ and $R^{7NB}$ is independently -Me.

In one embodiment, each of $R^{7NA}$ and $R^{7NB}$ is independently -Et.

In one embodiment, $R^{3NA}$ and $R^{3NB}$ and $R^{7NA}$ and $R^{7NB}$ are the same.

In one embodiment, $R^{3NA}$ and $R^{3NB}$ and $R^{7NA}$ and $R^{7NB}$ are as defined herein, with the proviso that at least one of $R^{3NA}$ and $R^{3NB}$ and $R^{7NA}$ and $R^{7NB}$ is other than -Et.

Optional Provisos

In one embodiment, the compound is as defined herein, but with the proviso that:
$R^{3NA}$ and $R^{3NB}$ and $R^{7NA}$ and $R^{7NB}$ are not each -Et.

In one embodiment, the compound is as defined herein, but with the proviso that: if: each of $R^1$ and $R^9$ is —H; then: $R^{3NA}$ and $R^{3NB}$ and $R^{7NA}$ and $R^{7NB}$ are not each -Et.

The Groups —N($R^{3NA}$)($R^{3NB}$) and —N($R^{7NA}$)($R^{7NB}$)

In one embodiment:
each of $R^{3NA}$ and $R^{3NB}$ is independently $C_{1-4}$alkyl, $C_{2-4}$alkenyl, or halogenated $C_{1-4}$alkyl;
each of $R^{7NA}$ and $R^{7NB}$ is independently $C_{1-4}$alkyl, $C_{2-4}$alkenyl, or halogenated $C_{1-4}$alkyl;
optionally with the proviso that at least one of $R^{3NA}$ and $R^{3NB}$ and $R^{7NA}$ and $R^{7NB}$ is other than -Et.

In one embodiment:
each of $R^{3NA}$ and $R^{3NB}$ is independently -Me, -Et, -nPr, -nBu, —CH$_2$—CH=CH$_2$, or —CF$_3$;
each of $R^{7NA}$ and $R^{7NB}$ is independently -Me, -Et, -nPr, -nBu, —CH$_2$—CH=CH$_2$, or —CF$_3$;
optionally with the proviso that at least one of $R^{3NA}$ and $R^{3NB}$ and $R^{7NA}$ and $R^{7NB}$ is other than -Et.

In one embodiment:
each of $R^{3NA}$ and $R^{3NB}$ is independently -Me or -Et;
each of $R^{7NA}$ and $R^{7NB}$ is independently -Me or -Et;
optionally with the proviso that at least one of $R^{3NA}$ and $R^{3NB}$ and $R^{7NA}$ and $R^{7NB}$ is other than -Et.

In one embodiment, the groups —N($R^{3NA}$)($R^{3NB}$) and —N($R^{7NA}$)($R^{7NB}$) are the same.

In one embodiment, the groups —N($R^{3NA}$)($R^{3NB}$) and —N($R^{7NA}$)($R^{7NB}$) are different.

In one embodiment, each of the groups —N($R^{3NA}$)($R^{3NB}$) and —N($R^{7NA}$)($R^{7NB}$) is independently selected from: —NMe$_2$, —NEt$_2$, —N(nPr)$_2$, —N(Bu)$_2$, —NMeEt, —NMe(nPr), and —N(CH$_2$CH=CH$_2$)$_2$.

In one embodiment, the groups —N($R^{3NA}$)($R^{3NB}$) and —N($R^{7NA}$)($R^{7NB}$) are the same, and are independently selected from: —NMe$_2$, —NEt$_2$, —N(nPr)$_2$, —N(Bu)$_2$, —NMeEt, —NMe(nPr), and —N(CH$_2$CH=CH$_2$)$_2$.

In one embodiment, the groups —N($R^{3NA}$)($R^{3NB}$) and —N($R^{7NA}$)($R^{7NB}$) are the same, and are independently selected from: —NMe$_2$ and —NEt$_2$.

In one embodiment, each of the groups —N($R^{3NA}$)($R^{3NB}$) and —N($R^{7NA}$)($R^{7NB}$) is: —NMe$_2^+$.

In one embodiment, at least one of the groups —N($R^{3NA}$)($R^{3NB}$) and —N($R^{7NA}$)($R^{7NB}$) is other than —NEt$_2$.

In one embodiment, each of the groups —N($R^{3NA}$)($R^{3NB}$) and —N($R^{7NA}$)($R^{7NB}$) is other than —NEt$_2$.

For example, in one embodiment, the groups —N($R^{3NA}$)($R^{3NB}$) and —N($R^{7NA}$)($R^{7NB}$) are the same, and are selected from: —NMe$_2$, —N(nPr)$_2$, —N(Bu)$_2$, —NMeEt, —NMe(nPr), and —N(CH$_2$CH=CH$_2$)$_2$.

The Groups HX$^1$ and HX$^2$

Each of HX$^1$ and HX$^2$ is independently a protic acid.

Examples of protic acids include, for example, inorganic acids, such as hydrohalide acids (e.g., HCl, HBr, HI), nitric acid (HNO$_3$), sulphuric acid (H$_2$SO$_4$), and organic acids, such as carbonic acid (H$_2$CO$_3$) and acetic acid (CH$_3$COOH).

In one embodiment, each of HX$^1$ and HX$^2$ is independently a monoprotic acid.

In one embodiment, each of HX$^1$ and HX$^2$ is independently a hydrohalide acid (i.e., a hydrohalic acid)

In one embodiment, each of HX$^1$ and HX$^2$ is independently selected from HCl, HBr, and HI.

In one embodiment, HX$^1$ and HX$^2$ are the same.

In one embodiment, HX$^1$ and HX$^2$ are different.

In one embodiment, $HX^1$ and $HX^2$ are the same, and are independently selected from HCl, HBr, and HI. In this case, the compound (a diamino-phenothiazine compound) may conveniently be referred to as a "diamino-phenothiazine bis(hydrogen halide) salt".

In one embodiment, $HX^1$ and $HX^2$ are each HCl. In this case, the compound may conveniently be referred to as a "diamino-phenothiazine bis(hydrogen chloride) salt".

In one embodiment, $HX^1$ and $HX^2$ are each HBr. In this case, the compound may conveniently be referred to as a "diamino-phenothiazine bis(hydrogen bromide) salt".

In one embodiment, $HX^1$ and $HX^2$ are each HI. In this case, the compound may conveniently be referred to as a "diamino-phenothiazine bis(hydrogen iodide) salt".

Some Preferred Combinations

In one embodiment:
each of $R^1$ and $R^9$ is independently —H, -Me, or -Et; and
each of the groups —N($R^{3NA}$)($R^{3NB}$) and —N($R^{7NA}$)($R^{7NB}$) is independently —NMe$_2$ or —NEt$_2$.

In one embodiment:
each of $R^1$ and $R^9$ is independently —H, -Me, or -Et; and
each of the groups —N($R^{3NA}$)($R^{3NB}$) and —N($R^{7NA}$)($R^{7NB}$) is independently —NMe$_2$.

In one embodiment:
each of $R^1$ and $R^9$ is independently —H; and
each of the groups —N($R^{3NA}$)($R^{3NB}$) and —N($R^{7NA}$)($R^{7NB}$) is independently —NMe$_2$ or —NEt$_2$.

In one embodiment:
each of $R^1$ and $R^9$ is independently —H; and
each of the groups —N($R^{3NA}$)($R^{3NB}$) and —N($R^{7NA}$)($R^{7NB}$) is independently —NMe$_2$.

In one embodiment:
each of $R^1$ and $R^9$ is independently —H, -Me, or -Et; and
each of the groups —N($R^{3NA}$)($R^{3NB}$) and —N($R^{7NA}$)($R^{7NB}$) is independently —NMe$_2$ or —NEt$_2$; and
each of $HX^1$ and $HX^2$ is independently selected from HCl, HBr, and HI.

In one embodiment:
each of $R^1$ and $R^9$ is independently —H, -Me, or -Et; and
each of the groups —N($R^{3NA}$)($R^{3NB}$) and —N($R^{7NA}$)($R^{7NB}$) is independently —NMe$_2$; and
each of $HX^1$ and $HX^2$ is independently selected from HCl, HBr, and HI.

In one embodiment:
each of $R^1$ and $R^9$ is independently —H; and
each of the groups —N($R^{3NA}$)($R^{3NB}$) and —N($R^{7NA}$)($R^{7NB}$) is independently —NMe$_2$ or —NEt$_2$; and
each of $HX^1$ and $HX^2$ is independently selected from HCl, HBr, and HI.

In one embodiment:
each of $R^1$ and $R^9$ is independently —H; and
each of the groups —N($R^{3NA}$)($R^{3NB}$) and —N($R^{7NA}$)($R^{7NB}$) is independently —NMe$_2$; and
each of $HX^1$ and $HX^2$ is independently selected from HCl, HBr, and HI.

In one embodiment:
each of $R^1$ and $R^9$ is independently —H; and
each of the groups —N($R^{3NA}$)($R^{3NB}$) and —N($R^{7NA}$)($R^{7NB}$) is independently —NMe$_2$; and
each of $HX^1$ and $HX^2$ is HCl.

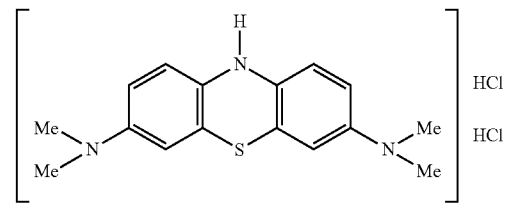

In one embodiment:
each of $R^1$ and $R^9$ is independently —H; and
each of the groups —N($R^{3NA}$)($R^{3NB}$) and —N($R^{7NA}$)($R^{7NB}$) is independently —NMe$_2$; and
each of $HX^1$ and $HX^2$ is HBr.

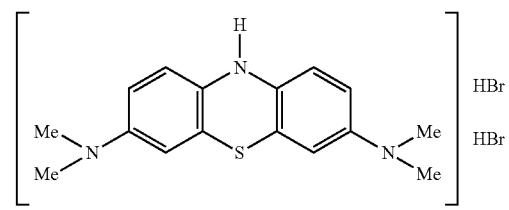

In one embodiment:
each of $R^1$ and $R^9$ is independently —H; and
each of the groups —N($R^{3NA}$)($R^{3NB}$) and —N($R^{7NA}$)($R^{7NB}$) is independently —NMe$_2$; and
each of $HX^1$ and $HX^2$ is HI.

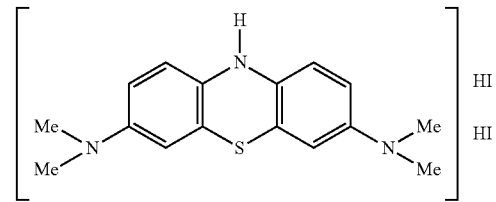

Isotopic Variation

In one embodiment, one or more of the carbon atoms of the compound is $^{11}$C, $^{13}$C, or $^{14}$C.

In one embodiment, one or more of the carbon atoms of the compound is $^{11}$C.

In one embodiment, one or more of the carbon atoms of the compound is $^{13}$C.

In one embodiment, one or more of the carbon atoms of the compound is $^{14}$C.

In one embodiment, one or more of the nitrogen atoms of the compound is $^{15}$N.

In one embodiment, one or more or all of the carbon atoms of one or more or all of the groups $R^{3NA}$, $R^{3NB}$, $R^{7NA}$, $R^{7NB}$, $R^1$, $R^9$, and $R^{10}$ is $^{11}$C. (Or $^{13}$C.) (Or $^{14}$C.)

In one embodiment, one or more or all of the carbon atoms of one or more or all of the groups $R^{3NA}$, $R^{3NB}$, $R^{7NA}$, and $R^{7NB}$ is $^{11}$C. (Or $^{13}$C.) (Or $^{14}$C.)

In one embodiment, the groups —N($R^{3NA}$)($R^{3NB}$) and —N($R^{7NA}$)($R^{7NB}$) are the same, and are: —N($^{11}$CH$_3$)$_2$. (Or —N($^{13}$CH$_3$)$_2$.) (Or —N($^{14}$CH$_3$)$_2$.)

In one embodiment, the compound is selected from the following compounds, and pharmaceutically acceptable salts, solvates, and hydrates thereof.

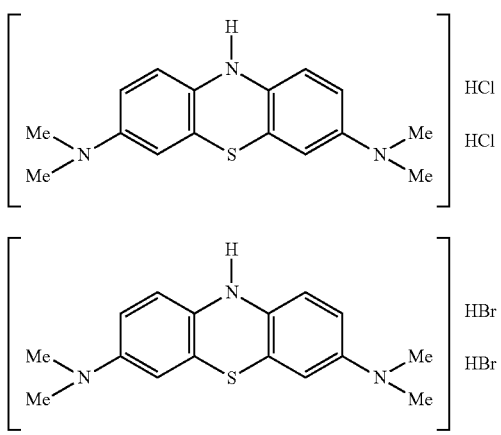

OTHER ASPECTS OF THE INVENTION

Where any method of treatment is disclosed herein, also disclosed are:

A DAPTZ compound for use in that method and use of DAPTZ compound in the preparation of a medicament for said treatment. Corresponding embodiments, preferences, and individualizations, described herein apply mutatis mutandis to these aspects.

Thus the invention provides inter alia:

A DAPTZ compound for use in a method of treatment of a cognitive or CNS disorder in a patient, wherein said disorder is one which is susceptible to treatment by said DAPTZ compound, which method comprises orally administering to said patient a dosage unit containing said DAPTZ compound in oxidised form as active ingredient, wherein said dosage unit releases at least 50% of said active ingredient within 30 minutes under standard conditions.

A DAPTZ compound for use in a method of treatment of a cognitive or CNS disorder in a patient, wherein said disorder is one which is susceptible to treatment by said DAPTZ compound, which method comprises orally administering to said patient a dosage unit containing said DAPTZ compound in oxidised form as active ingredient, wherein said dosage unit is gastroretained.

A DAPTZ compound for use in a method of treatment of a cognitive or CNS disorder in a patient, wherein said disorder is one which is susceptible to treatment by said DAPTZ compound, which method comprises orally administering to said patient a dosage unit containing said DAPTZ compound in stable crystalline reduced form as active ingredient, Use of a DAPTZ compound in the preparation of a medicament dosage unit for use in a method of treatment of a cognitive or CNS disorder in a patient, wherein said disorder is one which is susceptible to treatment by said DAPTZ compound, which method comprises orally administering to said patient said dosage unit containing said DAPTZ compound in oxidised form as active ingredient, wherein said dosage unit releases at least 50% of said active ingredient within 30 minutes under standard conditions.

Use of a DAPTZ compound in the preparation of a medicament dosage unit for use in a method of treatment of a cognitive or CNS disorder in a patient, wherein said disorder is one which is susceptible to treatment by said DAPTZ compound, which method comprises orally administering to said patient said dosage unit containing said DAPTZ compound in oxidised form as active ingredient, wherein said dosage unit is gastroretained.

Use of a DAPTZ compound in the preparation of a medicament dosage unit for use in a method of treatment of a cognitive or CNS disorder in a patient, wherein said disorder is one which is susceptible to treatment by said DAPTZ compound, which method comprises orally administering to said patient a dosage unit containing said DAPTZ compound in stable crystalline reduced form as active ingredient, In one aspect the invention provides a drug unit for the treatment of a cognitive or CNS disorder in a patient, wherein said disorder is one which is susceptible to treatment by a DAPTZ compound, which dosage unit contains said DAPTZ compound in oxidised form as active ingredient, and wherein said dosage unit releases at least 50% of said active ingredient within 30 minutes under standard conditions. The dosage units comprise may comprise, for example, 40, 45, 50, 55, 60, 65, 70, 100, 120 mg of a DAPTZ compound as described.

In one aspect the invention provides a drug unit for the treatment of a cognitive or CNS disorder in a patient, wherein said disorder is one which is susceptible to treatment by a DAPTZ compound, which dosage unit contains said DAPTZ compound in oxidised form as active ingredient, and wherein said dosage unit is gastroretained. The dosage unit may comprise at least 50, 60, 70, 80, 90 or 100 mg, or more e.g. 200, 300, 400, 500 mg of a DAPTZ compound as described.

In one aspect the invention provides a drug unit for the treatment of a cognitive or CNS disorder in a patient, wherein said disorder is one which is susceptible to treatment by a DAPTZ compound, which dosage unit contains said DAPTZ compound in stable crystalline reduced form as active ingredient, at a dosage described above (e.g. 100, 200, 300, 400, 500, 600, 700, 800, 900, or 1000 mg), and having a dissolution rate described above (e.g. <50% in 1 hour, 2 hours, 3 hours, 4 hours, or 5 hours).

Also provided is a drug product comprising said unity accompanied by a label indicating that the drug product is for the treatment of said disease, the container containing one or more dosage units each comprising at least one pharmaceutically acceptable excipient and, as an active ingredient, an isolated pure diaminophenothiazinium compound as described herein.

Ligands

Additionally use as diagnostic or prognostic indicator e.g. as a ligand for labelling protein aggregates in the brain is also contemplated. The findings herein in which cognitive effect (dependent on brain concentration) vs. negative haematological effect (deduced to be from dimer formation) have implications also for use as a ligand.

Such DAPTZ compounds (ligands) may incorporate, be conjugated to, be chelated with, or otherwise be associated with, other chemical groups, such as stable and unstable detectable isotopes, radioisotopes, positron-emitting atoms, magnetic resonance labels, dyes, fluorescent markers, antigenic groups, therapeutic moieties, or any other moiety that may aid in a prognostic, diagnostic, or therapeutic application.

For example, in one embodiment, the DAPTZ compound is as defined herein, but with the additional limitation that the compound incorporates, is conjugated to, is chelated with, or is otherwise associated with, one or more (e.g., 1, 2, 3, 4, etc.) detectable labels, for example, isotopes, radioisotopes, positron-emitting atoms, magnetic resonance labels, dyes, fluorescent markers, antigenic groups, or therapeutic moieties.

In one embodiment, the DAPTZ compound is a ligand as well as a label, e.g., a label for tau protein (or aggregated tau protein), and incorporates, is conjugated to, is chelated with, or is otherwise associated with, one or more (e.g., 1, 2, 3, 4, etc.) detectable labels.

For example, in one embodiment, the DAPTZ compound is as defined above, but with the additional limitation that the compound incorporates, is conjugated to, is chelated with, or is otherwise associated with, one or more (e.g., 1, 2, 3, 4, etc.) detectable labels.

Labelled DAPTZ compounds (e.g., when ligated to tau protein or aggregated tau protein) may be visualised or detected by any suitable means, and the skilled person will appreciate that any suitable detection means as is known in the art may be used.

For example, the DAPTZ compound (ligand-label) may be suitably detected by incorporating a positron-emitting atom (e.g., $^{11}C$) (e.g., as a carbon atom of one or more alkyl group substituents, e.g., methyl group substituents) and detecting the compound using positron emission tomography (PET) as is known in the art.

Such $^{11}C$ labelled DAPTZ compounds may be prepared by adapting the methods described herein in known ways, for example, in analogy to the methods described in WO 02/075318 (see FIGS. 11a, 11b, 12) and WO 2005/030676.

Thus in one aspect there is disclosed a method of labelling an aggregated disease protein associated with a neurodegenerative disorder in the brain of a patient, wherein said aggregated disease protein is one which is susceptible to labelling by a DAPTZ compound, which method comprises orally administering to said patient a dosage unit containing said DAPTZ compound in oxidised form as active-labelled ingredient, wherein said dosage unit releases at least 50% of said active ingredient within 30 minutes under standard conditions.

In a further aspect there is disclosed a method of labelling an aggregated disease protein associated with a neurodegenerative disorder in the brain of a patient, wherein said aggregated disease protein is one which is susceptible to labelling by a DAPTZ compound, which method comprises orally administering to said patient a dosage unit containing said DAPTZ compound in oxidised form as active-labelled ingredient, wherein said dosage unit is gastroretained.

In a further aspect there is disclosed a method of labelling an aggregated disease protein associated with a neurodegenerative disorder in the brain of a patient, wherein said aggregated disease protein is one which is susceptible to labelling by a DAPTZ compound, which method comprises orally administering to said patient a dosage unit containing said DAPTZ compound in stable crystalline reduced form as active-labelled ingredient.

Preferred aggregated disease proteins, DAPTZ compounds, and neurodegenerative disorders are discussed elsewhere herein.

The methods may further comprise the step of determining the presence and/or amount of said compound bound to said aggregated protein. Another aspect of the present invention pertains to a method of diagnosis or prognosis of said neurodegenerative disorder which further comprises the step of correlating the result of the determination with the disease state of the subject.

Where any method of labelling, diagnosis or prognosis is disclosed herein, also disclosed are:

A DAPTZ compound for use in that method and use of DAPTZ compound in the preparation of a diagnostic or prognostic indicator for said method. Corresponding embodiments, preferences, and individualizations, described herein apply mutatis mutandis to these aspects.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

All compatible combinations of the embodiments described above are explicitly disclosed herein as if each combination was specifically and individually recited.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

(1) SPM analysis shows regions where visit 4 had significantly less rCBF than visit 1 in subjects treated with placebo. Threshold for difference p<0.005, corrected p<0.05 for multiple comparisons, both voxel and cluster significance. R=right, L=left, A=anterior, P=posterior. The upper pair in each panel represent anterior (left) and posterior (right) views respectively.

(2) SPM analysis shows no regions where visit 4 had significantly less rCBF than visit 1 in subjects treated with REMBER™ at 30 mg or 60 mg tid. Threshold for difference p<0.005, corrected p<0.05 for multiple comparisons, both voxel and cluster significance.

(3) Locations of treatment-dependent difference in decline between baseline and visit 4 in CDR-mild subjects treated with placebo versus those with REMBER™ at 30/60 mg tid. Threshold for difference p<0.005, corrected p<0.05 for multiple comparisons, both voxel and cluster significance.

Figure 4:
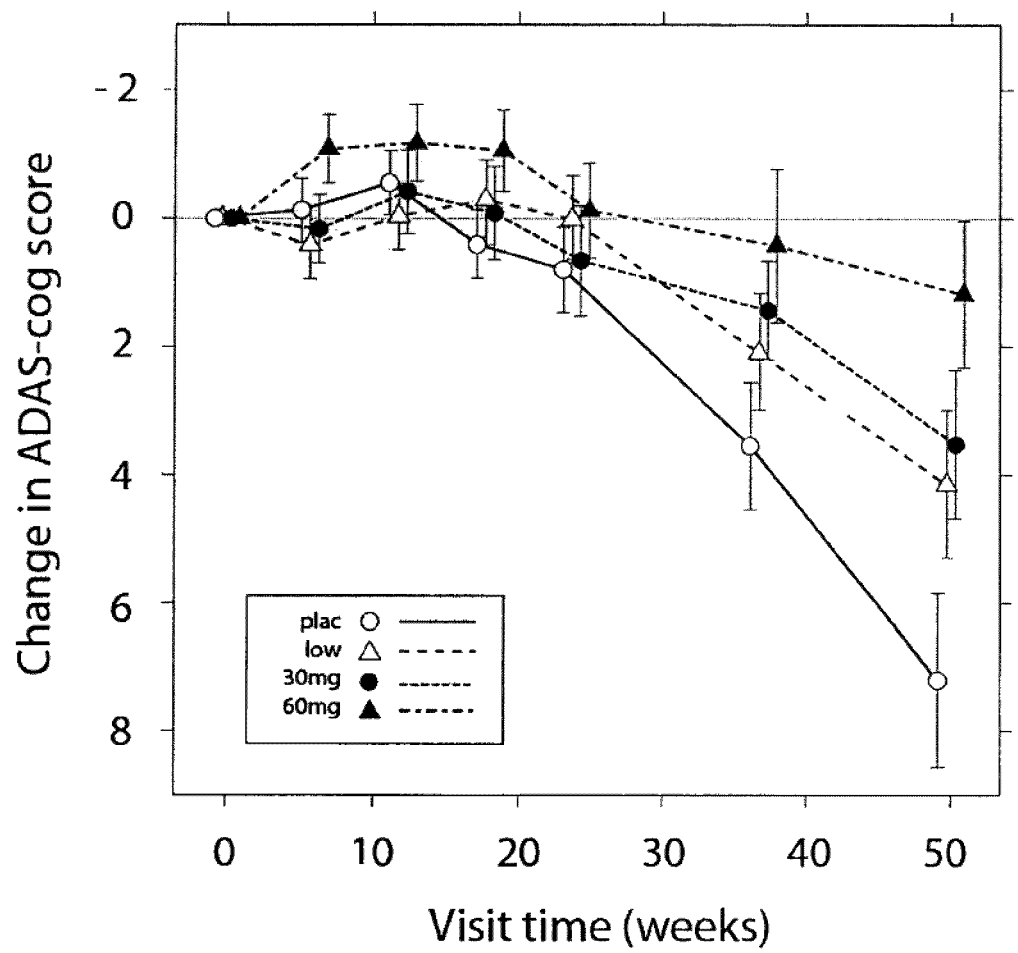

FIG. 4. ITT/OC ADAS-cog change from baseline and fitted curves. For this chart, the labelling conventions of "placlow" refers to subjects who were originally randomised to placebo and were then switched to the 100 mg dose bd after 24 weeks, "low" refers to low (100 mg) dose tid, "30 mg" refers to 30 mg dose tid and "60 mg" refers to 60 mg dose tid.

Figure 5:
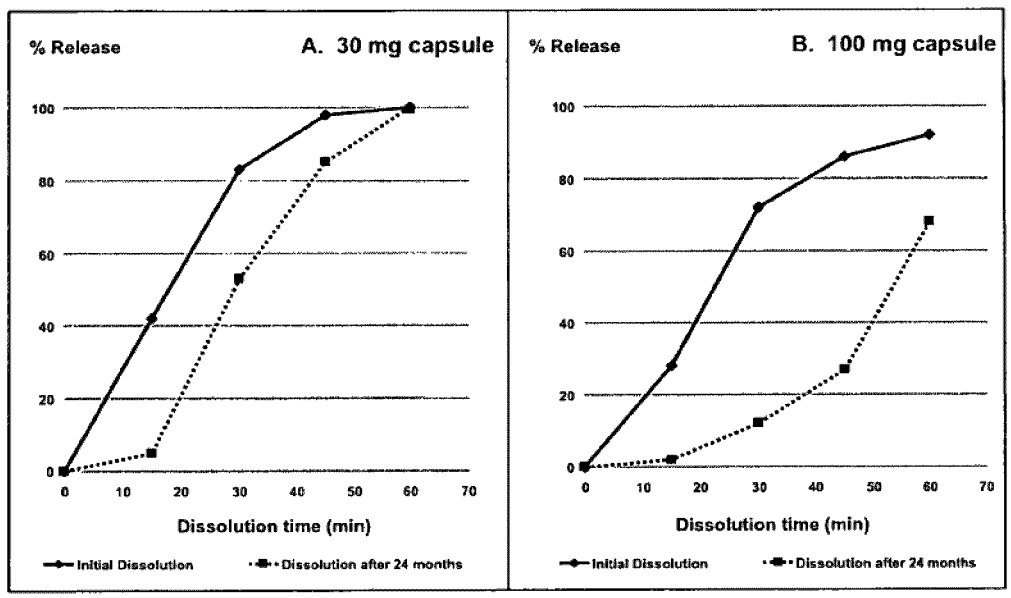

FIG. 5. Dissolution of capsules in simulated intestinal fluid by dosage: (A) 30 mg and (B) 100 mg capsules dissolved initially and following 24 months storage. Dissolution of the 100 mg capsule was slower than the 30 mg capsule and this difference increased with time since manufacture.

Figure 6A:
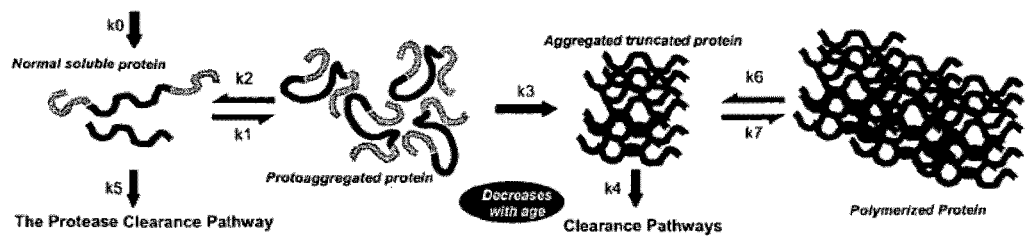

FIG. 6A. REMBER™ inhibits nucleation event and autocatalytic tau aggregation.

Figure 6B:
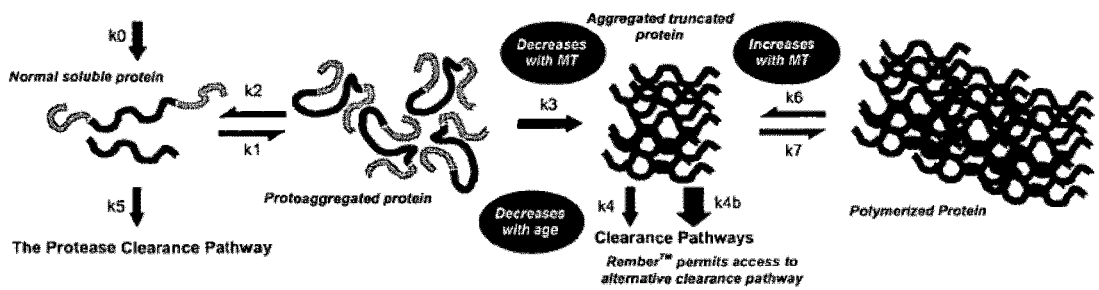

FIG. 6B. REMBER™ opens a new clearance pathway for tau aggregates.

Figure 7:
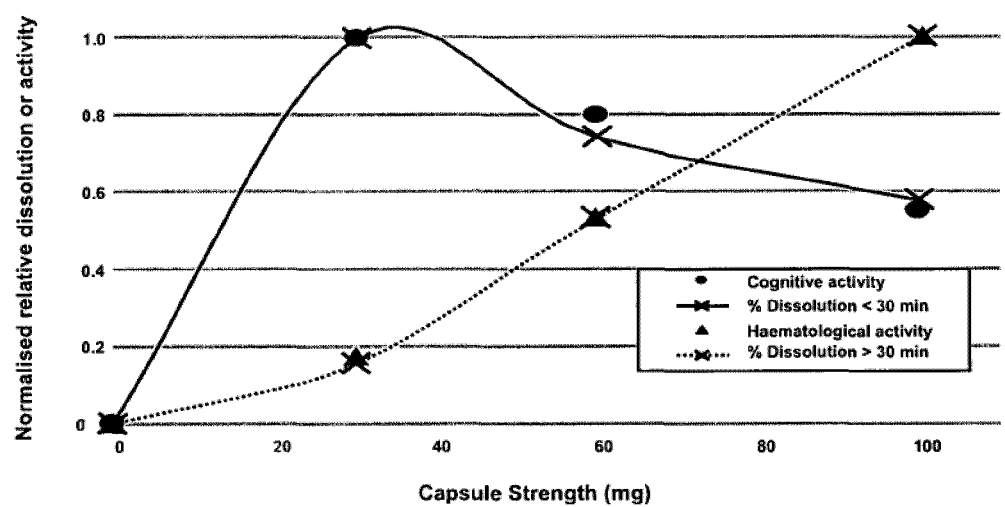

FIG. 7. Relationship between dissolution time and relative cognitive and haematological effects. Dissolution % is a adjusted based on the calculations below:

A cognitive activity index (CI) was first determined as the normalised ADAS-cog effect size at 50 weeks at each nominal dose relative to the maximal effect size observed at 50 weeks, using the linear least-squares estimates of effect size. A corresponding haematological activity index (HI) was expressed as the normalised change in red-cell count at 24 weeks at each nominal dose relative to the maximal red cell effect size observed. The time-points of 50 weeks for cognitive and 24 weeks for haematological effects were chosen because the corresponding effects were maximal at these times. The relative cognitive activity was expressed in the form CI/(CI+HI) and the relative haematological activity was expressed in the form HI/(CI+HI), and both of these relative activities were normalised to their corresponding maxima across doses. A similar calculation was used to express the relative percentage of MTC available in solution before or after 30 minutes relative to the total, based on dissolution data from 24-month-old capsules, when the dissolution differences between capsule strengths were maximal. The relationships explicitly calculated can be expressed as follows:

$$\alpha CI/[\alpha CI+(1-\alpha)HI] \approx D_{30}/D_{total} \quad (1)$$

$$(1-\alpha)HI/[\alpha CI+(1-\alpha)HI] \approx (1-D_{30})/D_{total} \quad (2)$$

where $\alpha$ is a scaling parameter for relating CI units to HI units (found to be 0.645 by least squares estimation), $D_{30}$ is the percentage of total MTC available from 24-month capsules at 30 minutes, and $D_{total}$ is the total nominal dose which is eventually dissolved.

Figure 8:
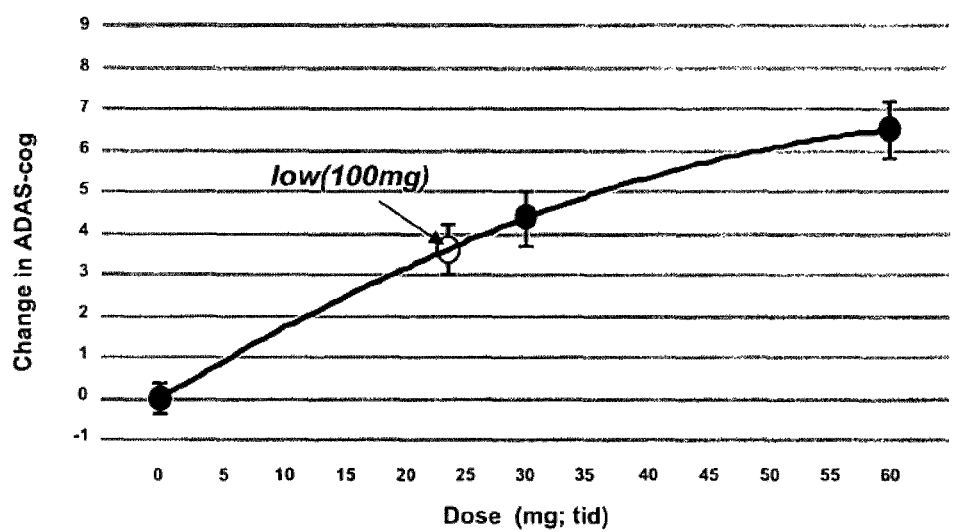

FIG. 8. Implied dose-response relationship at 50 weeks. Effect sizes calculated using linear least-squares estimates at 50 weeks. The effective therapeutic dose available from the 100 mg capsule was equivalent to a dose of approximately 25 mg, indicating that the capsules did not permit proportionate delivery and absorption of the nominal dose in a therapeutically active form.

Figure 9:
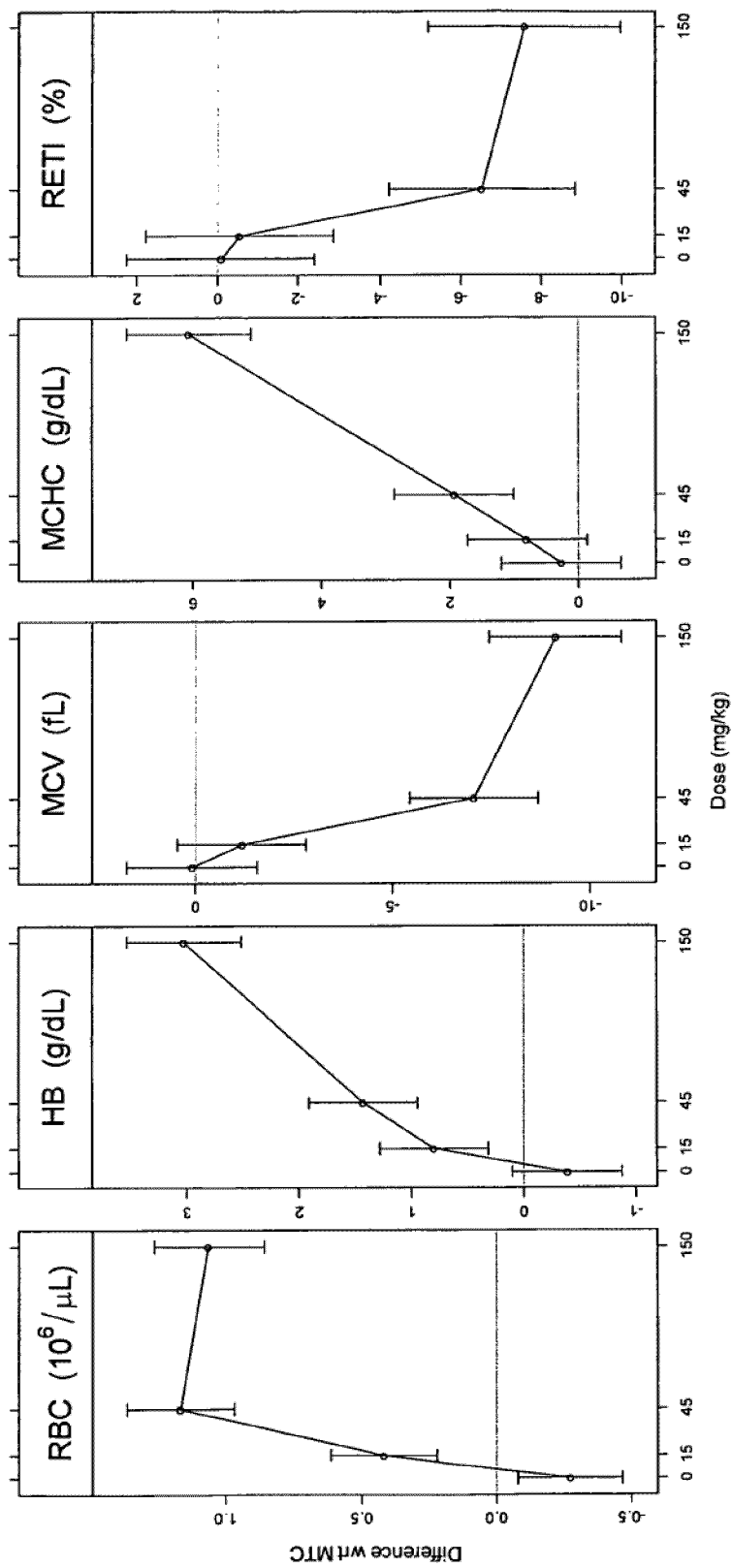

FIG. 9. Differences in key red cell parameters in rats between MTC and L-MTx administered orally for 14-days at the indicated daily doses. Differences are shown terms of change observed with L-MTx with respect to MTC. For example, at a dose of 150 mg/kg L-MTx, red cell count is increased by $>1\times10^6/\mu l$ and the mean cell haemoglobin concentration is increased by 3 µg/dL. The statistical analysis of the data is shown in Table 4. Abbreviations and units: RBC: red cell count, $10^6/\mu L$; HB: haemoglobin, g/dL; MCV: mean cell volume, fL; MCHC: mean cell haemoglobin concentration, g/dL; RETI: reticulocyte count, % of red cells.

Figure 10:
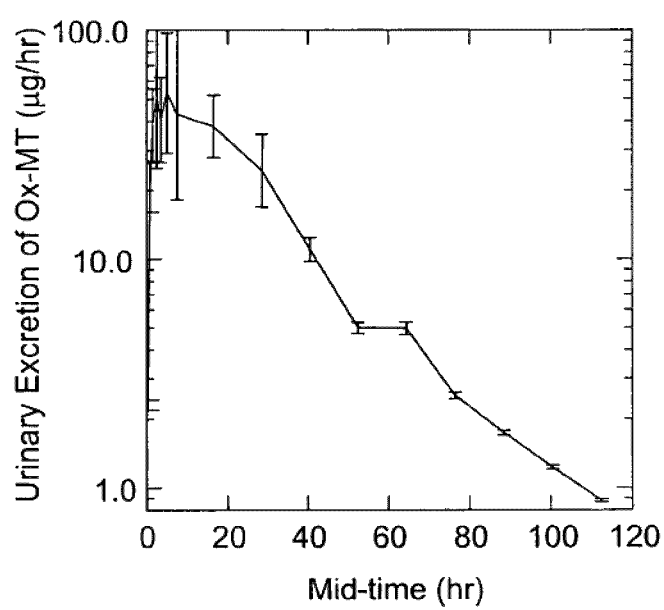

FIG. 10. Average urinary excretion rates for oxidised-MTC (Ox-MT) from 7 adult human subjects following 10 mg oral dose (mean, SE). (From DiSanto and Wagner, 1972b).

Figure 11:
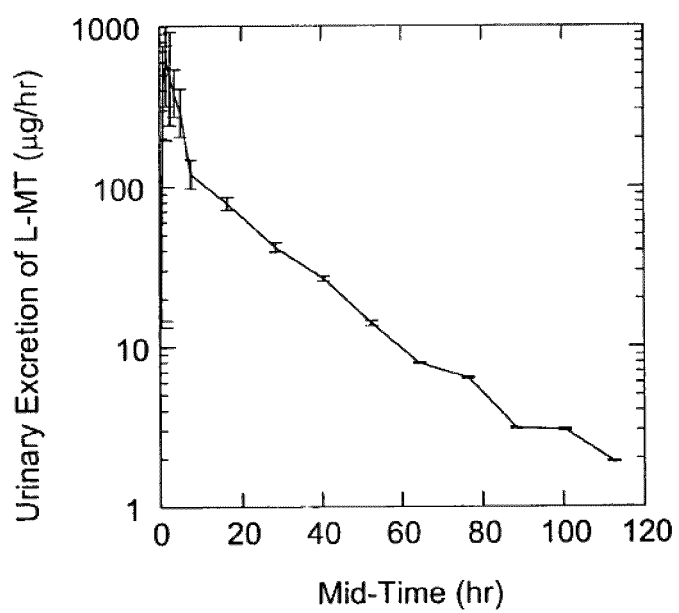

FIG. 11. Average urinary excretion rates for leuco-MT (L-MT) from 7 adult human subjects following 10 mg oral dose (mean, SE). (From DiSanto and Wagner, 1972b).

Figure 12:
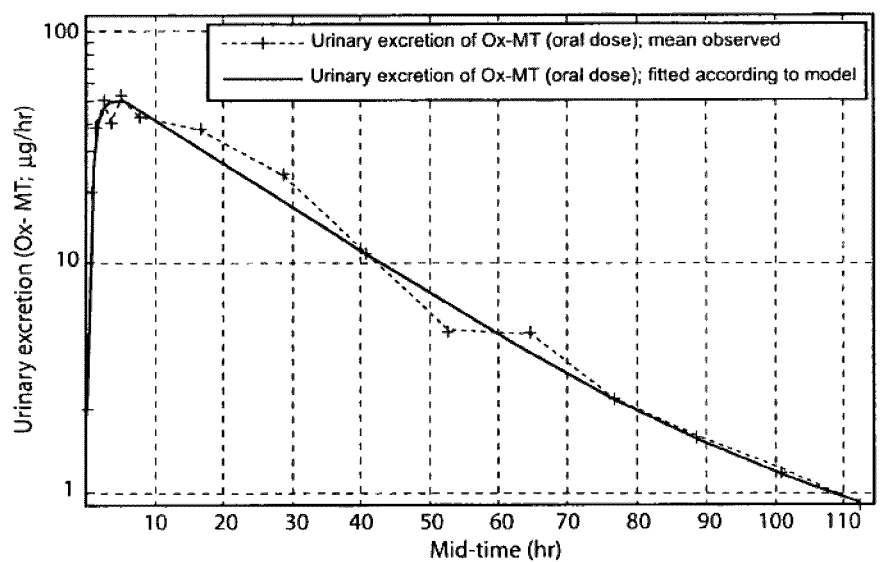

FIG. 12. Urinary excretion rate for Ox-MTC following a 10 mg oral dose.

Figure 13:
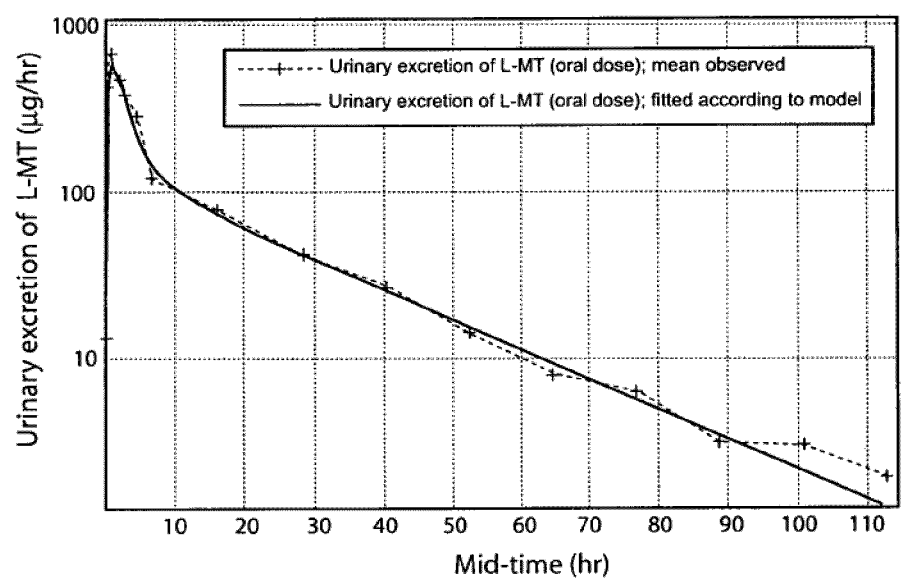

FIG. 13. Urinary excretion rate for L-MT following a 10 mg oral dose.

Figure 14:
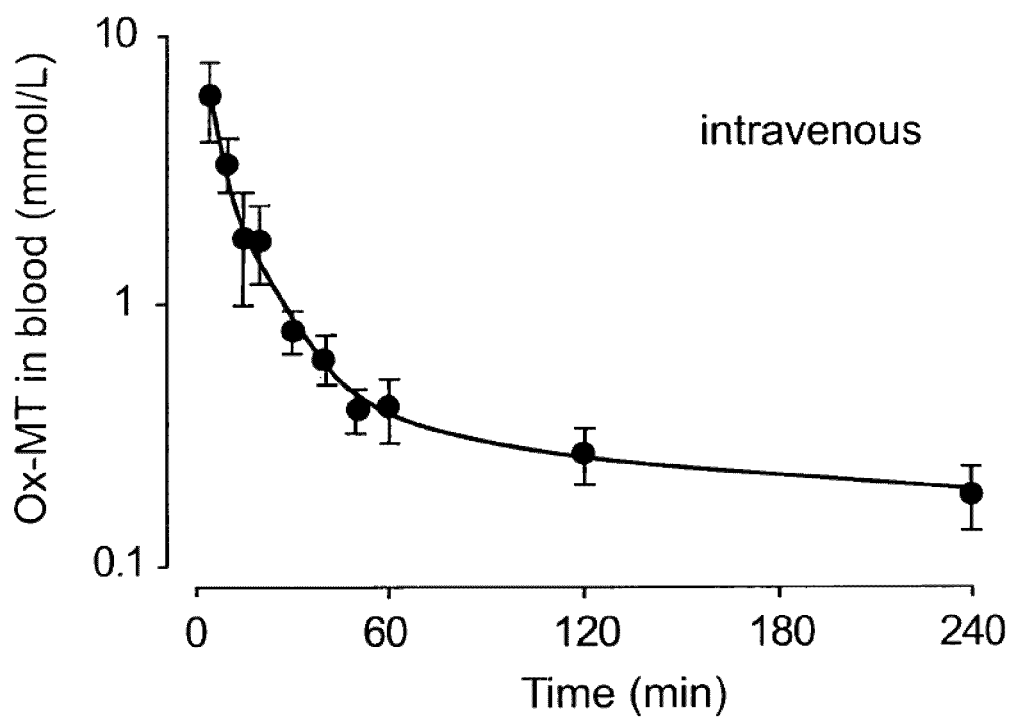

FIG. 14. Concentration of Ox-MT in whole blood after intravenous administration of 100 mg MTC (from Peter et al., 2000).

Figure 15:
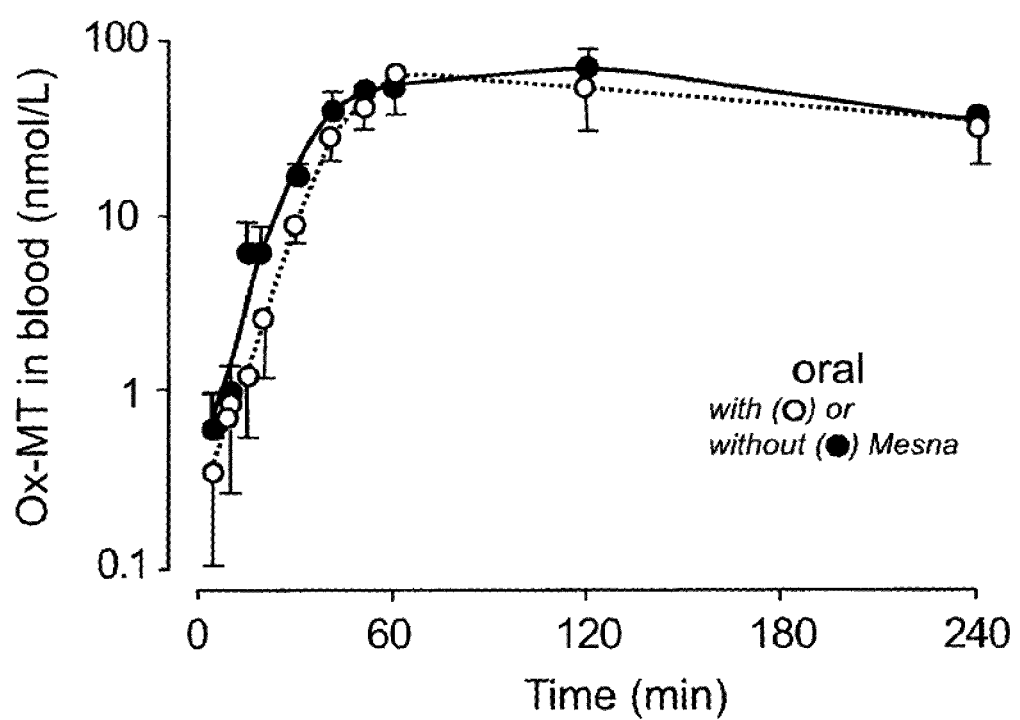

FIG. 15. Concentration of Ox-MT in whole blood after oral administration of 100 mg MTC with (open circles) or without (filled circles) 800 mg of Mesna (mean, SE) (from Peter et al., 2000).

Figure 16:
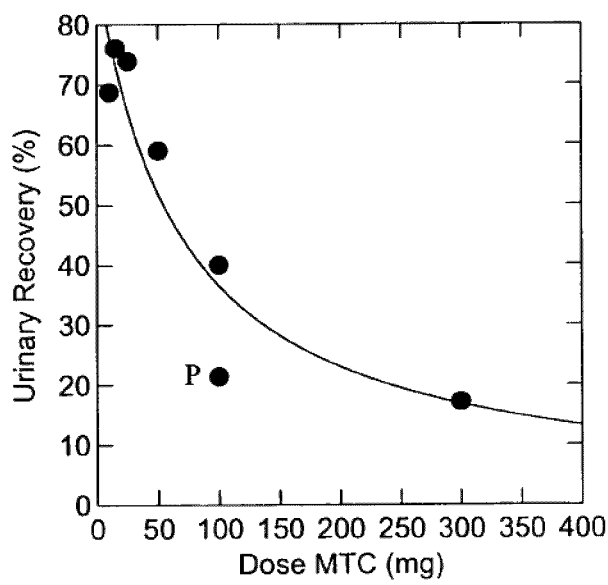

FIG. 16. Estimation of apparent bioavailability based on excretion of total-MT (i.e. Ox-MT+L-MT) at T-infinity following oral dosing, where the curve has been fitted by the empirical equation:

$$\text{Urinary recovery}=88.9-(88.9\times\text{Dose})/(69.7+\text{Dose})$$

Note the lower than expected value (marked "P") for the 100 mg dose result reported by Peter et al. (corrected for expected 48-hr excretion).

Figure 17:
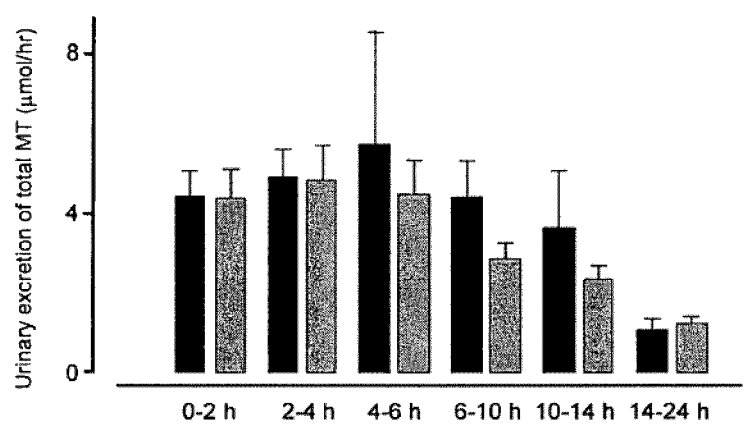

FIG. 17. Rate of urinary excretion of total MTC (µmol/h) during the indicated time intervals after i.v. (black bars) and oral (grey bars) administration of MTC. Mean, SE, n=7 (from Peter et al., 2000).

Figure 18:
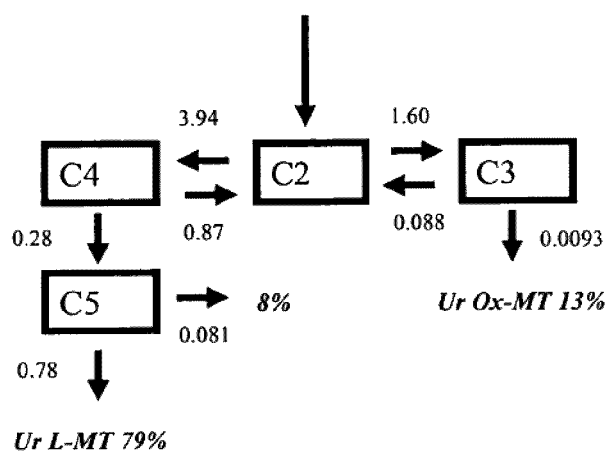

FIG. 18. First stage of model: fitting blood concentration data following single intravenous dose of 100 mg MTC and scaled urinary excretion data following single oral dose of 10 mg MTC.

Figure 19:
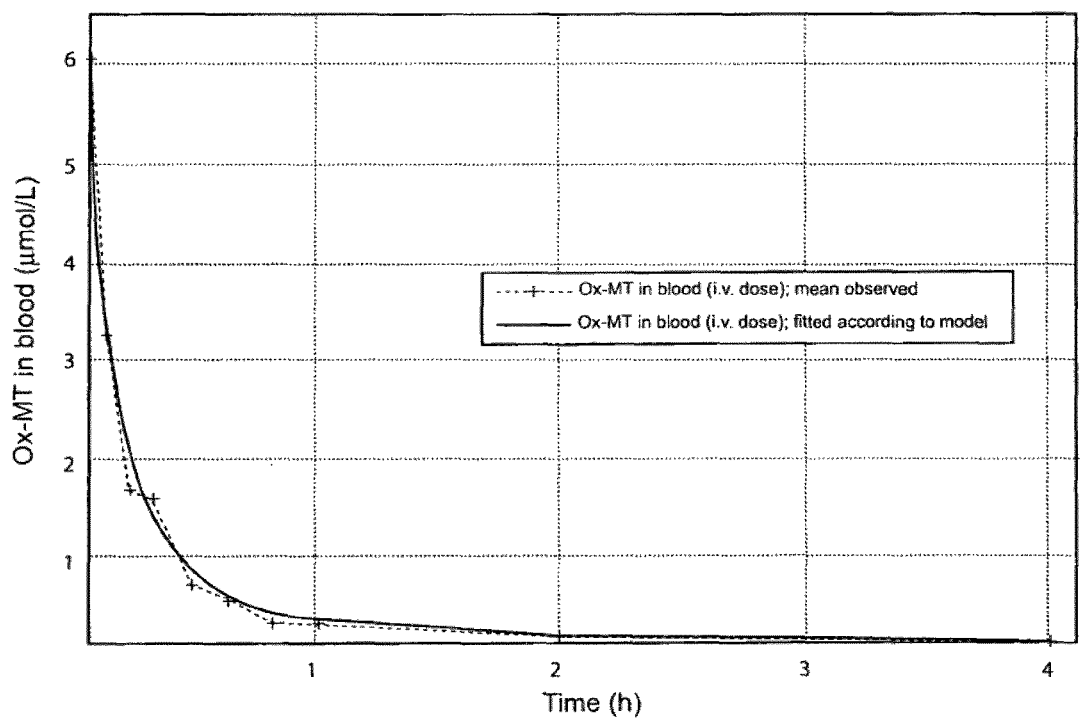

FIG. 19. Fit between observed blood concentration data following intravenous dosing from Peter et al. (Table 7) and prediction of the model depicted in FIG. 18.

Figure 20:
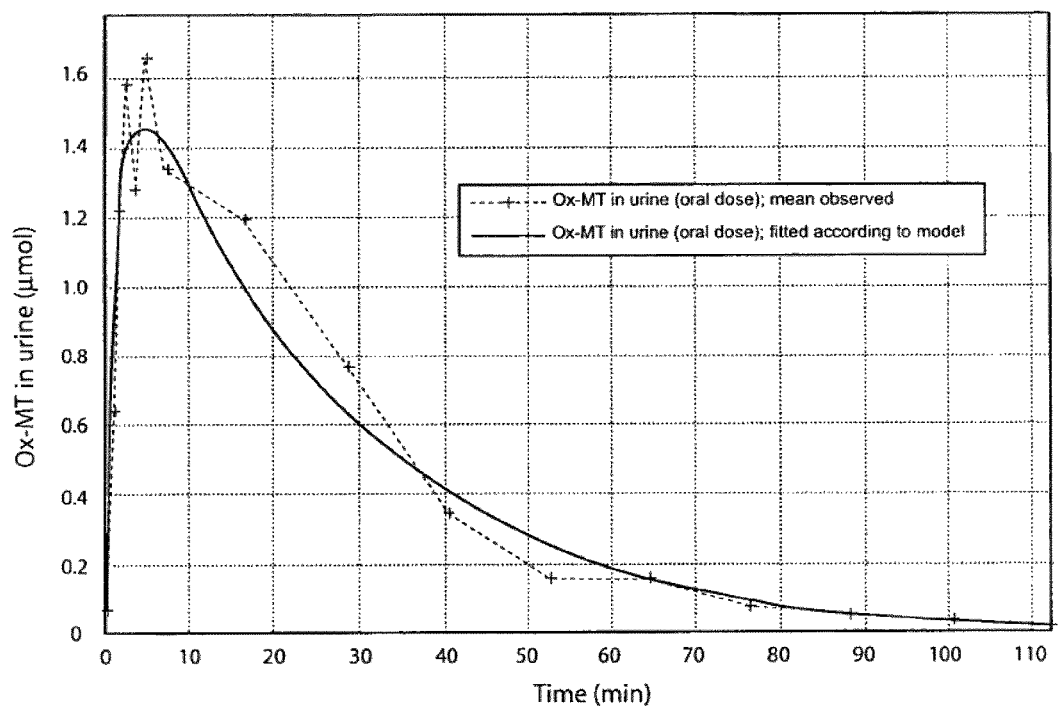

FIG. 20. Fit between scaled observed urinary excretion of Ox-MT following a single oral dose of 10 mg MTC from DiSanto and Wagner (Table 5) and prediction of the model (shown in FIG. 18) after single intravenous dose of MTC (100 mg).

Figure 21:
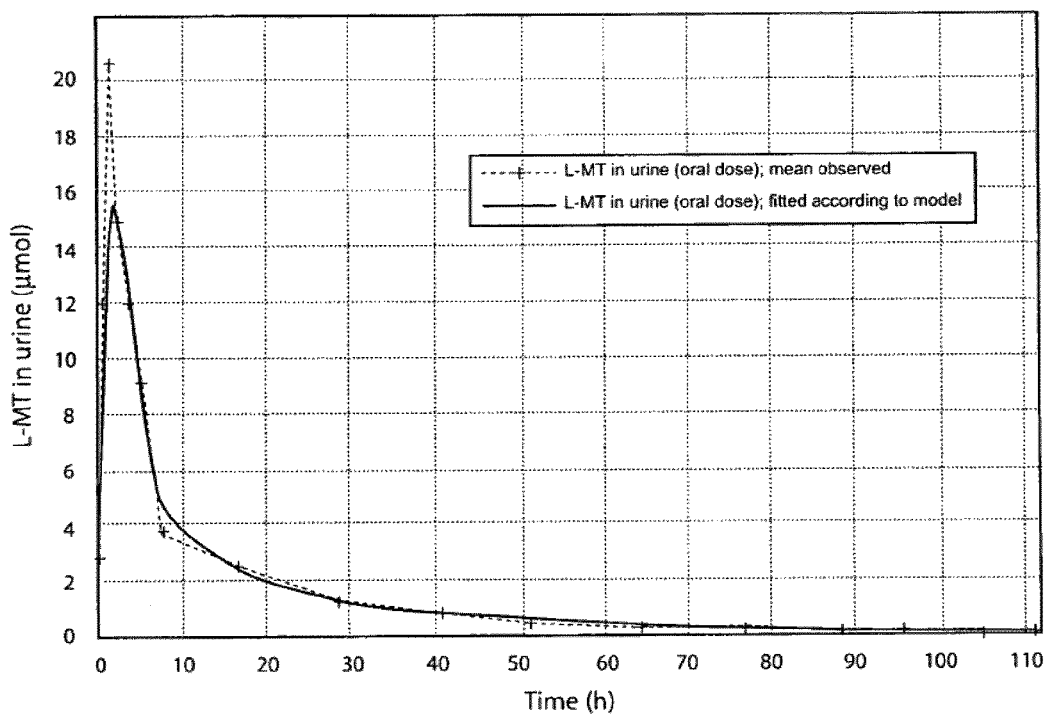

FIG. 21. Fit between scaled observed urinary excretion of L-MT following single oral dose of 10 mg MTC from DiSanto and Wagner (Table 5) and prediction of the model (shown in FIG. 18) after single intravenous dose of MTC (100 mg).

Figure 22:
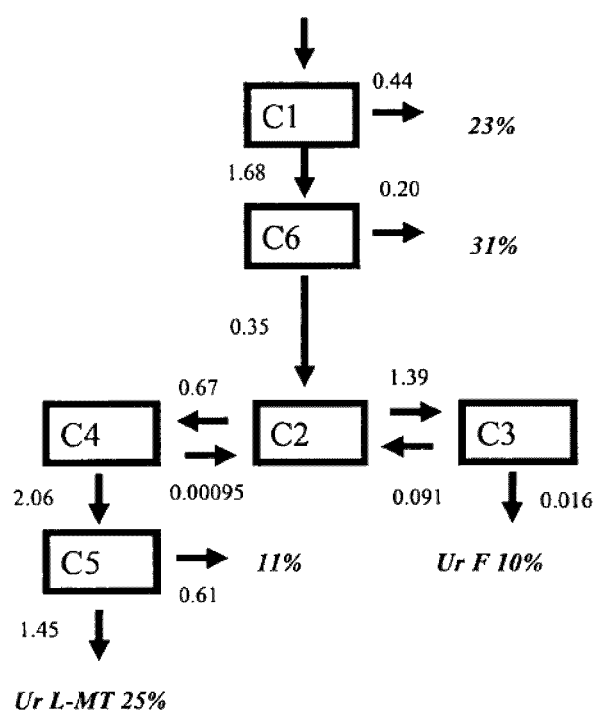

FIG. 22. Second stage of model: fitting blood concentration data following a single oral dose of 100 mg MTC and scaled urinary excretion data following a single oral dose of 10 mg MTC.

Figure 23:
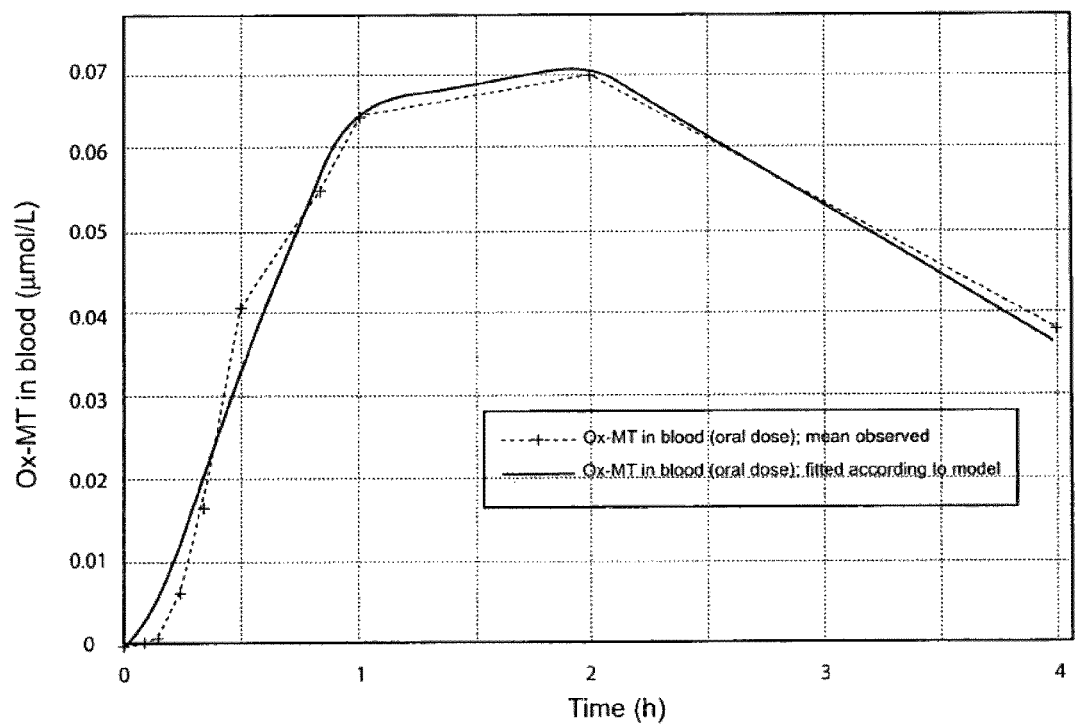

FIG. 23. Fit between observed blood concentration data following oral dosing from Peter et al. (Table 7) and prediction of the model depicted in FIG. 22.

Figure 24:
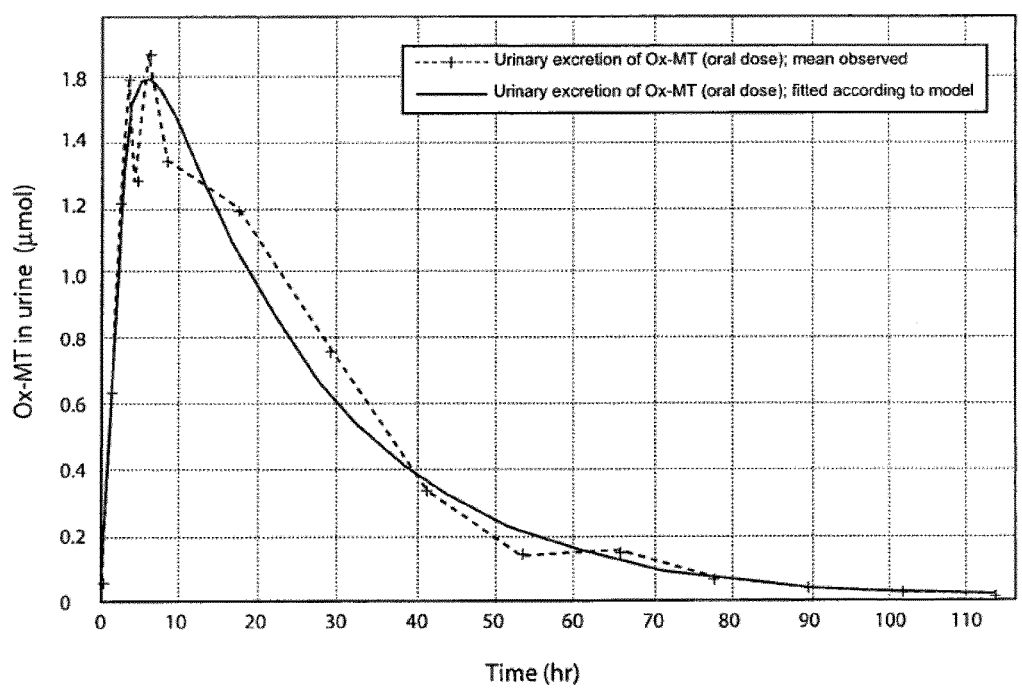

FIG. 24. Fit between scaled observed urinary excretion of Ox-MT following single oral dose of 10 mg MTC from DiSanto and Wagner (Table 5) and prediction of the model (shown in FIG. 22) after single oral dose of MTC (100 mg).

Figure 25:
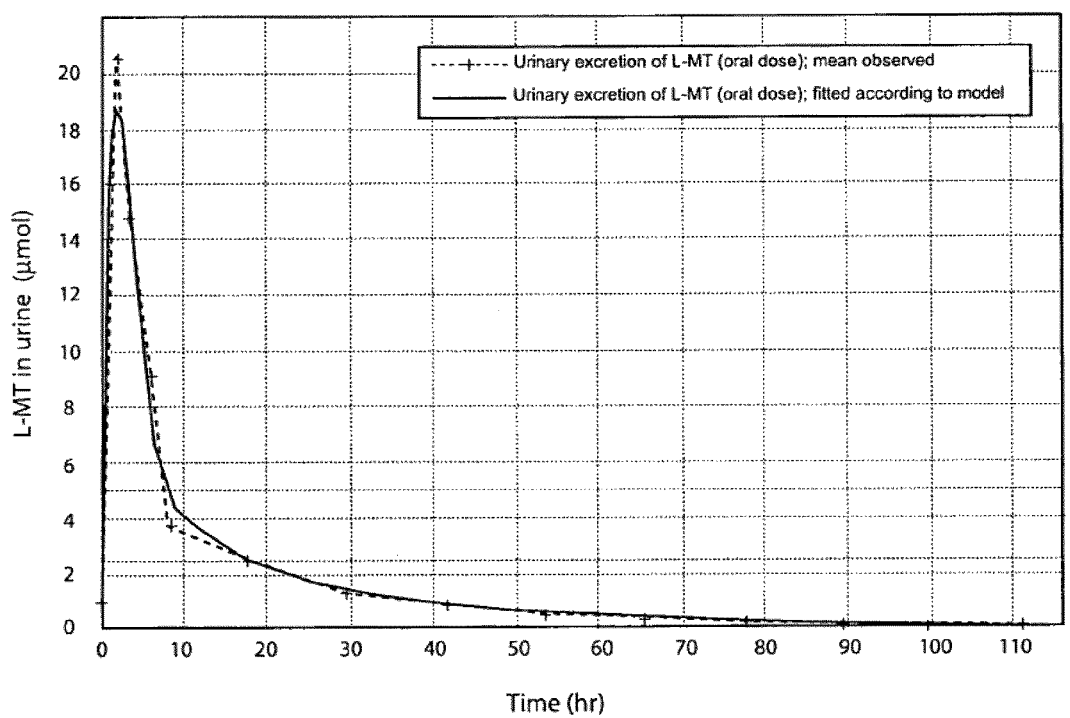

FIG. 25. Fit between scaled observed urinary excretion of L-MT following single oral dose of 10 mg MTC from DiSanto and Wagner (Table 5) and prediction of the model (shown in FIG. 22) after single oral dose of MTC (100 mg).

Figure 26:
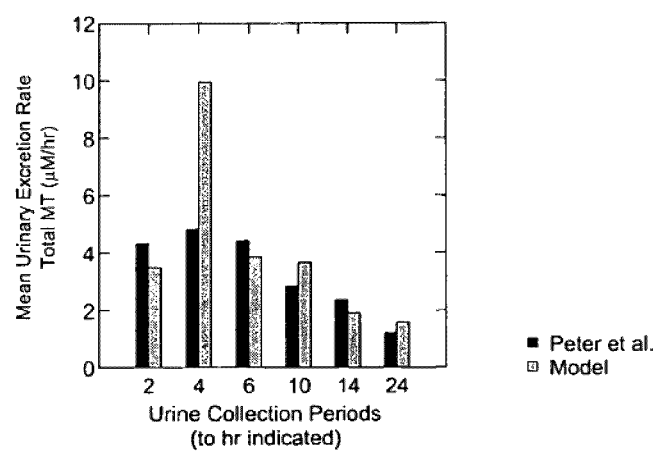

FIG. 26. Comparison of mean urinary excretion rates of total MT as reported by Peter et al. and those predicted by the oral model shown in FIG. 22 for the same intervals. Comparison of total excretion over 24 hr is shown.

Figure 27:
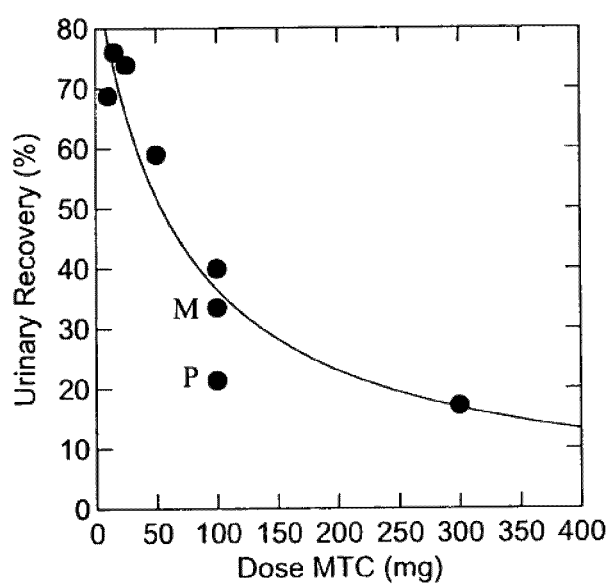

FIG. 27. This reproduces FIG. 16, but includes the model prediction ("M") for excretion of MTC. The model value is closer to that predicted from other studies than the estimate reported by Peter et al. ("P").

Figure 28:
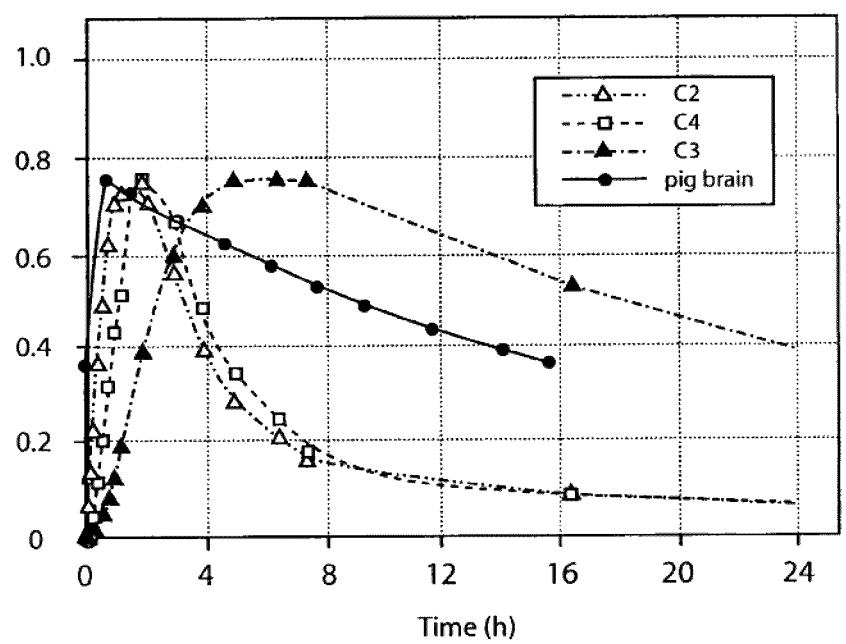

FIG. 28. Outputs of the oral model for C2 (blood), C4 and C3 are shown rescaled to their corresponding maxima. These are compared with a triexponential model applied to the measured level of MT in pig brain following a single oral dose.

Figure 29:
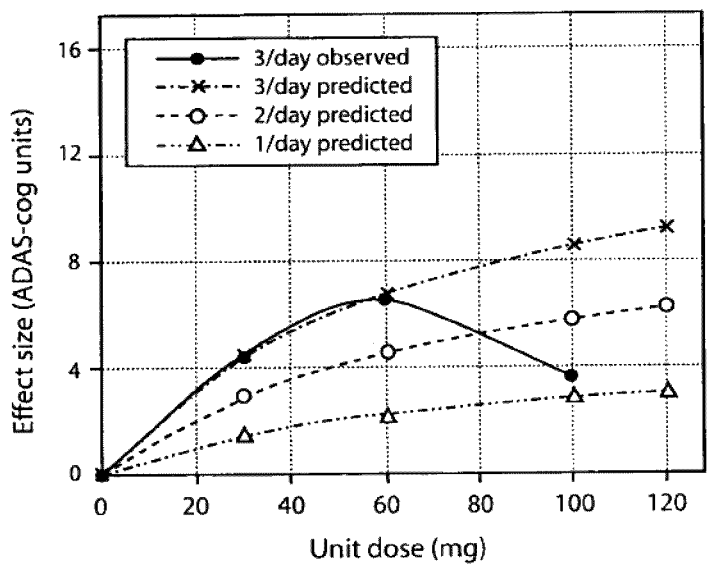

FIG. 29. Relationship between observed clinical efficacy of REMBER™ and predicted average steady state level of MT in C3 for the 3/day dosing regime. Also shown are the predicted steady state levels of MT in C3 for 2/day and 1/day dosing regimes.

Figure 30:
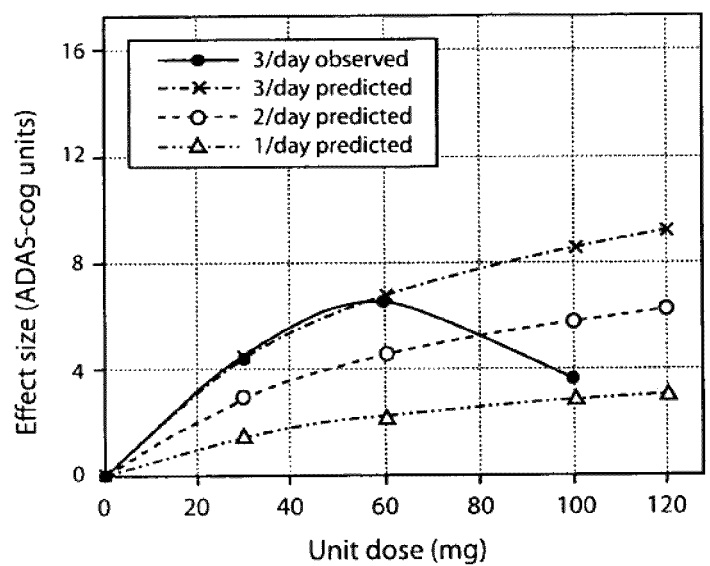

FIG. 30. Relationship between observed clinical efficacy of REMBER™ and predicted average steady state level of MT in C2 for the 3/day dosing regime. Also shown are the predicted steady state levels of MT in C2 for 2/day and 1/day dosing regimes.

Figure 31A:
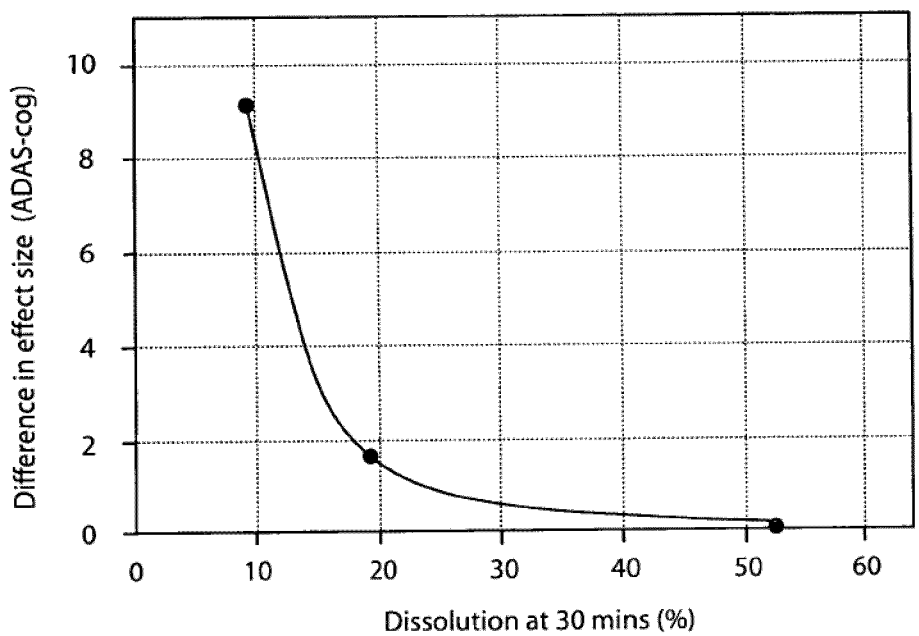

FIG. 31A. Difference between observed effect size and predicted effect size as a function of percent capsule dissolution at 30 minutes. Capsule dissolution is determined by the amount of MTC released into the aqueous phase in standard US/EU Pharmacopoeia dissolution conditions.

Figure 31B:
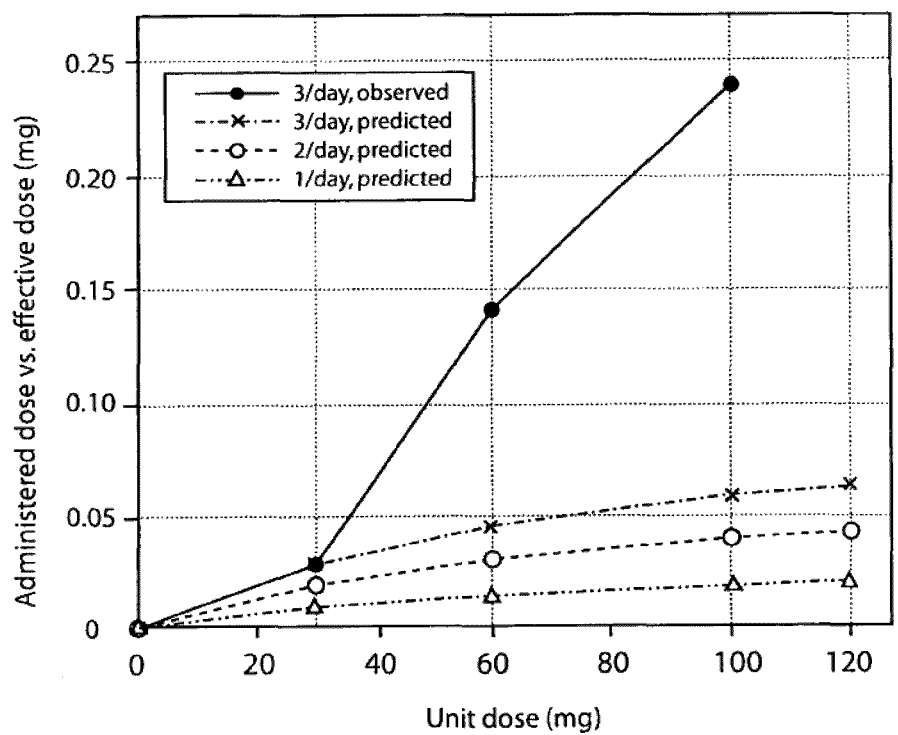

FIG. 31B. Relationship between expected steady-state level of MT in the central compartment (C2, i.e. blood) and observed loss of red cells at 24 expressed (expressed as fractional change relative to normal range).

Figure 32:
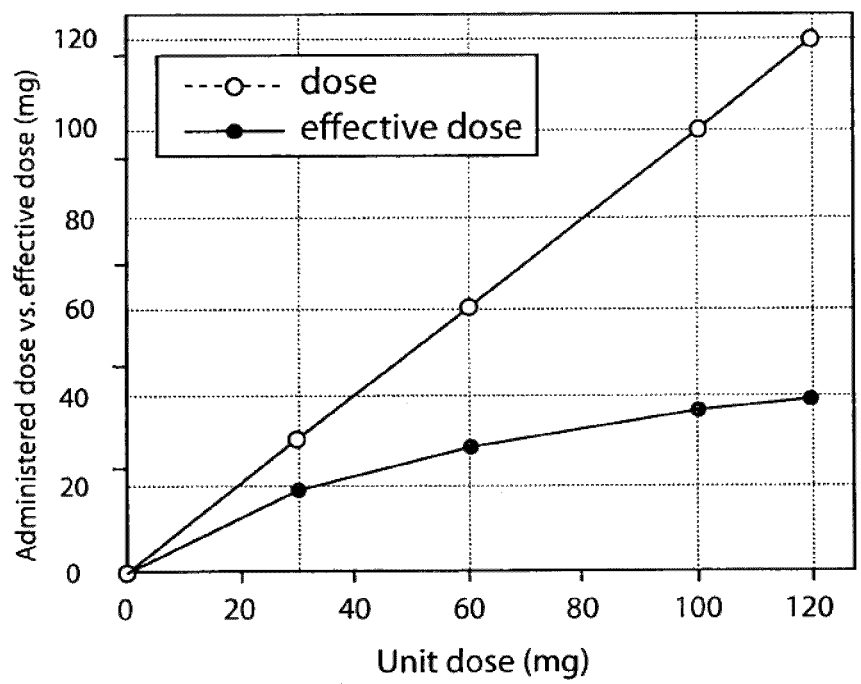

FIG. 32. Relationship between actual dose ("dose") and effective dose ("eff dose") based on urinary excretion data.

Figure 33:
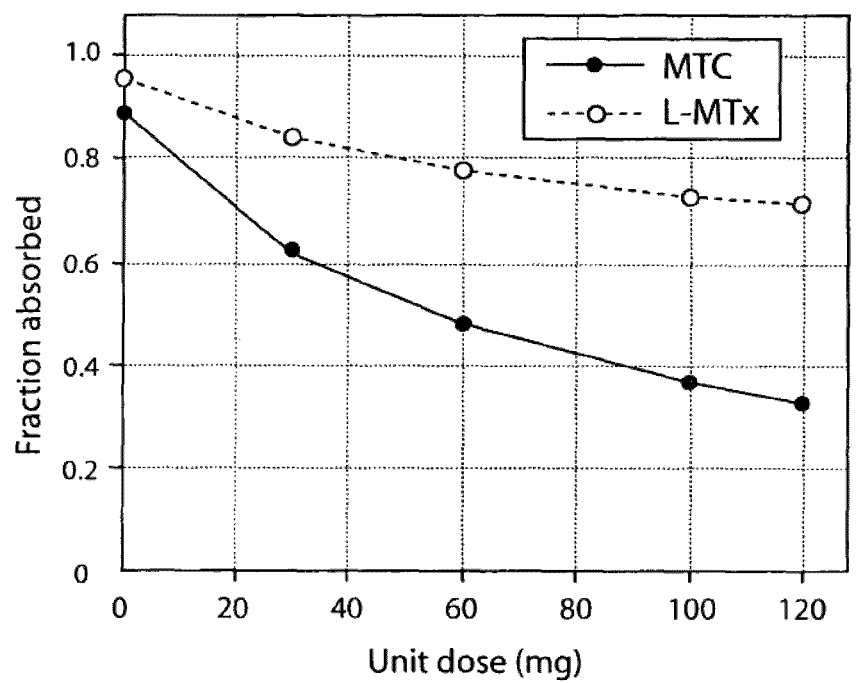

FIG. 33. Comparison of predicted fraction absorbed for MTC and L-MTx assuming that administration of the L-MTx form eliminates non-absorption from the stomach (ie C1 in FIG. 22).

Figure 34:
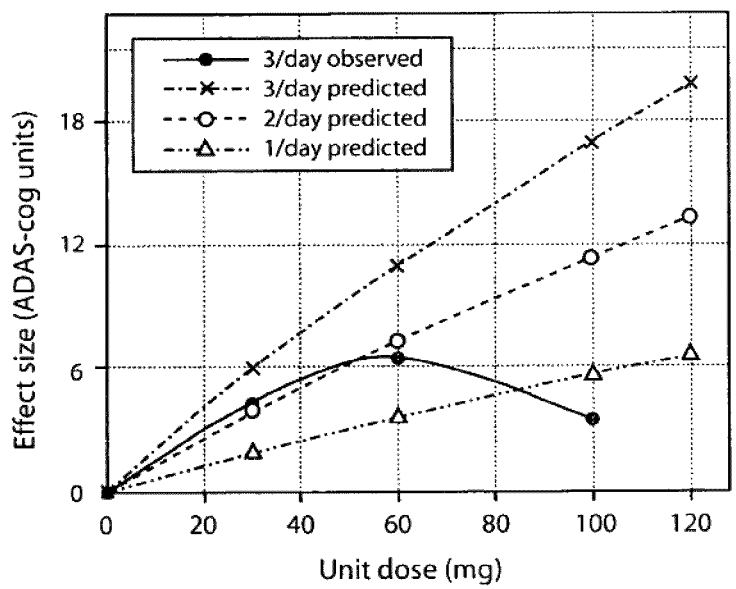

FIG. 34. Relationship between expected clinical efficacy of an L-MTx-based form of the methylthioninium moiety and predicted average steady state level of MT in C3 for a range of dosing regimes from 1/day to 3/day.

Figure 35:
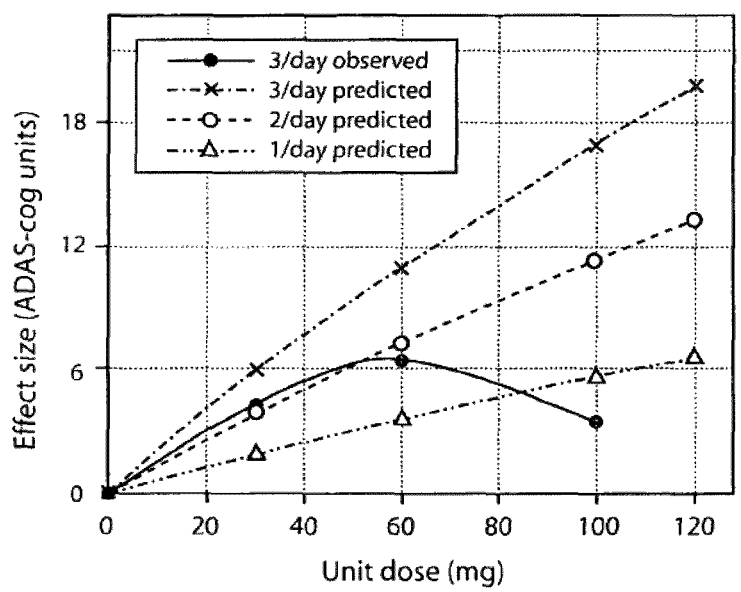

FIG. 35. Relationship between expected clinical efficacy of an L-MTx-based form of the methylthioninium moiety and predicted average steady state level of MT in C2 (blood) for a range of dosing regimes from 1/day to 3/day.

Figure 36:
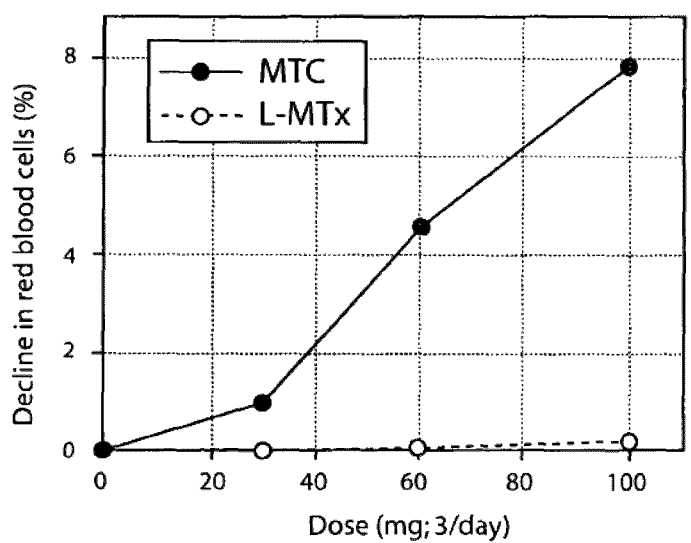

FIG. 36. Observed dose-response relationship for effect of MTC in the capsule formulation used in the trial TRx-014-001 on loss of red cells and for MTC-based and expected dose-response relationship for an L-MTx-based form of a methylthioninium medicinal product administered at the doses indicated at a frequency of 3/day.

FIG. 37A to 37I. Various quantitative models for the progression and treatment of Alzheimer's Disease as described in Example 12.

Figure 38:
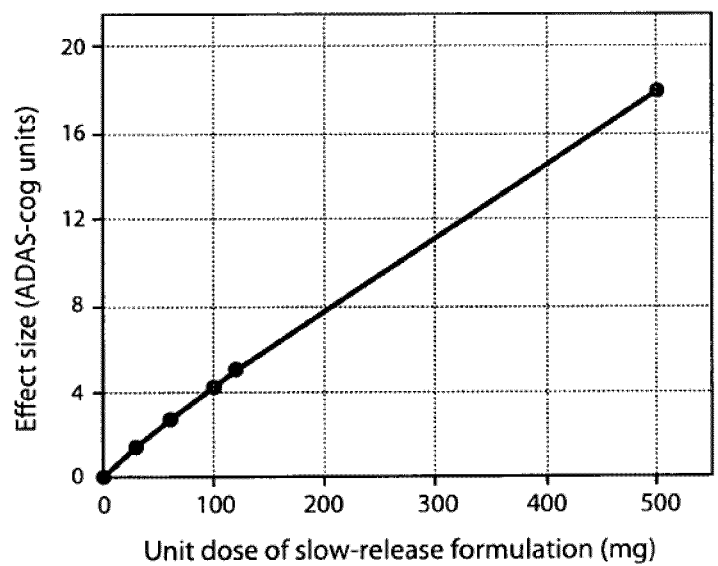

FIG. 38. Relationship between expected clinical efficacy of an L-MTx-based preparation for 1/day slow-release formulation.

Figure 39:
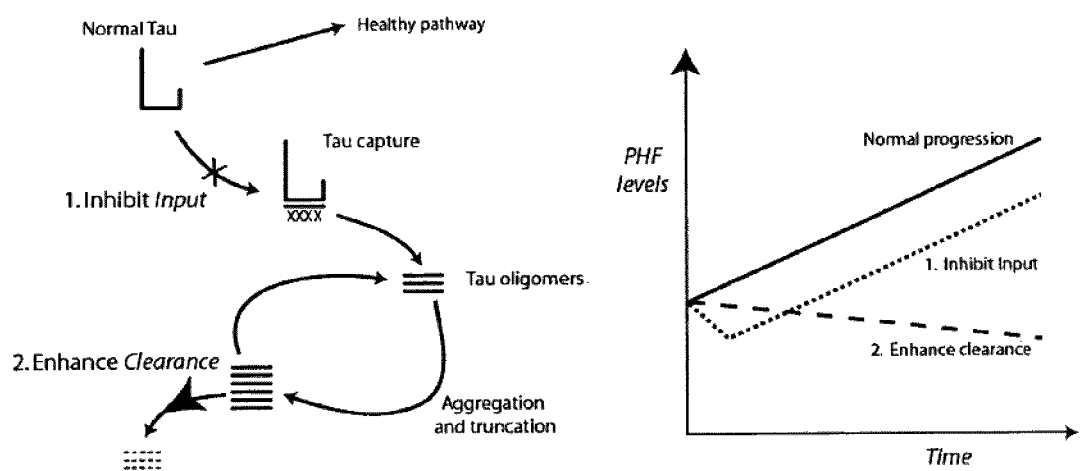

FIG. 39. The differential effect of inhibitors of different sites of the tau aggregation pathway. The scheme on the left shows the site of inhibition of tau entry into the tau aggregation pathway (input) and the site of enhanced clearance of tau aggregates from that pathway. The effect of changes at both of these two sites on PHF levels in neurons is shown in the right panel. Inhibition of input decreases the level of PHFs initially, before the rate of formation continues at the same level as before. Enhanced clearance of aggregated tau, however, results in a steady decrease in the level of aggregated tau.

Figure 40:
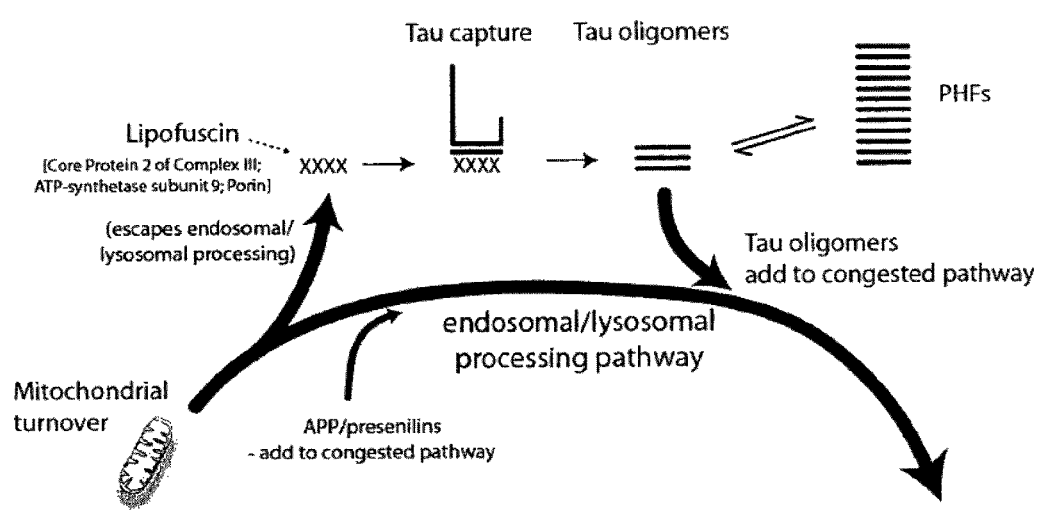

FIG. 40. Tau aggregation and its clearance in Alzheimer's disease. Tau oligomers can either assemble into filamentous PHFs and/or enter the endosomal-lysosomal clearance pathway.

EXAMPLES

Example 1—Phase 2 Clinical Trial TRx-014-001

Summary

Figure 1:
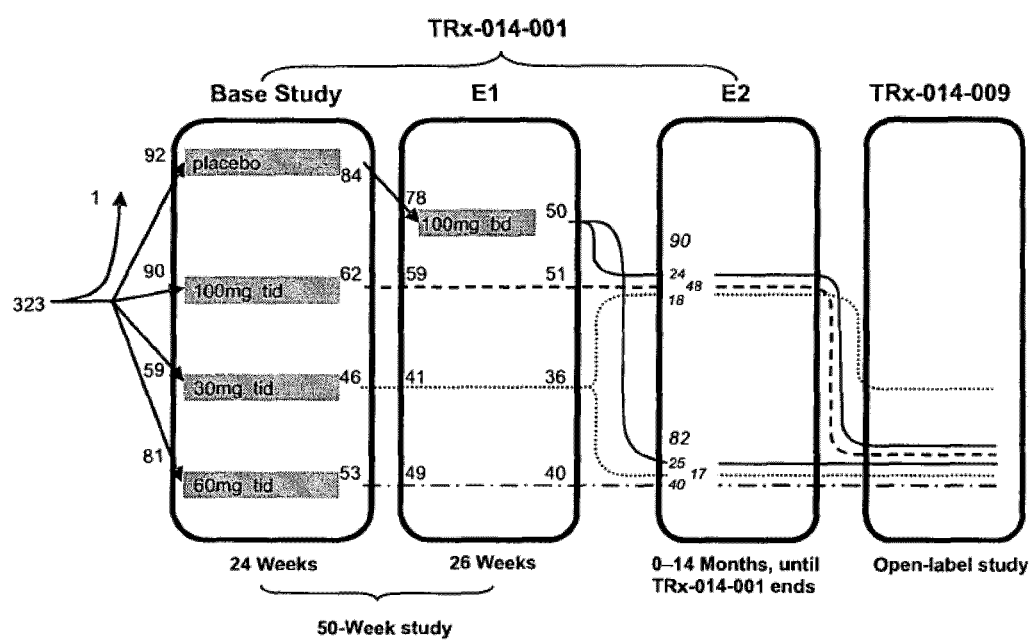
FIG. 1. TRx-014-001 & 009 clinical trial study design. The numbers correspond to the patients at each stage of the study. 323 patients entered the base study, one subject was randomised but not given medication. Subjects were treated with MTC as indicated or placebo. After 24 weeks and 50 weeks, subjects continued into 2 extensions (E1 and E2) of the trial and then continued in trial TRx-014-009. For ethical reasons, those on placebo for the first 24 weeks were given 100 mg bd in E1. "tid" means dosing at a frequency of three times per day, and "bd" means dosing at a frequency of twice per day.

A 50-week Phase 2 exploratory dose-range-finding study for treatment of mild and moderate dementia of the Alzheimer type has been conducted using an investigational medicinal product (IMP) of which MTC was the active pharmaceutical ingredient (API). The study was a randomized, double blinded, placebo-controlled study whose primary objective was to investigate the effects of MTC at three doses (30, 60 and 100 mg, each three times per day) compared with placebo on cognitive ability (as measured by the ADAS-cog scale: Alzheimer's Disease Assessment Scale—cognitive subscale). There were 322 subjects randomized, of whom 245 (74%) completed the first 24 weeks of treatment. Of these, 227 (93%) chose to continue treatment for a further 6 months, of whom 177 (78%) completed 50 weeks of treatment on 2 Jul. 2007. The final analyses comprise analyses of the ITT/OC (Intention to Treat/Observed Case) population of 245 subjects who completed 24 weeks of treatment, and 177 subjects who completed 50 weeks of treatment by 2 Jul. 2007. The study design is summarized in FIG. 1. For reasons of ethical concerns, subjects who were originally randomized to placebo during the first 6-month phase were switched to the 100 mg dose during the second 6-month extension phase of the study ("E1").

24-Week Analyses

The primary pre-specified outcome was an ITT/OC analysis of ADAS-cog change from baseline at 24 weeks using an analysis of covariance approach which included an assessment of the interaction between the effect of treatment with REMBER™ and baseline severity as defined by CDR (Clinical Dementia Rating scale). This analysis demonstrated a positive effect of REMBER™ at 60 mg tid which achieved statistical significance in both the ITT/OC and ITT/LOCF (Intention to Treat/Last Observation Carried Forward) populations. CDR severity at baseline was found to be a highly significant cofactor, and when included in the model showed that the effect of REMBER™ was significant at 24 weeks only in subjects who were CDR-moderate at baseline. The lack of decline in CDR-mild subjects on placebo prevented efficacy analysis in this group over the first 24 weeks. However REMBER™'s efficacy was confirmed in this group by functional brain scan analysis at 24 weeks, and by ADAS-cog at 50-weeks.

TABLE 1

ADAS-cog effect size at 24 weeks in CDR-moderates (in ADAS-cog units)

| Dose[1] | Estimate | 95% CI | p-value[2] |
|---|---|---|---|
| low (100 mg) | −0.42 | −4.24, 3.40 | 0.826 |
| 30 mg | −4.02 | −7.30, −0.74 | 0.0172 |
| 60 mg | −5.41 | −9.31, −1.52 | 0.0073 |

[1]The 100 mg dose is referred to as the "low(100 mg)" dose to indicate that in its present formulation, the therapeutic efficacy of the 100 mg capsule did not correspond to the nominal dose.
[2]The p-value is from a test of whether the value is significantly different from placebo.

Figure 2:
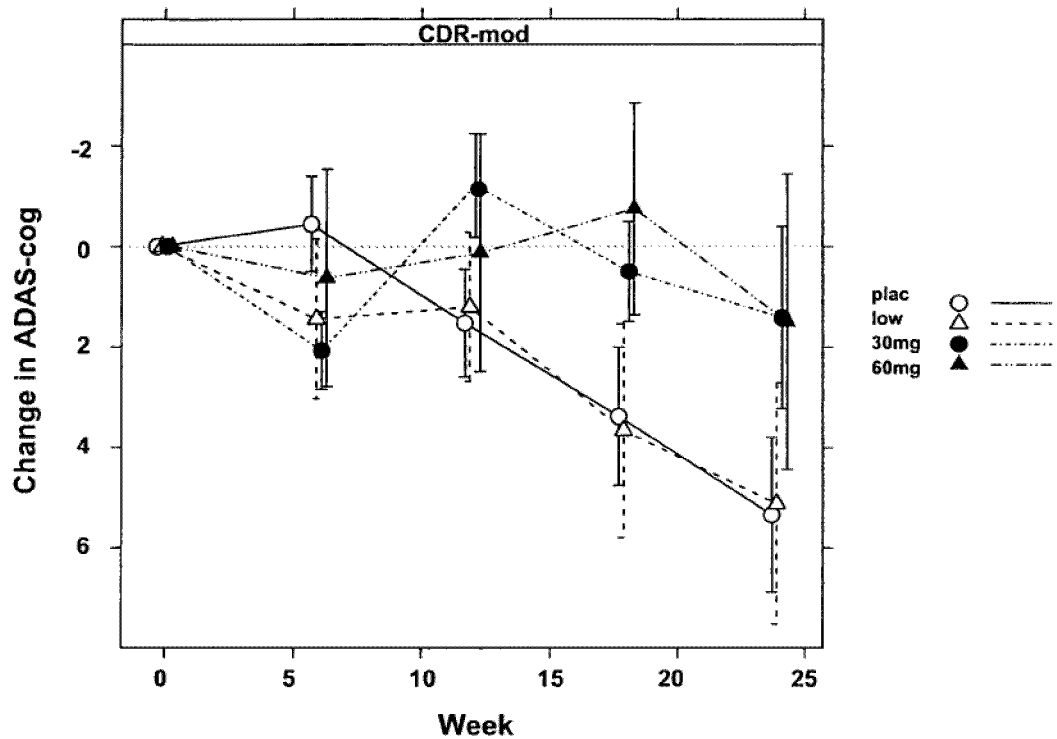
FIG. 2. Treatment response in CDR-moderates at 24 weeks. For this chart, the labelling conventions of "plac" refers to placebo, "low" refers to low (100 mg) (see footnote 1, Table 1) "30 mg" refers to 30 mg dose tid and "60 mg" refers to 60 mg dose tid.

In the analysis of the subgroup of the ITT/OC population who were CDR-moderate at baseline (FIG. 2), the effect size of REMBER™ at the 60 mg tid dose was −5.4 ADAS-cog units and 3.4 MMSE (Mini-Mental State Examination) units (MMSE data not shown). Whereas placebo-treated subjects declined by 5.1 ADAS-cog units, there was no evidence of decline in subjects treated with REMBER™ at 30 mg or 60 mg tid over 24 weeks. Non-cognitive outcome variables (measuring psychiatric disturbance and activities of daily living skills) also confirmed the disease-stabilising properties and efficacy size of REMBER™ in the moderate group. Subjects receiving REMBER™ at the 60 mg tid dose, showed an effect size of 1.4-1.9 units on the CGIC (Clinical Global Impression of Change) scale at 24 weeks relative to placebo, registered by clinical assessors blinded to the other outcome measures. The odds-ratio of not declining on CGIC for subjects taking REMBER™ at the 60 mg dose was 9 times better than placebo. The CDR-sum-of-boxes parameter, another global clinical measure, showed benefit of −1.7 units. Finally, REMBER™ at the 60 mg dose showed significant benefit on the ADFACS (Alzheimer's Disease Functional Assessment Scale) measure of activities of daily living, with an effect size of 3.1 to 6.1 units over 24 weeks. In all the psychometric analyses at 24 weeks, the 100 mg capsule showed minimal efficacy, consistent with a formulation defect of the capsules at this dosage strength discussed further below.

The 100 mg dose is referred to as the "low (100 mg)" dose to indicate that in its present formulation, the therapeutic efficacy of the 100 mg capsule did not correspond to the nominal dose. This is discussed in more detail in the Examples below.

Functional Brain Scan Analysis

Figure 3:
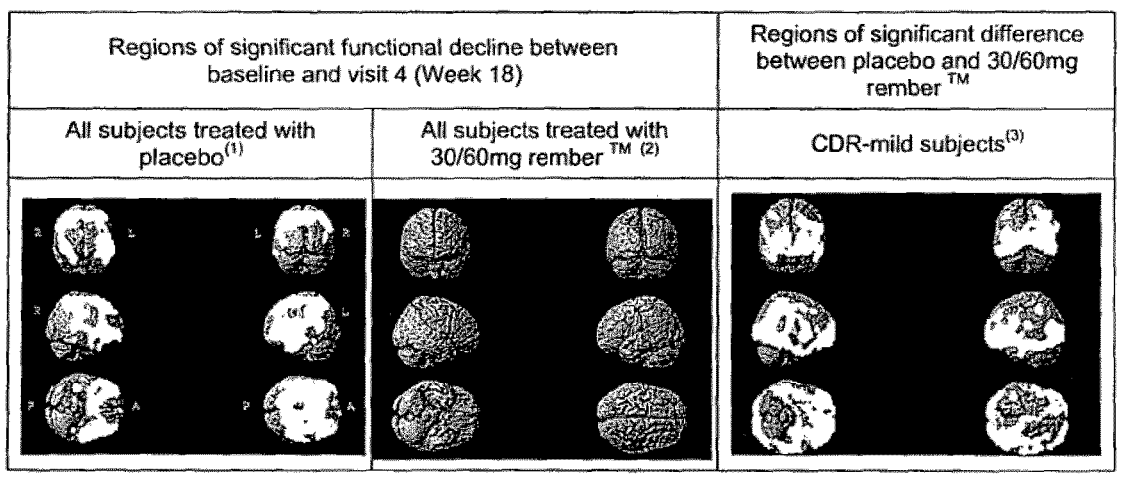
FIG. 3. Comparison of treatment effects of REMBER™ as seen by functional brain imaging using SPECT. Decreased regional cerebral blood flow (rCBF) is seen as areas of white across the brain.

Prevention of decline over 24 weeks was independently confirmed by analysis of functional brain scan changes in 135 subjects who had undergone two SPECT scans 6 months apart on average (FIG. 3). Whereas subjects receiving placebo showed the expected pattern of deterioration in frontal and temporo-parietal regions of the brain, subjects receiving REMBER™ at 30 mg or 60 mg showed no evidence of deterioration in any brain region. When the subgroup who were CDR-mild at baseline were examined separately, there was also evidence of prominent decline over 6 months in subjects receiving placebo, amounting to loss of 8% of functioning neuronal volume. The treatment effect seen in the whole population was also seen in the CDR-mild subgroup, demonstrating the efficacy of REMBER™ in CDR-mild AD. The fact that there was objective evidence of progressive functional deterioration in the mild subgroup without corresponding evidence of decline on any of the psychometric scales over 6 months confirms the powerful confounding influence of cognitive reserve in mild AD. Overall, despite this effect, baseline functional deficits shown by SPECT scan were highly correlated with baseline ADAS-cog score, and the benefit of treatment with REMBER™ shown on the ADAS-cog scale was likewise correlated with the functional benefit demonstrated by SPECT scan. REMBER™'S action seen by functional brain scan strongly suggests that REMBER™'S ability to reverse the Tau aggregation pathology, which is known to occur in the same brain regions as those showing functional brain scan defects, is responsible for its ability to prevent decline in cortical brain function in the same regions. Given the greater sensitivity of SPECT in detection of both decline and treatment effects, and its ability to predict treatment response (see 50-week analysis below), it is concluded that SPECT could be used as a surrogate or proxy marker for future clinical trials aiming to demonstrate disease modification.

50-Week Analyses

The 50-week study extended and confirmed the findings of the 24-week study, and demonstrated significant benefits in both CDR-mild and CDR-moderate subjects in the overall ITT/OC and ITT/LOCF populations (FIG. 4; Tables 2 and 3). Subjects originally randomized to placebo were switched to the low (100 mg) dose bd after 24 weeks. This is referred to as the "placebo-low" treatment arm. Because of the minimal efficacy of the low (100 mg) dose on any of the psychometric scales over the first 24 weeks of treatment, the placebo-low treatment arm conveniently served as the Least Exposed Dose comparator arm for the 50-week study.

The mean decline observed over the 50-week study in placebo-treated subjects was 7.8 ADAS-cog units (FIG. 4). For subjects treated with REMBER™ at a dose of 60 mg tid, the decline seen over 50 weeks was not significantly different from zero on either the ADAS-cog scale or the MMSE scale for subjects. On the ADAS-cog scale, about 60% of subjects improved or stayed the same at 50 weeks. On the MMSE scale, 62% improved or stayed the same at 50 weeks. The odds of a patient not declining on either scale were about 3.4 times better at the 60 mg dose than on placebo-low. The corresponding effect sizes were −6.8 ADAS-cog units and 3.2 MMSE units over the 50-week trial. In addition to the effect on disease progression, there was an initial symptomatic improvement at 15 weeks of 1.6 ADAS-cog units and 0.8 MMSE units at the 60 mg dose, comparable to that observed with AChE inhibitors.

TABLE 2

Effect sizes inferred from mixed effects analysis at 50 weeks (in ADAS-cog units)

| Dose | Estimate | 95% CI | p-value[1] |
|---|---|---|---|
| low (100 mg) | −4.04 | −7.21, −0.87 | 0.0124 |
| 30 mg | −3.87 | −6.90, −0.84 | 0.0126 |
| 60 mg | −6.78 | −9.74, −3.82 | <0.0001 |

[1]The p-value is from a test of whether the value is significantly different from placebo.

TABLE 3

Effect sizes inferred from least-squares analysis at 50 weeks (in ADAS-cog units)

| Dose | Estimate | 95% CI | p-value[1] |
|---|---|---|---|
| low (100 mg) | −3.59 | −5.81, −1.37 | 0.0015 |
| 30 mg | −4.37 | −6.83, −1.92 | 0.0005 |
| 60 mg | −6.50 | −8.89, −4.14 | <0.0001 |

[1]The p-value is from a test of whether the value is significantly different from placebo.

There was no deterioration on the non-cognitive scales in CDR-mild subjects in the placebo-low arm over 50 weeks.

The non-cognitive outcomes at 50 weeks in CDR-moderate subjects confirmed the findings of the 24-week analyses. The NPI (Neuropsychiatric Inventory) demonstrated benefits for REMBER™ treatment over 50 weeks. Whereas subjects in the placebo-low arm declined by 9.6 units on the patient-disturbance scale and 4.9 units on the carer-distress scale, no such decline was seen in subjects continuously treated with REMBER™ over 50 weeks, with corresponding best effect sizes of −9.2 units and −4.6 units.

The placebo-low arm compared to the low (100 mg) arm provided a close approximation to a delayed start design to confirm that REMBER™ is disease modifying in a formal regulatory sense. Subjects who began later on a dose of minimal apparent therapeutic efficacy as judged by ADAS-cog over the initial 24 weeks remained significantly different at 50 weeks relative to subjects who had been receiving the low (100 mg) dose continuously. Furthermore subjects treated continuously at the low (100 mg) dose showed retardation in the rate of disease progression. Although there was a difference in the capsule dosage regime between the two arms (tid vs. bd), haematological side effects, which showed a clear dose-response profile, were indistinguishable with regard to the two dosing regimes, supporting the approximate equivalence of biological exposure, and hence supporting the inference that REMBER™ is disease-modifying. This is also confirmed by REMBER™'s ability to arrest disease progression over 50 weeks at the 60 mg dose, and reduced the rate of disease progression at the 30 mg and low (100 mg) doses at 50 weeks.

Summary of Clinical Safety of REMBER™

The overall adverse event profile was substantially better in the REMBER™ trial than for AChE (Acetylcholine Esterase) inhibitors at optimal treatment dose reported in the Cochrane Review (Birks, 2006). There were no significant differences in the odds of subjects taking REMBER™ at 30 mg or 60 mg tid withdrawing, experiencing any adverse event or withdrawing due to an adverse event, compared with AChE inhibitors. Diarrhoea was the most frequent adverse event reported by subjects treated with REMBER™, particularly the low (100 mg) dose, most likely due to transit of non-absorbed REMBER™ to the distal bowel, causing repopulation of gut flora due to a mild antibiotic activity of MTC which has been well documented in literature (Kristiansen and Amaral, 1997; Gunics et al., 2000). Although subjects receiving REMBER™ had higher odds of developing diarrhoea than reported for AChE inhibitors, subjects taking REMBER™ reported significantly less nausea, vomiting, anorexia and abdominal pain, headache, fatigue and agitation. The experience from some of the trial centres indicated that diarrhoea may be managed with suitable probiotic preparations (eg dried *lactobacillus* preparation).

No changes of clinical significance were seen in any of the routine clinical chemistry parameters. Small reductions in red-cell counts, haemoglobin, methaemoglobin and white-cell counts were seen in subjects treated with REMBER™, and these changes were dose-related. The changes were negligible for the 30 mg tid dose, but became statistically significant for the 60 mg and low (100 mg) tid doses. In the case of red-cell parameters, they appeared over 24 weeks, but resolved over 50 weeks, except for evidence that the 60 mg tid dose increased methaemoglobin levels at 24 weeks and stabilized thereafter. At this dose, the mean level of methaemoglobin increased from the normal mean value of 0.4% to 0.8% of haemoglobin, but still below the upper limit of normal (1%). In the case of white-cells, again the changes were negligible for the 30 mg tid dose, but for the 60 mg dose values decreased and then stabilized at levels not significantly different from the 30 mg dose over 50 weeks. It is concluded that oxidation of haemoglobin by an oxidised form of the methylthioninium moiety is the most likely mechanism responsible for changes in the red cell parameters.

Within the period of the study, none of these changes was clinically significant, and all remained well within the normal range. Therefore, it is concluded that the changes do not cause sufficient concern in terms of risk/benefit ratio to impact on the further clinical development of the 30 mg and 60 mg dosage strengths. The present formulation of the low (100 mg) dose is not suitable for further clinical development because of a poorer efficacy/side-effect profile discussed below.

Example 2—Formulation and Strength of the Investigational Medicinal Product (IMP)

The formulation of REMBER™ used in TRx-014-001 consisted of Size 1 blue/blue gelatin capsules containing a semisolid fill comprised of MTC, Gelucire 44/14 and Aerosil 200. Three strengths of capsule, differing only in fill weight, were manufactured with target strengths 30, 60 and 100 mg of MTC, respectively. A matching placebo containing only Gelucire 44/14 was provided. The hard gelatin capsules and the gelatin used for capsule banding complied with current guidelines regarding Transmissible Spongiform Encephalopathies.

Uniformity of capsules was tested by Appearance, Fill Weight Uniformity, Assay (modified from USP 27), Chromatographic purity (TLC as specified by USP 27) and Dissolution using the European Pharmacopoeia and US Pharmacopoeia rotating paddle method. Six manufacturing lots of capsules were produced, and were tested for uniformity and stability.

Through these dissolution studies, it was found that the dissolution of the 100 mg capsule in all in vitro conditions was slower than the 30 mg capsule and that this difference increased over time since manufacture (FIG. 5). The 60 mg capsule had an intermediate dissolution profile relative to the 30 mg and 100 mg data shown in FIG. 5. Further studies have shown that accelerated cross-linking of the gelatine capsules in the presence of MTC at high fill-weights (i.e., particularly 100 mg capsules) decreased the probability of initial capsule breach, although subsequent dissolution from the breached capsule was rapid. The MTC released from the capsule was found to retain the expected level of bio-activity in the in vitro Tau aggregation assay (WO96/030766).

This delay in dissolution of the 100 mg capsule is likely to have shifted the primary site of absorption from the stomach to the small intestine, leading both to reduced absorption (leading to diarrhoea) and absorption of the majority of the bioavailable dose as a therapeutically inactive dimeric species. The implied dose-response relationship discussed further below indicates that in the present formulation, the equivalent cognitively-active dose available from the 100 mg capsule was ~25 mg, when compared with the cognitive activities of the 30 mg and 60 mg doses.

The present formulation limits the extent to which higher doses of REMBER™ can be explored clinically in future clinical studies. As discussed further below, there is no theoretical basis for an efficacy plateau at the 60 mg dose. It is concluded that the apparent plateau at 60 mg tid reflects a combination of limitations in solubility, dissolution and absorption of REMBER™ at higher dose.

Example 3—Mathematical Efficacy Model

A kinetic mathematical model has been developed to try to gain a better understanding of the Tau aggregation process and its quantitative relationship with cognitive deterioration. The structure of the model is illustrated below in FIG. 6, showing the relevant rate constants.

A broad range of experimental data inputs were used to derive estimates of the key rate constants in the above model. These included inter alia: quantitative clinico-pathological studies linking Tau aggregation and MMSE score in man, estimation of rate of progression of Braak stages over time (Braak and Braak, 1991), drug dose-response relationship in cell models and in the Tau binding assay in vitro, drug dose-response relationship in reduction of Tau pathology in transgenic animals, and a pharmacokinetic model linking dose to estimated available brain levels of REMBER™ in animals and in man discussed further below.

The clinical trial data were used to validate this efficacy model which can in turn explain the relationships between Tau aggregation, clinical dementia and REMBER™'s clinical efficacy profile. Specifically, no further assumptions implicating the accumulation of β-amyloid protein or other unknown neurotransmitter factors are formally required. It is surprising, given the complexity of the pathophysiology of AD generally assumed in the field, that an extremely parsimonious set of assumptions and rate constants can provide the entire basis for a set of formally definable relationships linking the rate of progression of clinical dementia, the dynamics of the Tau aggregation cascade illustrated above and the efficacy of Tau-aggregation inhibitor therapeutic intervention.

There are important inferences to be drawn from the model in explaining REMBER™'s mechanism of action. While it appears a priori, and it is generally assumed in the field, that the inhibition of the rate of Tau aggregation via the reduction in the rate of k3 (i.e. inhibition on the input side), would be important to explain efficacy, this is not borne out by the mathematical model. The model can be used to show that the impact of a theoretical drug that acts only on the inflow side of the aggregation cascade (e.g. strategies to reduce the upstream feed of products into the stage of aggregated Tau) would produce only a step-wise transient reduction in Tau aggregation which would be compensated for over time by continuing aggregation. In other words, the theoretical impact of such a drug would be only symptomatic and would not alter the rate of progression of the disease, even though the mechanism appears to be potentially disease-modifying because it targets primary pathology. The model shows that there would still be progressive accumulation of Tau aggregates over time, and at the same rate as without the drug. This is primarily because the clearance pathway for the Tau aggregates remains ineffective in an AD subject and deteriorates over time at a rate which can be measured by the rate of Braak stage progression over time. In the case of potential anti-Tau strategies, this applies particularly to approaches that might be based on inhibition of Tau phosphorylation, even if Tau phosphorylation were assumed to be rate-critical for Tau aggregation, which has been disputed by the inventors (e.g. Wischik et al., 1997). This further applies to arguments based on the rate at which β-amyloid protein might, in some as yet unknown manner, trigger Tau aggregation, as asserted by the recent current versions of the Aβ theory of AD pathogenesis (e.g. Selkoe, 2004).

The most important therapeutic action of REMBER™ lies in its ability to enhance the clearance of Tau aggregates by dissolving the aggregates and releasing previously aggregated Tau in the form of a monomer which can be processed through a much more efficient clearance pathway, i.e., the proteasomal pathway. In terms of the model, the key action of REMBER™ is to enhance or open up the rate constant k4b in FIG. 6B. In effect, this opens up a new, previously unavailable clearance pathway for the Tau aggregates. This new clearance pathway, the proteasomal clearance pathway, is depicted by the k4b rate constant in the FIG. 6B.

The powerful effect of enhanced clearance in the kinetic model is due to the autocatalytic effect of the aggregates, in that the rate of aggregation is directly proportional to the aggregate concentration. This is the primary mechanism responsible for the long-term predicted change in the rate of disease progression, which was borne out in the TRx-014-001 clinical trial. The model raises the possibility that REMBER™, if given much earlier in disease progression (i.e., at or even before clinical MCI), could also modify the structural deterioration in the neuron's clearance pathway and provide a further rationale for REMBER™ as a primary preventive therapy.

A further feature of the kinetic model is that it would predict an early symptomatic effect due to initial dissolution of existing Tau aggregate load. This initial burst of clearance of existing aggregates is predicted by the model to contribute to an early symptomatic improvement. This too was borne out in the REMBER™ Phase 2 clinical trial.

The later disease-modifying action of REMBER™ depends on the extent to which the ongoing rate of production of Tau oligomers, and ongoing degradation of the ELM/proteasomal clearance pathways over time (which is the ultimate determinant of the inherent rate of progression through the Braak stages over time), can be neutralised by enhanced clearance due to solvation/solubilisation of Tau oligomers. Since these factors are directly proportional to the aggregate concentration, small changes in the pharmacokinetic profile of the drug can have a large impact on rate of disease progression. These features of the model were again borne out by the Phase 2 clinical trial, and emphasise the need for maximising the bioavailability of the therapeutically active species that is absorbed. In particular, there is no inherent mechanism within the model in its present form that would predict a dose-response plateau.

Example 4—Relationship Between Cognitive and Haematological Activity

There were defects in the formulation of the 100 mg capsule, summarised above leading to increasing delay in dissolution over time since manufacture. Further studies in vitro have shown that this is most likely due to accelerated cross-linking of the gelatine capsules in the presence of MTC at high fill-weights (i.e., 100 mg capsules).

Published in vitro studies have suggested that absorption of MTC is a complex process which depends in part on the activity of an intrinsic cell-surface thiazine-dye reductase activity (Merker et al., 1998; Merker et al., 2002; May et al., 2004). A pharmacokinetic ("PK") model (discussed further below) has been developed based on published studies in humans (DiSanto and Wagner, 1972a,b,c; Peter et al., 2000) which suggests that the half-life of disappearance of MTC from the primary absorption compartment is 30 minutes, consistent with the stomach being the primary absorption site for orally ingested MTC.

MTC is highly ionised when it is in the oxidised form at pH 7 in a non-reducing environment. As such, it has poor lipid solubility. However, reduction to the reduced ("L-MT") form by addition of two electrons leads to an uncharged species which is readily absorbed. In vitro studies suggest that this reduction step can only occur physiologically at low pH. This property would explain why the stomach is the most likely primary absorption site. PK studies in rodents, pig and primate, indicate that the predominant form of the methylthioninium moiety found in tissues is the colourless L-MT form, and that after oral administration, only a small proportion contributes to the oxidised form which can be readily measured in blood. It is therefore likely that only the L-MT form can cross the blood-brain barrier, where a new steady state is established between oxidised and reduced forms within neurons. After intravenous administration, substantially higher levels of the oxidised form can be detected in blood than after oral administration of the same dose (Peter et al., 2000). Further PK studies in pig have shown that this is due to a difference in the level of the circulating L-MT form after oral administration, and not, as suggested by Peter et al., due to poor bioavailability via the oral route. This suggests that MTC undergoes reduction during oral absorption and subsequent tissue distribution.

In circumstances where dissolution was delayed, as for the 100 mg capsule used in the REMBER™ trial, it is likely that only limited absorption of the nominal dose could have occurred via the reductase mechanism which has been described. This would lead to delayed absorption from the small intestine at higher pH. On the basis of in vitro studies it is deduced that these circumstances would favour the formation of a dimer of oxidised MTC monomers which is well described in literature (Rabinowitch and Epstein, 1941; Lewis et al., 1943; Spencer and Sutter, 1979). Due to anti-parallel stacking, the dimer has no net charge. Therefore, delayed dissolution would be expected to lead to delayed absorption of MTC in the oxidised state at the higher pH of the small intestine. From in vitro studies, the dimer would not be expected to have therapeutic activity, but would have haematological effects due to its ability to oxidise haemoglobin.

This delayed-dissolution hypothesis is consistent with the data derived from the REMBER™ trial. In essence, the trial has shown that MTC has two systemic pharmacological actions: cognitive effects and haematological effects. The cognitive effects do not show a monotonic dose-response relationship, whereas the haematological effects do (FIG. 8). This suggests that two distinct species are responsible for the two types of pharmacological activity: MTC absorbed as the uncharged L-MT form being responsible for the beneficial cognitive activity, and MTC absorbed as an oxidised dimeric species being responsible for the oxidation of haemoglobin. If this were so, it would be expected that a relationship could be derived linking dissolution time with the two distinct pharmacological activities at different capsule strengths. This was indeed found to be the case, as shown in FIG. 8.

A very high correlation ($r=0.996$) was found between the normalised dissolution expressed as percentage dissolved before or after 30 minutes, and the normalised relative cognitive or haematological activity indices. For relative dissolution, the percentage of the total dissolution that occurred in vitro before or after 30 minutes was calculated. The corresponding partitioning of total pharmacological activity was derived as shown in FIG. 7.

It should be borne in mind that the relative cognitive activity at each nominal dose is expressed as the proportion of total pharmacological activity (i.e., cognitive and haematological) at each nominal dose. Therefore, although the 30 mg dose has a smaller absolute cognitive effect than the 60 mg dose, it has a higher relative cognitive activity index relative to total pharmacological activity, because it has less haematological activity than the 60 mg dose.

Conversely, the lack of monotonic dose-response relationship observed in the efficacy analyses of ADAS-cog at 50 weeks implies that the effective therapeutic dose available from the 100 mg capsule was as indicated in FIG. 8, i.e., approximately 25 mg, or a quarter of the nominal dose, similar to the 30 mg dose in activity at 50 weeks. It is for this reason that in the analyses presented above, the 100 mg dose was indicated as "low (100 mg)" to signify that the formulation of these capsules did not permit proportionate delivery and absorption of the expected nominal dose in its therapeutically active form. It would appear that a major determinant of therapeutic activity in the brain is dependent on absorption in the L-MT form, which may be mediated via ability of this form to cross the blood-brain barrier.

These analyses strongly suggest that it is possible to dissociate the beneficial cognitive effects of the methylthioninium moiety of MTC from its undesirable haematological effects by optimising the formulation. As discussed in a prior-filed unpublished patent application (PCT/GB2007/001103, the contents of which are herein specifically incorporated by reference), a novel stabilised reduced salt form (designated "L-MTx") would have the benefit of bypassing the reductase activity which is necessary for absorption of the methylthioninium moiety of MTC. The stable L-MTx has been found to have higher solubility than MTC, and upon dissolution remains substantially in the uncoloured reduced state for more than 1 hr, permitting direct absorption as the reduced methylthioninium species. A further benefit of the stabilised L-MTx may be that even higher efficacy could be achieved because higher doses of the therapeutically active form could be absorbed without limitation by the capacity of the gastric thiazine dye reductase activity on the one hand, and haematological side effects and diarrhoea on the other. These are discussed further below.

As predicted from the present analysis, the L-MT salt form has been found to have significantly less haematological toxicity than MTC. FIG. 9 shows the differences between MTC and L-MTx across a range of oral doses in terms of key red cell parameters in rats dosed daily for 14 days. As can be seen, L-MTx-dosed animals had higher counts of red cells ("RBC"), higher levels of haemoglobin ("HB") and higher red-cell haemoglobin concentration ("MCHC"). The mean red-cell volume was less ("MCV"), indicating that more mature red cells were released from the bone marrow, and the reticulocytosis induced by the haemolytic effects of MTC was reduced ("RETI").

TABLE 4

Statistical analysis of differences in key red cell parameters in rats between MTC and L-MTx doses.

| Dose (mg/kg) | Difference with respect to MTC | p-value |
|---|---|---|
| Haemoglobin (g/dL) | | |
| 0[(1)] | −0.39 | 0.427 |
| 15[(2)] | 0.80 | 0.106 |

TABLE 4-continued

Statistical analysis of differences in key red cell parameters in rats between MTC and L-MTx doses.

| Dose (mg/kg) | Difference with respect to MTC | p-value |
|---|---|---|
| 45[2] | 1.43 | 0.00465 |
| 150[2] | 3.03 | <0.0001 |
| Mean cell haemoglobin concentration (g/dL) | | |
| 0[1] | 0.26 | 0.780 |
| 15[2] | 0.80 | 0.392 |
| 45[2] | 1.93 | 0.0414 |
| 150[2] | 6.05 | <0.0001 |
| Mean cell volume (fL) | | |
| 0[1] | 0.08 | 0.961 |
| 15[2] | −1.18 | 0.475 |
| 45[2] | −7.07 | <0.0001 |
| 150[2] | −9.14 | <0.0001 |
| Red cell count ($10^6$/mL) | | |
| 0[1] | −0.27 | 0.171 |
| 15[2] | 0.41 | 0.041 |
| 45[2] | 1.17 | <0.0001 |
| 150[2] | 1.06 | <0.0001 |
| Reticulocytes (% of red cells) | | |
| 0[1] | −0.08 | 0.973 |
| 15[2] | −0.54 | 0.816 |
| 45[2] | −6.53 | 0.0063 |
| 150[2] | −7.59 | 0.0022 |

[1]The p-value is from a test of whether the value of the vehicle-only dose is significantly different from zero.
[2]The p-value is from a test of whether the value is significantly different from the vehicle-only dose.

Example 5—Available Studies

As can be seen from the foregoing discussion, the optimisation of an appropriate therapeutic dose of MTC and its formulation are complex. A major barrier to this is the lack of a suitable pharmacokinetic model. Although there have been attempts to generate a PK model, these are contradictory and do not take account of all of the available data. Therefore, a completely novel approach to development of a PK model was required. Before presenting this, the available data and models are summarised.

There are 3 published studies of MTC in humans. These are first summarised, and then discussed together. There is a further published study in humans (Rengelshausen et al., (2004) Pharmacokokinetic interaction of chloroquin and methylene blue combination against malaria. Eur. J. Clin. Pharmacol. 60: 709-715) which is not used further in the present document, as its methodology and findings are similar to those of Peter et al. (2000) discussed below.

1) Prior Art Study 1

The first systematic reference studies were carried out by DiSanto and Wagner (1972) and reported in a series of three papers, two of which are summarised below.

1a) DiSanto A R and Wagner J G (1972a) Pharmacokinetics of highly ionized drugs I: whole blood, urine and tissue assays. J Pharmaceut Sc 61: 598-601

The paper reports a method for analysis of MTC in whole blood, urine and tissues. In essence, the method consists in preparing the aqueous matrix with a high salt concentration (>2M), extracting MTC into dichloroethane, and measuring absorbance of the total dichlororethane extract at 660 nm. A stabilised leuco-form of MTC ("leuco-MTC") was found in urine, but not identified chemically. This could be analysed by first converting it to "free-MTC" by adding 5 N HCl and heating in a boiling water bath for 2 min prior to extraction into dichloroethane. The difference between the MTC recovered from urine following acid treatment and MTC recovered without acid treatment ("free-MTC") was reported as "leuco-MTC".

1b) DiSanto A R and Wagner J G (1972b) Pharmacokinectis of highly ionized drugs II: absorbtion, metabolism and excretion in man and dog after oral administration. J Pharmaceut Sc 61: 1086-1090.

In this study, 7 adult male volunteers aged between 21 and 40 years and weighing between 54.5 and 95.3 kg ingested 10 mg of MTC USP. Urine was collected in the intervals tabulated below. Average urinary excretion rates for oxidised-MT ("Ox-MT", also referred to as "free-MB") and leuco-MT ("L-MT") with corresponding standard errors are shown in Table 5, and in FIGS. 10 and 11.

TABLE 5

Excretion rates and standard error ("se") for oxidised MTC ("Ox-MT") and reduced MTC ("L-MT") from DiSanto and Wagner (1972).

| | | Ox-MT | | | |
|---|---|---|---|---|---|
| Time (hr) | Mid-time (hr) | (µg/hr) | se-Ox | L-MT (µg/hr) | se-L |
| 0.5 | 0.25 | 2.31 | 1.06 | 14.01 | 6.98 |
| 1 | 0.75 | 20.59 | 5.05 | 385.06 | 97.98 |
| 2 | 1.5 | 38.66 | 7.50 | 659.14 | 104.79 |
| 3 | 2.5 | 50.56 | 14.50 | 474.29 | 96.93 |
| 4 | 3.5 | 40.66 | 8.76 | 384.43 | 49.37 |
| 6 | 5 | 53.01 | 12.37 | 290.50 | 49.26 |
| 9 | 7.5 | 42.86 | 17.55 | 120.29 | 29.91 |
| 24 | 16.5 | 37.99 | 6.43 | 78.72 | 13.77 |
| 33 | 28.5 | 24.34 | 7.53 | 41.87 | 9.91 |
| 48 | 40.5 | 11.02 | 2.43 | 26.77 | 5.18 |
| 57 | 52.5 | 5.00 | 1.16 | 14.11 | 5.49 |
| 72 | 64.5 | 4.98 | 1.31 | 7.88 | 2.29 |
| 81 | 76.5 | 2.53 | 0.69 | 6.39 | 2.05 |
| 96 | 88.5 | 1.74 | 0.48 | 3.09 | 1.53 |
| 105 | 100.5 | 1.23 | 0.43 | 3.02 | 1.60 |
| 120 | 112.5 | 0.88 | 0.28 | 1.91 | 0.83 |

TABLE 6

Urinary excretion data for Ox-MTC and L-MT

| Parameter | Free | Leuco |
|---|---|---|
| Kel | 0.2263 | 0.2430 |
| K12 | 0.7506 | 0.2962 |
| K21 | 0.2381 | 0.1040 |
| Ka | 0.1626 | 0.9654 |
| Tlag (hr) | 0.2078 | 0.2381 |
| VcF (L) | 29.7918 | 8.2607 |
| Correlation (means, obs vs pred) | 0.9878 | 0.9920 |
| Non-compartmental secondary parameters | | |
| F | 0.1483 | 0.4982 |
| Vc (L) | 4.4188 | 4.1152 |
| Cl (L/hr) | 6.7420 | 2.0074 |
| AUC (µg · hr) | 1483.24 | 4981.55 |
| Urinary excretion (% of total) | 22.94% | 77.06% |
| MRT (hr) | 24.5000 | 16.8774 |
| T½ (distribution, hr) | 0.5930 | 1.1530 |
| T½ (elimination, hr) | 15.0364 | 16.4953 |

The following standard abbreviations are used in the table:
Kel (terminal elimination rate constant),
K12 (rate constant for transfer from putative compartment 1 to compartment 2),
K21 (rate constant for transfer from putative compartment 2 to compartment 1),
Ka (absorption rate constant, Tlag (absorption time-lag before drug appears in central (ie blood) compartment).
VcF (Vc x F), F (calculated bioavailability), Vc (theoretical volume of distribution of the drug in the central compartment),
AUC (area under the curve, a measure of total drug in blood),
MRT (mean residence time, time for 63.2% of administered dose to be eliminated),
T½ (half-life).

From the urinary excretion data, Ox-MT and L-MT differ with respect to distribution phase and apparent bioavailability. However, the terminal elimination half-life (~16 hr) and corrected apparent central volume (4 L) are comparable (Table 6). Total urinary recovery is 6.465 mg (i.e. 65% of dose), of which 23% is excreted as Ox-MT and 77% is excreted as L-MT.

2) Prior Art Study 2

This is described in Peter C, Hongwan D, Kupfer A, Lauterberg B H (2000) Pharmacokinetics and organ distribution of intravenous and oral methylene blue. Eur J Clin Pharmacol 56: 247-250.

In this study 7 human volunteers (4 males, 3 females) aged 19-53 were given MTC 100 mg (313 µM) on 3 occasions at least 1 week apart as either a single IV injection (20 mg/ml in 0.9% NaCl over 30 sec) or two 50 mg capsules in gelatine, or two 50 mg capsules in gelatine together with 800 mg of Mesna (sodium mercaptoethanesulphonate). The pharmacokinetic effect of co-administration of Mesna was included because of the clinical use of MTC in cancer chemotherapy regimes based on ifosfamide for which Mesna is co-administered to prevent urotoxicity.

The analytical methodology for blood differed from that used by DiSanto and Wagner in the following respects:
Inclusion of an internal standard
Use of sodium hexanesulphonate as an ion-pair to enhance extraction into dichloroethane
Chromatographic separation using a Nucleosil 100-5 CN column with an isocratic mobile phase, with efflux monitored at 660 nm.

Peter et al. also measured urinary excretion of Ox-MT and L-MTC to 24 hr, but reported only means of total excretion at intervals ending at 2, 4, 6, 10, 14, 24 hr post-dose. The analytical method in urine was said to be essentially identical to that of DiSanto and Wagner.

The results are not tabulated by the authors, but are shown graphically as reproduced in FIGS. 14 and 15.

The data have been read from these graphs and are tabulated below.

TABLE 7

Concentration of Ox-MT in whole blood after IV administration of 100 mg of MTC.

| Time (hr) | Blood Ox-MT (µmol/L) |
| --- | --- |
| 0.09 | 6.06 |
| 0.15 | 3.32 |
| 0.24 | 1.73 |
| 0.33 | 1.65 |
| 0.5 | 0.78 |
| 0.65 | 0.61 |
| 0.83 | 0.39 |
| 1.01 | 0.41 |
| 1.99 | 0.26 |
| 4 | 0.18 |

TABLE 8

Concentration of Ox-MT in whole blood after oral administration of 100 mg MTC (mean of with and without Mesna).

| Time (hr) | Blood Ox-MT (µmol/L) |
| --- | --- |
| 0 | 0 |
| 0.09 | 0.00064 |
| 0.15 | 0.0011 |
| 0.24 | 0.0064 |
| 0.33 | 0.017 |

TABLE 8-continued

Concentration of Ox-MT in whole blood after oral administration of 100 mg MTC (mean of with and without Mesna).

| Time (hr) | Blood Ox-MT (µmol/L) |
| --- | --- |
| 0.5 | 0.041 |
| 0.83 | 0.055 |
| 1.01 | 0.064 |
| 1.99 | 0.069 |
| 4 | 0.038 |

Peter et al report the following pharmacokinetic parameters (Table 9).

TABLE 9

Pharmacokinetic parameters reported by Peter et al. (2000) for MTC administered by intravenous and oral routes.

| Parameter | IV | Oral |
| --- | --- | --- |
| AUC (µmol/min/ml) | 0.134 | 0.011 |
| Cl (L/hr)[1] | 3 | |
| % of dose excreted in urine at 24 hr | 28.6 | 18.6 |
| Estimated elimination T½: | | |
| blood (1-4 hr, hr) | 5.25 | |
| urine (4-24 hr, hr) | | 6.6 |

[1]Cl: clearance, the volume of blood cleared of drug in unit time.

Peter et al. further note that the fraction of total MT excreted in the urine in the L-MB form was approximately ⅓ of the total, and this did not differ between oral and IV dosing.

3) Prior Art Study 3

This is described in Moody J P, Allan S M, Smith A H W, Naylor G J (1989) Methylene blue excretion in depression. Biol Psychiat 26: 847-858.

This is a limited study of 24-hr urinary excretion during a 3-week trial period in depressed subjects taking 15 mg/day (5 mg t.i.d.) or 300 mg/day (100 mg t.i.d.). Twenty-four hr urine collections were obtained in 7 subjects at the end of 7, 14 or 21 days treatment. The analytical method was said to be that of DiSanto and Wagner. The results are summarised below in Table 10.

TABLE 10

Summary of data on urinary excretion of MTC in humans from the study by Moody et al. (1989).

| | Days | Ox-MT (mg) | L-MT (mg) |
| --- | --- | --- | --- |
| Repeat Dose Study (15 mg/24 hr) | 7 | 6.1 | 7.2 |
| | 14 | 5.3 | 8 |
| | 21 | 6.1 | 6.4 |
| 24 hr urinary excretion (mg) | | 5.8 | 7.2 |
| % of total urinary excretion | | 44.8% | 55.3% |
| F (apparent bioavailability) | | 0.39 | 0.48 |
| Repeat Dose Study (300 mg/24 hr) | 7 | 43.9 | 75.6 |
| | 14 | 41.1 | 71.6 |
| | 21 | 45.2 | 60.4 |
| 24 hr urinary excretion (mg) | | 43.4 | 69.2 |
| % of total urinary excretion | | 38.6% | 61.5% |
| F (apparent bioavailability) | | 0.14 | 0.23 |

| Single Dose Study | Dose (mg) | Ox-MT (mg) | L-MT (mg) | Total-MT (mg) |
| --- | --- | --- | --- | --- |
| | 25 | 14.9 | 2.8 | 17.7 |
| | 50 | 28.1 | 2.7 | 30.8 |
| | 100 | 33.5 | 6 | 39.5 |

TABLE 10-continued

Summary of data on urinary excretion of MTC in humans from the study by Moody et al. (1989).

| % of total urinary excretion | 25 | 84.2% | 15.8% |  |
|---|---|---|---|---|
|  | 50 | 91.2% | 8.8% |  |
|  | 100 | 84.8% | 15.2% |  |
| F (apparent bioavailability) | 25 | 0.60 | 0.11 | 0.71 |
|  | 50 | 0.56 | 0.054 | 0.62 |
|  | 100 | 0.34 | 0.060 | 0.40 |

The single-dose data from this study has been combined with that of the DiSanto & Wagner and Peter et al. studies to provide an estimate of apparent oral bioavailability based on urinary excretion at 48 hr of total-MT.

Discussion of Key Results

There are several respects in which the models developed on the basis of the data tabulated above are inconsistent. The most important is that the terminal elimination half-life deduced by Peter et al. (5.5-6.3 hr) from analysis of blood concentration data is inconsistent with the terminal elimination half-life deduced by DiSanto and Wagner (15-16.5 hr) from urinary excretion data. It is also inconsistent with long discoloration of urine observed following intra-operative IV administration of MTC to localise parathyroid glands for surgery (Kuriloff and Sanborn, 2004). The problem arises because Peter et al. (2000) have based their estimates on blood data obtained of 4 hr, or 12 hr in the case of Rengelshausen et al. (2004) who followed the same pharmacokinetic approach. These analyses fail to take account of the terminal elimination phase, because of technical difficulties encountered in estimating Ox-MT levels in blood, even using LC-MS (Liquid Chromatography—Mass Spectroscopy) after the blood levels fall below detection limits. The terminal elimination phase can be better analysed using urinary excretion data. Although it is well known that the urinary excretion rate can provide a valid way of estimating the elimination rate constant in simple systems (eg Gibaldi and Perrier (1982) Pharmacokinetics), the problem with the available MTC data is that is complex, and there is no obvious way to link the blood data and urinary excretion data into a single coherent integrated model able to account both for the IV and oral dosing cases. Providing a solution to this problem is crucial for the development of a suitable predictive model which can be used to optimise dosing of MTC or other MT forms for the treatment of AD and in other therapeutic contexts. The solution to this problem is discussed below.

Example 6—Development of Integrated Pharmacokinetic Model i) Oral Bioavailability The Peter et al. data provide a useful indication of blood levels following oral vs IV administration. Comparison of the AUC values over the 4 hr time-period indicates that blood levels following oral administration are 8.2% of those seen after IV administration.

However, this estimate cannot be used to determine oral bioavailability. It is inconsistent with the Peter et al. urine recovery data at 24 hours, where urinary recovery following oral dosing was found to 65% of that obtained after IV dosing (see Table 5). This figure is comparable with the urinary excretion data obtained from the DiSanto and Wagner and the Moody et al. studies.

The data from these studies are combined in FIG. 16 to provide an overall estimate of oral bioavailability. It suggests a figure between 40%-80% depending on dose over the range 10-100 mg. It is also apparent from FIG. 16 that there is dose-dependent reduction in bioavailability as determined by urinary recovery following oral dosing.

There is therefore a discrepancy between the estimate of oral bioavailability determined from direct measurement in blood and that determined from urinary excretion. This implies that the low blood levels seen in blood following oral dosing cannot be explained simply by a limitation in absorption as suggested by Peter et al. (2000). The low blood levels seen after oral administration are more likely to reflect a difference in the apparent volume of distribution for MTC administered orally and by the IV route. Rapid early tissue uptake was confirmed by DiSanto and Wagner who reported that 29.8% of the intravenous dose of MTC could be recovered in heart, lung, liver and kidney at 2 minutes following administration in rat. This picture of an early rapid distribution phase followed after 10 hrs by a slow elimination phase is also consistent with the urinary excretion data shown in FIGS. 12 and 13. Therefore, blood data collected over a 4 hr time course as provided by Peter et al. are not sufficient to derive a valid estimate of redistribution of MT between absorption, central and peripheral compartments.

ii) Model Constructed by Combining Blood Data from Peter et al. (Tables 7&8) and Urinary Excretion Data from DiSanto and Wagner (Table 5)

One approach to deriving a pharmacokinetic model from the available studies is to use linear differential equations to determine directly a system of compartments which can be fitted to the available data sets. The data used are the DiSanto and Wagner urinary excretion data set for 7 subjects listed in Table 5, taking account of differential excretion of Ox-MT and L-MT. This is combined with the Peter et al blood level data listed in Tables 7 and 8, also based on 7 subjects. It is assumed that the DiSanto and Wagner data can be linked to both IV and oral blood concentration data sets after appropriate scaling on the basis that the urinary excretion profiles as determined by Peter et al. were similar for the 2 routes of administration (FIG. 17).

However, the DiSanto and Wagner urinary excretion data set is used for fitting in preference to the Peter et al. data because the latter does not explicitly take account of differential excretion of Ox-MT and L-MT, and because the sampling intervals are coarse relative to those available from the DiSanto and Wagner data set.

The modelling was done in two stages:

In the first stage the Peter et al. blood concentration data to 4 hr following a single IV dose of 100 mg of MTC was combined with the DiSanto and Wagner urinary excretion data set to 120 hr for single oral MTC dose of 10 mg. The second stage was to see if the same or similar compartment system can be used to fit the Peter et al. blood concentration data following a single oral dose of 100 mg of MtC, combined with the DiSanto and Wagner urinary excretion data set to 120 hr for single oral MTC dose of 10 mg. In both cases, scaling parameters to allow for the 10-fold difference in dose were estimated by the corresponding models.

FIG. 18 shows the best distribution of compartments and corresponding rate constants which could be fitted to the three data sets (Peter et al IV-dosing blood concentration data [Table 7], DiSanto and Wagner urinary Ox-MT data [Table 5] and urinary L-MT data [Table 5]). The central compartment is C2. The scaling parameters to allow for the fact that there was a 10-fold difference in the doses used in the blood and urine data sets were explicitly estimated by the model for urinary Ox-MT (S-Ox) and urinary L-MT (S-L) and are shown in Table 11. The solution to the model requires two peripheral compartments, shown as C3 and C4 in FIG. 18, and a further excretion compartment (C5). There are two outputs from C5, one which represents scaled observed urinary excretion of L-MT (designated K50 in Table 11), and a second output which represents an unmeasured loss (designated K500 in Table 11), which is presumed to represent secondary hepatic metabolism of MT which is excreted through the bile as an unmeasured metabolite. The output from C3 (designated K30 in Table 11) represents the quantity measured as urinary Ox-MT. The percentages shown represent partitions of predicted total excretion at 120 hr, estimated from the corresponding AUC values.

The parameters estimated by the model are listed below in Table 11.

TABLE 11

Model parameters estimated for a single intravenous dose of 100 mg MTC. The rate constants are as indicated in FIG. 18. K50 is the urinary excretion rate constant from C5, and K500 is the presumptive hepatic excretion rate constant from C5. V2 is the apparent volume of distribution of MT in C2 calculated by the model. S-Ox and S-L are the scaling parameters calculated by the model to account for the fact that urinary data came from an experiment in which MTC was administered as a 10 mg oral dose, and the blood data came from an experiment in which MTC was administered as a single 100 mg IV dose.

| Parameter | Estimate |
|---|---|
| K23 | 1.60 |
| K24 | 3.94 |
| K30 | 0.0093 |
| K32 | 0.088 |
| K42 | 0.87 |
| K45 | 0.28 |
| K50 | 0.78 |
| K500 | 0.081 |
| S-Ox | 10.6 |
| S-L | 6.3 |
| V2 | 66.03 |
| Correlations (observed vs predicted): | |
| Blood | 0.98 |
| Urinary Ox-MT | 0.96 |
| Urinary L-MT | 0.98 |

In the second stage, the same basic model was fitted to the Peter et al. blood concentration data following a single oral dose of 100 mg of MTC (Table 8), and scaled urinary excretion data from DiSanto and Wagner (Table 5) following a single oral dose of 10 mg of MTC.

FIG. 22 shows the best distribution of compartments and corresponding rate constants which could be fitted to the three data sets (Peter et al oral-dosing blood concentration data [Table 7], DiSanto and Wagner urinary Ox-MT data [Table 5] and urinary L-MT data [Table 5]). The oral model assumes two further compartments prior to the central compartment (C2). These are C1 (the primary absorption compartment, assumed to correspond to stomach), and a second pre-central compartment (C6, presumed to represent a first-pass metabolism hepatic compartment). There is a loss from C1 (designated K100 in Table 12) which is presumed to represent non-absorbed MTC, and further loss from C6 (designated K600 in Table 12) which is presumed to represent loss due to first pass metabolism. The scaling parameters to allow for the fact that there was a 10-fold difference in the doses used in the blood and urine data sets were explicitly estimated by the model for urinary Ox-MT (S-Ox) and urinary L-MT (S-L) and are shown in Table 12. As for the IV model, the solution to the model requires two peripheral compartments, shown as C3 and C4 in FIG. 22, and a further excretion compartment (C5). There are two outputs from C5, one which represents scaled observed urinary excretion of L-MT (designated K50 in Table 12), and a second output which represents an unmeasured loss (designated K500 in Table 12), which is assumed to represent secondary hepatic metabolism of MT which is excreted through the bile as an unmeasured metabolite. The output from C3 (designated K30 in Table 12) represents the quantity measured as urinary Ox-MT. The percentages shown represent partitions of predicted total output from the system excretion at 120 hr, estimated from the corresponding AUC values.

The parameters estimated by the model are listed below in Table 12.

TABLE 12

Model parameters estimated for single oral dose of 100 mg MTC.

| Parameter | Estimate |
|---|---|
| K100 | 0.44 |
| K16 | 1.68 |
| K23 | 1.39 |
| K24 | 0.67 |
| K30 | 0.016 |
| K32 | 0.091 |
| K42 | 0.00095 |
| K45 | 2.059 |
| K50 | 1.45 |
| K500 | 0.61 |
| K600 | 0.20 |
| K62 | 0.35 |
| S-Ox | 12.3 |
| S-L | 19.6 |
| Vc2 (L) | 319.9 |
| Correlations (observed vs predicted): | |
| Blood Ox-MT | 0.99 |
| Urinary Ox-MT | 0.98 |
| Urinary L-MT | 0.99 |

Scaling factors for urinary Ox-MT and L-MT from DiSanto and Wagner (10 mg dose, oral) to fit with Peter et al data (100 mg dose, oral) are explicitly estimated for the oral version of the model as S-Ox and S-L respectively. A further modification required to achieve a fit for the oral data was the introduction of a time delay for the urinary excretion data from DiSanto and Wagner. This delay was estimated as a non-linear function ranging from 0.2 to 1 hr for excretion times earlier than 1 hr, and a constant time delay of 1 hr thereafter.

As can be seen in Table 11 and 12, there were very high correlations (all greater than 0.96) between the model outputs and the input data sets, as can also be readily seen from FIGS. 19-21 and 23-25. The model therefore provides a close fit to the experimental data.

iii) Comparisons of Model Outputs with Other Data Sources

As a check of the oral model, its outputs were compared with other available data sets.

The outputs of the oral model (FIG. 22) were first compared with the urinary excretion rates reported by Peter et al. (2000) and shown above in FIG. 18. This comparison is shown below in FIG. 26. There was good overall agreement, apart from the 2-4 hr collection interval, when the level reported by Peter et al. was half of that predicted by the model. Excluding this value, the correlation between the two was 0.86. The total 24-hour excretion predicted by the model and that reported by Peter et al. is also compared in FIG. 26. The model predicts that total urinary excretion was 23% of the dose, whereas the Peter et al. estimate was 18.6%.

As a further check on the model, the total predicted 48-hour urinary excretion was compared with the data shown above in FIG. 16, which compiles the urinary excretion data from DiSanto and Wagner and Moody et al. This is shown again in FIG. 27, with the model output indicated by "M", and the Peter et al. data indicated by "P".

Finally, a comparison was made between the compartment predictions and the results from an oral study in which pigs were administered a single 20 mg/kg dose, and brain levels of MT were determined. Pigs were given a single oral administration of MTC at a target dose level of 20 mg/kg bodyweight. Blood (0.5, 1, 2, 4, 8, 12, 24 and 48 h) and urine (1, 2, 3, 4, 5, 6, 7, 8, 12, and 24 h) were collected at regular timepoints up to 48 hrs. Two animals were sacrificed at each of 1, 8, 24 and 48 h post dose and brain samples retained. Pharmacokinetic evaluation of the free base of MTC was performed on whole blood and brain tissue samples. Two batches of brain tissue sample were extracted for each animal and analysed essentially as described by Peter et al (2000).

In order to use the pig data to determine which human model compartment predicts the brain levels, the time-base for the pig data was rescaled to correspond to the human half-life (15.7 hr).

The results are shown in FIG. 28. All compartments have been rescaled to their respective maxima. It can be seen from FIG. 28 that the central compartment (C2, blood) and C4 follow each other very closely, indicating that MT is freely exchangeable between C2 and C4.

On the other hand, elimination of MT from the pig brain can be seen to parallel the predicted elimination from C3, and not from C4. Therefore, of the two inner compartments of the model (C4 and C3), it can be seen that C3 provides a prediction of expected brain levels.

iii) Interpretation of the Integrated Pharmacokinetic Model for MTC

The main kinetic features of the IV and oral models are now compared.

a) IV Human Model

The key kinetic features of the human intravenous model is summarised in Table 13. The data have been normalised to the case of a single 100 mg dose (313 µM).

TABLE 13

Summary of the key kinetic features of the human intravenous PK model.

Intravenous model

| | A-T½[1] | D-T½[1] | E-T½[1] | AUC[2] | AUC-out[3] | % AUC-out[3] | Tmax[4] | MRT[5] |
|---|---|---|---|---|---|---|---|---|
| Central compartments | | | | | | | | |
| C2 | 0.1 | 1.4 | 17.9 | 286 | | | | 16.3 |
| C4 | 0.1 | 1.4 | 17.9 | 984 | | | 0.5 | 17.1 |
| Deep compartment | | | | | | | | |
| C3 | 1.3 | 1.4 | 17.9 | 4645 | | | 4.0 | 26.6 |
| Excretion compartment | | | | | | | | |
| C5 | 0.6 | 1.6 | 17.9 | 320 | | | 2.0 | 18.2 |
| Post-central outputs | | | | | | | | |
| C500 | | | | | 2377 | 8.2% | | |
| Ur-Ox-MT | | | | | 3707 | 12.8% | | |
| Ur-L-MT | | | | | 22836 | 79.0% | | |
| Total outputs | | | | | 28920 | | | |

[1] For each of the compartments, half-lives for an absorption-phase (A-T½), a distribution-phase (D-T½) and an elimination phase (E-T½) have been calculated in hr, using a tri-exponential approximation to the model output data.
[2] The AUC$_\infty$ (µmol-hr/l) has been calculated for MT in each of the "interior" compartments.
[3] The AUC$_\infty$ (µmol-hr/l) has been calculated for MT in each of the post-central compartments, and these have been shown by percentage.
[4] The Tmax is the calculated time (hr) after dose at which the MT level in each interior compartment is maximum.
[5] MRT is the mean residence time in each compartment, calculated as the time required for 63.2% of the administered dose to be eliminated.

Brain tissue (500 mg) was vortexed and then extracted with dichloroethane (5 ml) and the organic phase taken to dryness under nitrogen. The extract was taken up with methanol and separated by reverse-phase HPLC with ultra-violet detection. The method was validated, using internal standards, over the range of 10 to 2000 ng of MTC per gram of tissue. The mean inter-occasion accuracy for MTC was 107%, 95% and 105% at 20, 100 and 1600 ng/g, respectively and the coefficient of variation at each level, was not more than 20%.

The terminal elimination half-life in the pig was found to be 23.5 hours for both blood and brain, consistent with the urinary excretion findings of DiSanto and Wagner indicating that the terminal elimination phase is much longer than estimated either by Peter et al. (2000) or Rengelshausen et al. (2004).

Central Compartments.

As can be seen from Table 13, and also from FIG. 28, the kinetic properties of MT in the C2 and C4 compartments are essentially identical, supporting the concept that the form of MT in C4 is in ready exchange equilibrium between the form measured as the blood level of Ox-MT in blood in C2. As the C4 compartment is the principal determinant of urinary excretion of the L-MT form measured in urine, it is concluded that the C4 form of MT represents the L-MT side of the L-MT-Ox-MT equilibrium which exists in the body. After IV administration, the amount of MT in C4 reaches its maximum level within 30 minutes, and is thereafter eliminated at the common terminal elimination rate.

Deep Compartment.

By contrast, it can be seen that C3 in the IV case has different dynamic properties. It takes 4 hr after administration for the maximum C3 level to be reached, and the mean residence time in C3 is substantially longer than in either C2 or C4. In light of the pig brain data, it is inferred that the C3 compartment represents the pool of MT which is kinetically trapped inside cells as described by May et al. (2004).

According to May et al. (2004), MT needs to be in the L-MT form in order to cross the cell membrane. Inside the cell, there is a new L-MT-Ox-MT equilibrium which is determined by a combination of the predominant reducing environment in the intracellular milieu, and the prevailing pH inside the cell (~pH 7). Experiments in vitro (not shown) have indicated that it is very difficult to keep MT in the reduced state at pH 7 using physiologically acceptable reducing agents at physiologically acceptable concentrations. That is, at pH 7, MT would tend to exist predominantly in the Ox-MT state were it not for the predominantly reducing conditions which are maintained within the cell. However, in the Ox-MT form, MT cannot diffuse out of the cell. This creates conditions for a new equilibrium whereby MT is trapped within cells, leading to accumulation of intracellular MT against a concentration gradient, which can be demonstrated in tissue culture (not shown). This explains the otherwise paradoxical pharmacokinetic observation that MT is both rapidly distributed to tissues following IV administration (as reported by DiSanto and Wagner), but nevertheless eliminated much more slowly. Thus DiSanto and Wagner found that within 2 minutes of a dose administered IV in rats, approximately 25% could be recovered from the major organs.

According to the human IV model, the level of MT which is measured in urine as the Ox-MT form is closely related kinetically to the species which is trapped within an intracellular environment, including the brain, as indicated by the pig brain data.

b) Oral Human Model

The key kinetic features of the human oral model is summarised in Table 14. The data have been normalised to the case of a single 100 mg dose (313 µM).

TABLE 14

Summary of the key kinetic features of the human oral PK model (for details see footnotes to Table 13).

Oral Model

| | A-T½ | D-T½ | E-T½ | AUC | AUC-out | % AUC-out | Tmax | MRT |
|---|---|---|---|---|---|---|---|---|
| Input compartments | | | | | | | | |
| C1 | | | | 154 | | | | 0.5 |
| C6 | | | | 467 | | | 0.9 | 2.4 |
| Central compartments | | | | | | | | |
| C2 | 0.5 | 1.3 | 15.7 | 184 | | | 2.0 | 15.7 |
| C4 | 0.5 | 1.3 | 15.7 | 60 | | | 2.0 | 16.0 |
| Deep compartment | | | | | | | | |
| C3 | 1.4 | 1.3 | 15.7 | 2345 | | | 5.0 | 25.0 |
| Excretion compartment | | | | | | | | |
| C5 | 0.7 | 1.4 | 15.7 | 61 | | | 2.0 | 16.5 |
| Pre-central outputs | | | | | | | | |
| C100 | | | | | 7329 | 23.0% | | |
| C600 | | | | | 9869 | 31.0% | | |
| Pre-central outputs | | | | | | | | |
| C500 | | | | | 3422 | 10.7% | | |
| Ur-Ox-MT | | | | | 3202 | 10.0% | | |
| Ur-L-MT | | | | | 8060 | 25.3% | | |
| Total outputs | | | | | 31882 | | | |

Primary Absorption Compartment.

In the oral model, there are 2 input compartments (C1 & C6) prior to the appearance of MT in the central compartments (C2 & C4). As discussed above in the section Relationship Between Cognitive and Haematological Activity, the properties of C1 are crucial in determining the bioavailability and form in which MT is absorbed. As shown in Table 14, the mean residence time in C1 is 30 minutes. It can be calculated that 50% of MT has been absorbed by 30 minutes, and that 90% of MT has been absorbed from C1 by 1 hr. This indicates that C1 is the stomach, where the low pH (pH~2) favours the enzyme-mediated conversion of MT to the L-MT form which is readily absorbed (May et al., 2004). It is important to note that 23% of administered MTC escapes absorption, and is thereafter lost (shown as C100 in Table 14). Therefore, absorption from C1 is also critical in determining how much MTC passes through the gastro-intestinal tract to the distal gut where the mild antibiotic activity of MTC causes diarrhoea by repopulation of distal gut flora. The properties of C1 are therefore crucial for optimising the absorption and efficacy of MTC, and minimising the side effects, both from unabsorbed MTC (diarrhoea) and from late-absorbed MTC as shown in the clinical trial (haematological side effects).

Central Compartments.

As for the IV model, the kinetic properties of the C2 and C4 compartments are essentially identical in the oral model. The significant difference between the IV and oral cases is that the rate constant K24 (3.94) is very is 4× higher in the IV case than in the oral case (K24: 0.67). This indicates that following IV administration, there is a major flux of the administered Ox-MT to the L-MT form. By contrast, in the oral case, the bulk of MT has already been reduced to the L-MT form prior to entry into the central compartments.

A further significant difference which can be seen between the IV model and the oral model is that the estimated apparent volume of distribution of MT is very much greater in the oral case (320 L, Table 12) than in the IV case (66 L, Table 11). This almost 4-fold difference is the main explanation for the low concentration of Ox-MT observed in the blood following oral administration than after IV administration. This was explained erroneously by Peter et al. (2000) as a low bioavailability. Although it is true that approximately half the orally administered dose is lost by a combination of non-absorption (the C100 loss in Table 14 and FIG. 22), and first-pass metabolism (the C600 loss in Table 14 and FIG. 22), the C2 AUC in the oral case is 64% of the C2 AUC in the IV case. Therefore the apparent bioavailability as determined by blood AUC ratios is very close to the apparent bioavailability calculated from the DiSanto and Wagner urine excretion data, which indicated that 65% of the administered dose could be recovered in urine for the 10 mg dose case.

Deep Compartment.

The maximum level of MT is seen in the central compartments 2 hr after administration. By contrast, the peak level is reached in the deep compartment (C3) only at 5 hr after administration. Again the mean residence time of MT in C3 is much longer than in the central compartments (25 hr vs 16 hr). Therefore, the features of C3 are essentially identical in the IV and oral dosing models.

It is important to compare the apparent bioavailability of MT in C3, which is representative of brain levels, between the oral and IV dosing routes. The oral C3 AUC is 50% of the IV C3 AUC. Therefore essentially half of the oral dose is available within cells compared to the IV case.

Example 7—Dosing Implications of Integrated Pharmacokinetic Model

An integrated pharmacokinetic model is a critical tool required for:
- optimisation of dosing regime
- optimisation of formulation
- establishing relationship between blood-level and efficacy The key planning parameter that can be derived from the pharmacokinetic model is the prediction of steady-state levels achieved on repeated dosing. It will be evident that a model which assumes a terminal elimination half-life of 5-6 hr (Peter et al., 2000; Rengelshausen et al., 2004) will produce quite different estimates of the optimal dosing regime to one in which the elimination half-life is 16 hr. It can be estimated from the integrated model which has been developed that a dosing regime of 3/day will have quite different implications as regards predicted steady-state levels assuming an elimination half-life of 6 hr vs 16 hr. Thus, if the Peter et al. estimate were true, then the accumulation factor (R, ie the ratio of steady state level to single dose level) that would be seen for 8-hourly dosing would be 1.4. By contrast, if the estimate of 16 hr is true, then the corresponding value of R is 4.8 for 8-hourly dosing. This implies that there would be a 3.4-fold difference in the expected steady-state level of MT (in blood and in brain) according to the two models. It is therefore difficult to determine an accurate relationship between dose and efficacy or side effects without a valid pharmacokinetic model.

The key intervening variable linking dose and efficacy is an estimate of the steady-state levels of MT in critical compartments at varying regular dosing frequencies. The model permits these to be determined as the predicted average steady state levels in C2 and C3, as shown in Table 15.

Table 15. Predicted mean steady-state levels of MT in compartment C2 and C3 as a function of dosing frequency (values in µmol).

|       | C2  | C3    |
|-------|-----|-------|
| 3/day | 4.8 | 295.5 |
| 2/day | 3.2 | 197.0 |
| 1/day | 1.6 | 98.5  |

Correlation Between Observed and Predicted Clinical Efficacy Based on the Integrated Oral Human Pharmacokinetic Model We first examine the relationship between the observed clinical efficacy (effect size in ADAS-cog units at 50 weeks) and the predicted steady-state level of MT in the deep compartment (C3) which is, as discussed above, correlated with measured brain levels in pig. That is, the quantity of MT in C3 and the concentration of MT in brain are related by a constant which depends on the fraction of MT which reaches the brain, and the accuracy of detection of total MT in brain. As this scaling factor is at present unknown in the human case, for the purpose of further discussion the quantity of MT in C3 is taken as a proxy for the expected brain level. The relationship is shown in FIG. 29.

As can be seen in FIG. 29, there is a very close relationship between the predicted average steady state level of MT in brain and the clinical effect size of REMBER™ in TRx-014-001 for the 30 mg 3/day and the 60 mg 3/day doses. The relationship does not hold for the 100 mg capsule for the reasons discussed above in the section Relationship Between Cognitive and Haematological Activity. In essence, the delay in dissolution of the formulation of the 100 mg capsule used in TRx-014-001 did not permit proportionate absorption of MTC in its therapeutically active form.

An identical relationship can be defined between steady-state blood level of MT (ie determined by C2) and effect size, as shown in FIG. 30.

Dosing and Formulation Implications of Correlation Between Observed and Predicted Clinical Efficacy Based on the Integrated Oral Human Pharmacokinetic Model From the foregoing analysis, there is the expectation of a clear monotonic dose-response relationship between blood levels of MT which can be measured clinically and effect size. From this, appropriate nomograms can be calculated which take account of measurement methodology. That is, efficacy could be related to blood levels, and therapeutic blood levels could be specified using appropriate analytical methodology.

A further implication of the relationship shown in FIG. 30 is to calculate the relationship between observed capsule dissolution and the efficacy deficit, ie the difference in effect size between observed effect size and predicted effect size. This is shown in FIG. 31.

As can be seen from FIG. 31, there is a steep loss of predicted efficacy as the observed percentage capsule dissolution at 30 minutes drops below 20%. This confirms the conclusions reached above in the section Relationship Between Cognitive and Haematological Activity, and confirms that rapid dissolution is critical for therapeutic activity. As discussed further in the section Interpretation of the integrated pharmacokinetic model for MTC, this can be explained by the critical role of the stomach in the absorption of the MT moiety in its therapeutically active form.

Therefore, in the design of an improved formulation of MTC, the attainment of predicted efficacy is critically determined by the requirement that the dissolution of the investigational medicinal product (i.e. tablet or capsule) be greater than 50% in 30 minutes in standard conditions.

The relationships described herein have implications as regards the conventional approach to achieving a more convenient dosing regime, i.e. 2/day or 1/day. These dosing regimes would be much more desirable in patients with dementia, who are forgetful and hence need prompting to take medication. The conventional approach to achieving a more convenient dosing regime is to create a slow-release formulation. However, the present analysis indicates that, on the contrary, a very high loading, slow-release formulation of an MTC-based form of a therapeutic product would essentially eliminate efficacy, as illustrated conveniently by the properties of the 100 mg capsule in TRx-014-001.

A further inference which can be drawn from FIGS. 29 & 30 is that the dose of an MTC-based form of a therapeutic product would need to be administered at a unit dosage of 120 mg or greater to achieve a level of efficacy comparable to that seen in the TRx-014-001 clinical trial with the unit dose of 60 mg administered 3 times per day.

A further inference which can be drawn from FIGS. 29 & 30 is that a unit dosage of 100 mg or more administered 3 times per day would be required to achieve a level of efficacy higher than that seen in the TRx-014-001 clinical trial. However, as discussed in the section Summary of Phase 2 Clinical Trial TRx-014-001 there is a limitation in the amount of MTC which can be administered in the present formulation because of the increasing adverse haematological effects and diarrhoea at doses at or above 100 mg 3/day.

Implications for Improved Formulations and Dosing Regimes

As can be seen from FIG. 31A, there is a steep loss of predicted efficacy as the observed percentage capsule dissolution at 30 minutes drops below 20%.

Therefore, in the design of an improved formulation of MTC, the attainment of predicted efficacy is critically determined by the requirement that the dissolution of the investigational medicinal product (i.e. tablet or capsule) be greater than 50% in 30 minutes in standard conditions.

The relationships described herein have implications as regards the conventional approach to achieving a more convenient dosing regime, ie 2/day or 1/day. These dosing regimes would be much more desirable in patients with dementia, who are forgetful and hence need prompting to take medication. The conventional approach to achieving a more convenient dosing regime is to create a slow-release formulation. However, the present analysis indicates that, on the contrary, a slow-release formulation of an MTC-based form of a therapeutic product would essentially eliminate efficacy, as illustrated conveniently by the properties of the 100 mg capsule in TRx-014-001.

A further inference which can be drawn from FIGS. 29 & 30 is that the dose of an MTC-based form of a therapeutic product would need to be administered at a unit dosage of 120 mg or greater to achieve a level of efficacy comparable to that seen in the TRx-014-001 clinical trial with the unit dose of 60 mg administered 3 times per day.

A further inference which can be drawn from FIGS. 29 & 30 is that a unit dosage of 100 mg or more administered 3 times per day would be required to achieve a level of efficacy higher than that seen in the TRx-014-001 clinical trial. However, as discussed in the section Summary of Phase 2 Clinical Trial TRx-014-001 there is a limitation in the amount of MTC which can be administered in the present formulation because of the increasing adverse haematological effects and diarrhoea at doses at or above 100 mg 3/day.

Correlation Between Observed and Predicted Haematological Side Effects Based on the Integrated Oral Human Pharmacokinetic Model We now consider the relationship between the expected steady-state level of MT in C2 (blood) and the haematological side effects observed in the TRx-014-001 study. Loss of red cells at 24 weeks is taken as the most informative indicative variable. The relationship is shown below in FIG. 31B.

As can be seen in FIG. 31B, the level of loss of red cells is very much higher than the predicted steady state level of MT in the blood. This is strongly confirmatory of the delayed dissolution hypothesis outlined in the section Relationship Between Cognitive and Haematological Activity. Specifically, according to the delayed dissolution hypothesis, a quite distinct form of MT is responsible for haematological side effects. This was postulated to be a dimer, the formation of which is favoured in the alkaline conditions of the small intestine and lower gut. Therefore, the haematological side effects observed in TRx-014-001 were a specific consequence of the gelatine capsule formulation used in the study, and are unlikely to be an inherent feature of the MT moiety itself, if absorbed via the stomach as described.

Example 8—Implications for Improved Compositions and Dosing Regimes

Absorption and Efficacy

As can be seen from the foregoing analysis, the limiting factors in the level of therapeutic efficacy which could be attained using an MTC-based medicinal product are a combination of limitations in absorption and adverse effect limitations. The present section discusses how these limitations could be overcome in the light of the analysis made possible by the development of the integrated pharmacokinetic model.

We first compare the actual dose with the effective dose in FIG. 32, calculated using the same relationship discussed in FIG. 16.

As can be seen, the efficacy-limiting factor is a combination of the limitation in absorption and first-pass metabolism discussed above. These combine to limit severely the benefit which could theoretically be achieved by increasing the dose. Indeed the apparent efficacy plateau suggested above in FIG. 7 is determined almost entirely by the limitation in the effective dose which can be delivered using a medicinal product based on the present form of MTC.

Prior filed unpublished application PCT/GB2007/001103 describes certain stabilised reduced salt forms of the methylthioninium moiety (referred to in what follows as "L-MTx"). We here use the integrated pharmacokinetic model, and the relationship defined by it with therapeutic efficacy observed in TRx-014-001 to determine how this novel composition of matter could be used to optimise treatment of AD based on the methylthioninium moiety.

We first consider the predicted fraction of orally administered L-MTx that would be expected to be absorbed. This is calculated on the basis that the loss due to first-pass metabolism (ie the loss from C6 designated C600 in Table 14 and shown in FIG. 22) would not be eliminated by dosing with the L-MTx form. However, it is expected that the loss due to initial non-absorption from C1 (ie the loss from C1 designated C100 in Table 14 and shown in FIG. 22) would be eliminated by dosing with the L-MTx form. This is because the L-MTx form (particularly the dihydrobromide salt, PCT/GB2007/001103) has more than twice the solubility of MTC, and would be expected to bypass the thiazine-dye reductase (May et al., 2004) which is presumed to exist in the stomach and is presumed to be necessary for absorption. Based on these assumptions, the predicted fraction of dose absorbed, calculated from the data provided by the model is shown in FIG. 33. Specifically, the total pre-central compartment losses amount to 54% of the administered dose for the 100 mg case. Of this total loss, 43% is due to non-absorption from C1. This is applied across doses to estimate the expected bioavailibity of administered L-MTx allowing for loss due to subsequent first-pass metabolism.

Once absorption into the central compartment has occurred, the predicted efficacy can be determined from the relationships described above linking steady state level in C3 or C2 with observed effect size. These are shown for C3 in FIG. 34.

The corresponding relationships between expected clinical efficacy of an L-MTx-based form of the methylthioninium moiety and predicted average steady state level of MT in C2 (blood) for a range of dosing regimes from 1/day to 3/day are shown in FIG. 35.

As can be seen from FIGS. 34 & 35, it is predicted that a level of efficacy of −8.1 ADAS-cog units could be achieved on a dosing regime of 100 mg of the L-MTx form administered twice daily, which could also be achieved by dosing with 60 mg 3 times per day. Even higher efficacy levels would be expected using 100 mg or higher administered 3 times per day.

It is therefore inferred that substantially higher efficacy and superior dosing regime could be achieved using the L-MTx form of the methylthioninium moiety.

Safety and Tolerability of the L-MTx Form of the Methylthioninium Moiety

As discussed above in the section Relationship Between Cognitive and Haematological Activity, a significant limitation in the extent to which higher doses of MTC could be administered to achieve better efficacy is due to the combined consequences of increasing haematolotical side effects and poor tolerability due to diarrhoea. Although it is likely that the L-MTx form would substantially reduce diarrhoea, it is not clear what the expected haematological effects would be.

As shown in FIG. 9 and Table 4 in the section Relationship Between Cognitive and Haematological Activity, it is expected that the L-MTx form would have less haematological side effects based on the rat studies discussed above. Furthermore, as discussed above in the section Correlation between observed and predicted haematological side effects based on the integrated oral human pharmacokinetic model, it is unlikely that the haematological effects are inherent to the MT moiety itself, in the dosage range required for anti-dementia activity. At higher oral doses, shown for example in the rat study above, it is clear that haematological adverse would be seen, but it is unlikely that these doses would be reached in clinical usage of MTC-based forms of a medicinal product.

Given the dose-response relationship observed in the rat study discussed above in the section Relationship Between Cognitive and Haematological Activity, the expected effect on total red cell count can be calculated, as shown in FIG. 36. As can be seen, the expected haematological side effects as indexed by decline in red cell count is expected to be negligible.

Feasibility of Delayed Release Formulation of the L-MTx Form of the Methylthioninium Moiety Whereas, for the reasons discussed above, it would not be feasible to generate a delayed-release formulation of an MTC-based medicinal product, this would not be the case for an L-MTx-based form of the methylthioninium moiety. This is because the leuco-form of the methylthioninium cannot dimerise. This is because it is not a 'flat' molecule (unlike Ox-MT), and it has not charge which permits stabilisation of the dimeric form by charge neutralisation.

Therefore, it is likely that a delayed-release formulation of the L-MTx-based form of the methylthioninium moiety would be feasible without encountering the adverse consequences of delayed absorption. This could be created in a once-daily dosage form.

REFERENCES FOR EXAMPLES 1-8

Birks, J. (2006) Cholinesterase inhibitors for Alzheimer's disease. Cochrane Database Syst. Rev. (1): CD005593.

DiSanto, A. R., Wagner, J. G. (1972a) Pharmacokinetics of highly ionized drugs. I: Methylene blue—whole blood, urine and tissue assays. Journal of Pharmaceutical Sciences, 61:598-602.

DiSanto, A. R., Wagner, J. G. (1972b) Pharmacokinetics of highly ionized drugs. II. Methylene blue—absorption, metabolism, and excretion in man and dog after oral administration. Journal of Pharmaceutical Sciences, 61:1086-1090.

DiSanto, A. R., Wagner, J. G. (1972c) Pharmacokinetics of highly ionized drugs. III. Methylene blue—blood levels in the dog and tissue levels in the rat following intravenous administration. Journal of Pharmaceutical Sciences, 61:1090-1094.

Gunics, G., Motohashi, N., Amaral, L., Farkas, S. & Molnar, J. (2000) Interaction between antibiotics and non-conventional antibiotics on bacteria. International Journal of Antimicrobial Agents 14:239-42.

Kristiansen, J. E., Amaral, L. (1997) The potentional management of resistant infection with non-antibiotics. Journal of Antimicrobial Chemotherapy, 40:319-327.

Lewis, G. N., Bigeleisen, J. (1943) Methylene blue and other indicators in general acids. The acidity function: J. Amer. Chem. Soc., 65:1144-1150.

May, J. M., Qu, Z. C., Cobb, C. E. (2004) Reduction and uptake of methylene blue by human erythrocytes. Am. J. Physiol. Cell Physiol., 286:C1390-C1398.

Merker, M. P., Bongard, R. D., Kettenhofen, N. J., Okamoto, Y., Dawson, C. A. (2002) Intracellular redox status affects transplasma membrane electron transport in pulmonary arterial endothelial cells. Am. J. Physiol. Lung Cell. Mol. Physiol., 282:L36-L43.

Merker, M. P., Olson, L. E., Bongard, R. D., Patel, M. K., Linehan, J. H., Dawson, C. A. (1998) Ascorbate-mediated transplasma membrane electron transport in pulmonary arterial endothelial cells. Am. J. Physiol., 274:L685-L693.

Peter, C., Hongwan, D., Kupfer, A., Lauterburg, B. H. (2000) Pharmacokinetics and organ distribution of intravenous and oral methylene blue. Eur. J. Clin. Pharmacol., 56: 247-250.

Rabinowitch, E., Epstein, L. (1941) Polymerization of dyestuffs in solution. Thionine and methylene blue. J. Am. Chem. Soc. 63:69-78.

Spencer, W., Sutter, J. R. (1979) Kinetic study of the monomer-dimer equilibrium of methylene blue in aqueous suspension. J. Phys. Chem., 83:1573-1576.

Selkoe, D. J. (2004) Cell biology of protein misfolding: the examples of Alzheimer's and Parkinson's diseases. Nat. Cell. Biol., 6:1054-1061.

Moody, J. P., Allan, S. M., Smith, A. H., Naylor, G. J. (1989). Methylene blue excretion in depression. Biol. Psychiatry; 26:850-852.

Rengelshausen, J., Burhenne, J., Frohlich, M., Tayrouz, Y., Singh, S. K., Riedel, K.-D., Muller, O., Hoppe-Tichy, T., Haefeli, W. E., Mikus, G. & Walter-Sack, I. (2004) Pharmacokinetic interaction of chloroquine and methylene blue combination against malaria. European Journal of Clinical Pharmacology 60:709-715.

Wischik, C. M., Lai, R. Y. K., Harrington, C. R. (1997) Modelling prion-like processing of tau protein in Alzheimer's disease for pharmaceutical development. In Microtubule-Associated Proteins: Modifications in Disease. (eds. J. Avila, R. Brandt, & K. S. Kosik) Harwood Academic Publishers, Amsterdam, 185-241.

Gibaldi, M. and Perrier, D. (1982) Pharmacokinetics. 2nd edn. Marcel Dekker Inc., New York.

Braak, H., Braak, E. (1991) Neuropathological staging of Alzheimer-related changes. Acta Neuropathologica 82:239-259.

Kuriloff, D. B., Sanborn, K. V. (2004) Rapid intraoperative localization of parathyroid glands utilizing methylene blue infusion. Otolaryngology—Head & Neck Surgery 131:616-622.

Example 9—Chemical Synthesis of Stable Crystalline Reduced Form DAPTZ Compounds

The following disclosure generally corresponds to that in prior filed, unpublished, application PCT/GB2007/001103

(specifically incorporated by reference) but is included herein for completeness only.

For example, a suitable phenothiazine may be converted to the corresponding 3,7-dinitro-phenothiazine, for example, using sodium nitrite with acetic acid and chloroform. The ring amino group may then be protected, for example, as the acetate, for example, using acetic anhydride and pyridine. The nitro groups may then be reduced to amino groups, for example, using tin (II) chloride with ethanol. The amino groups may then be substituted, for example, disubstituted, for example, methyl disubstituted, for example, using methyl iodide, sodium hydroxide, DMSO, and tetra-n-butyl ammonium bromide. The amino group may then be deprotected, for example, the N-acetyl group may be removed, for example, using concentrated aqueous hydrochloride acid. The corresponding salt is then prepared, for example, using concentrated aqueous hydrochloric acid, for example, at the same time as deprotection. An example of such a method is illustrated in the following scheme.

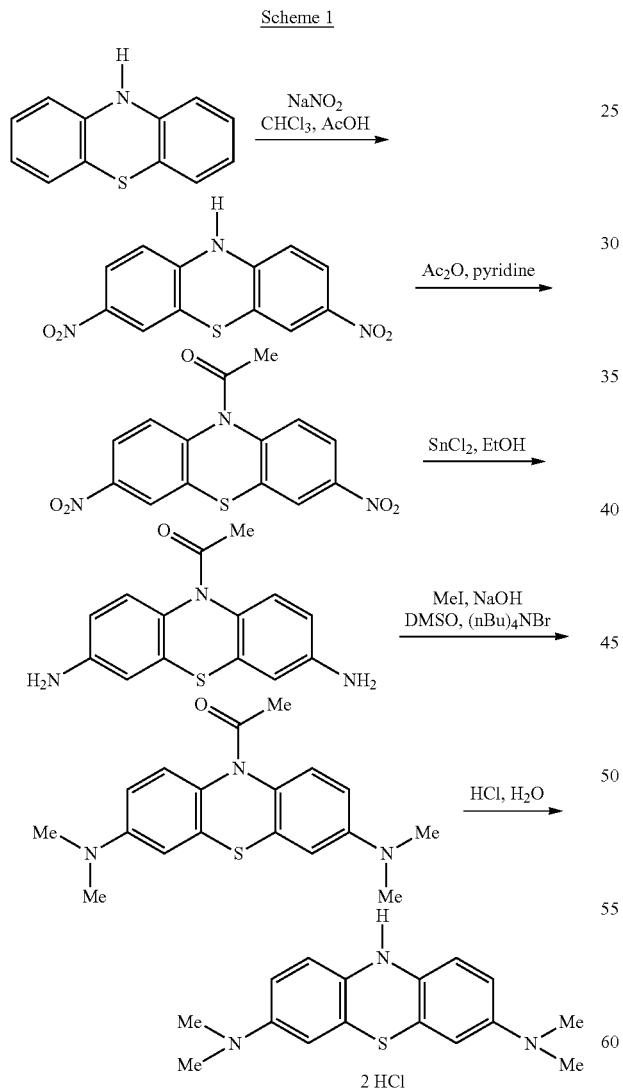

Scheme 1

Thus, another aspect of the invention pertains to a method of preparing a 3,7-diamino-10H-phenothiazine compound of the following formula, for use in the methods of treatment described above:

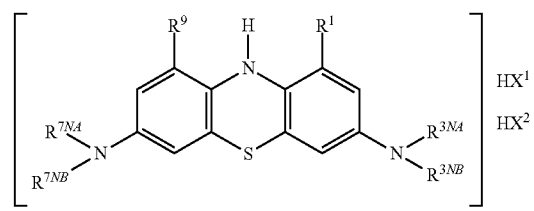

wherein $R^1$, $R^9$, $R^{3NA}$, $R^{3NB}$, $R^{7NA}$, $R^{7NB}$, $HX^1$ and $HX^2$ are as defined herein (for example, where $HX^1$ and $HX^2$ are each HCl), comprising the step of:
(vi) salt formation (SF).

In one embodiment, the method comprises the steps of:
(v) ring amino deprotection (DP); and
(vi) salt formation (SF).

In one embodiment, the method comprises the steps of:
(iv) amine substitution (AS),
optional (v) ring amino deprotection (DP), and
(vi) salt formation (SF).

In one embodiment, the method comprises the steps of
(iii) nitro reduction (NR),
(iv) amine substitution (AS),
(v) ring amino deprotection (DP), and
(vi) salt formation (SF).

In one embodiment, the method comprises the steps of
optional (ii) ring amino protection (AP),
(iii) nitro reduction (NR),
(iv) amine substitution (AS),
(v) ring amino deprotection (DP), and
(vi) salt formation (SF).

In one embodiment, the method comprises the steps of
(i) nitration (NO),
(ii) ring amino protection (AP),
(iii) nitro reduction (NR),
(iv) amine substitution (AS),
(v) ring amino deprotection (DP), and
(vi) salt formation (SF).

In one embodiment, the steps are performed in the order listed (i.e., any step in the list is performed at the same time as, or subsequent to, the preceding step in the list).

In one embodiment, the step of (v) ring amino deprotection (DP) and the step of (vi) salt formation (SF) are performed simultaneously (i.e., as one step).

In one embodiment, the nitration (NO) step is:
(i) nitration (NO), wherein a 10H-phenothiazine is converted to a 3,7-dinitro-10H-phenothiazine, for example:

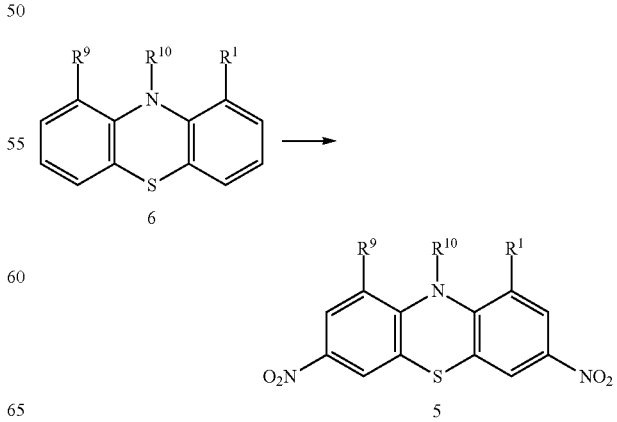

In one embodiment, nitration is performed using a nitrite, for example, sodium nitrite, for example, sodium nitrite with acetic acid and chloroform. In one embodiment, $R^{10}$ is —H.

In one embodiment, the ring amino protection (AP) step is:

(ii) ring amino protection (AP), wherein the ring amino group (—NH—) of a 3,7-dinitro-10H-phenothiazine is converted to a protected ring amino group (—NR$^{prot}$), for example:

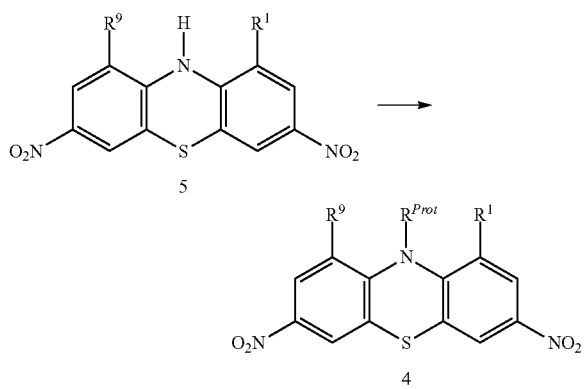

In one embodiment, ring amino protection is achieved as an acetate, for example, using acetic anhydride, for example, using acetic anhydride and pyridine.

In one embodiment, the nitro reduction (NR) step is:

(iii) nitro reduction (NR), wherein each of the nitro (—NO$_2$) groups of a protected 3,7-dinitro-10H-phenothiazine is converted to an amino (—NH$_2$) group, for example:

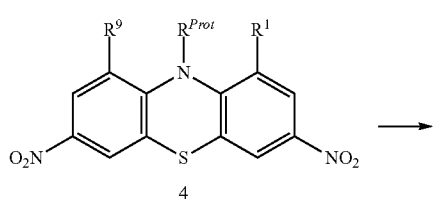

In one embodiment, nitro reduction may be performed using, for example, tin (II) chloride, for example, tin (II) chloride with ethanol.

In one embodiment, the amine substitution (AS) step is:

(iv) amine substitution (AS), wherein each of the amino (—NH$_2$) groups of a protected 3,7-diamino-10H-phenothiazine is converted to disubstituted amino group, for example:

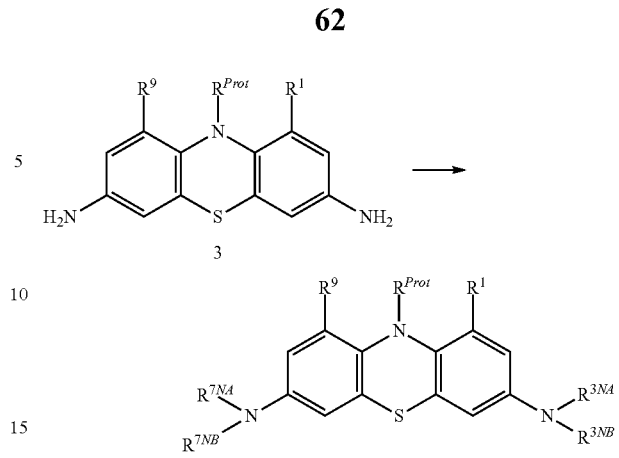

In one embodiment, amine substitution is performed using an alkyl halide, for example, an alkyl iodide, for example, methyl iodide, for example, methyl iodide with sodium hydroxide, DMSO, and tetra-n-butyl ammonium bromide.

In one embodiment, the ring amino deprotection (DP) step is:

(v) ring amino deprotection (DP), wherein the protecting group, $R^{Prot}$, is removed, for example:

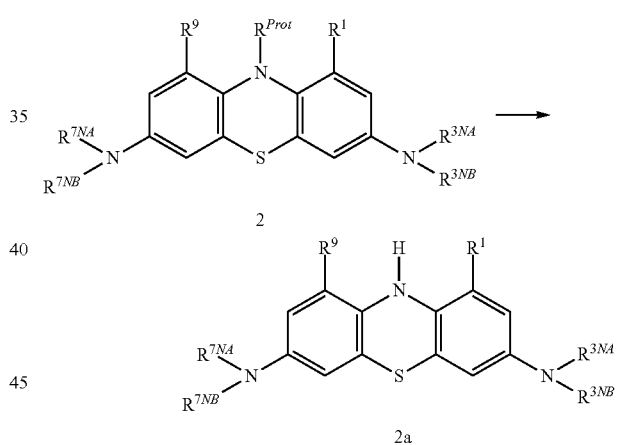

In one embodiment, ring amino deprotection may be performed using acid, for example, hydrochloric acid, for example, concentrated aqueous hydrochloric acid.

In one embodiment, the step is:

(vi) salt formation (SF), wherein the corresponding salt is formed, for example:

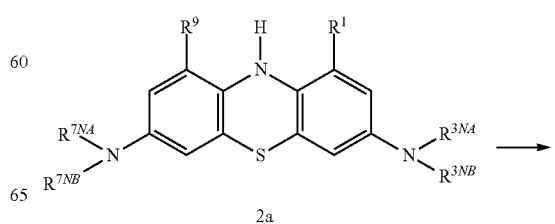

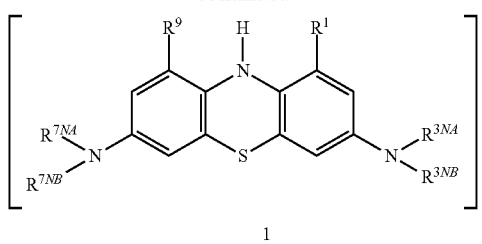

In one embodiment, salt formation may be performed using acid, for example, hydrochloric acid, for example, concentrated aqueous hydrochloric acid.

In one embodiment, the steps of ring amine deprotection and salt formation are performed simultaneously (i.e., as one step), for example, compound (1) is formed from compound (2) in one step.

In another approach, a suitable thioninium chloride (for example, methylthioninium chloride, MTC) is converted to the corresponding halide, for example, by reaction with potassium iodide, for example, aqueous potassium iodide. The resulting thioninium iodide is then reduced, for example, with ethyl iodide and ethanol, and the corresponding salt formed. A similar method is described in Drew, H. D. K, and Head, F. S. H., "Derivatives of Methylene-blue," Journal of the Chemical Society, 1933, pp. 248-253. An example of such a method is illustrated in the following scheme.

Scheme 2

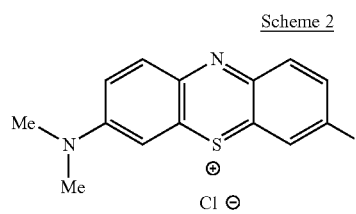

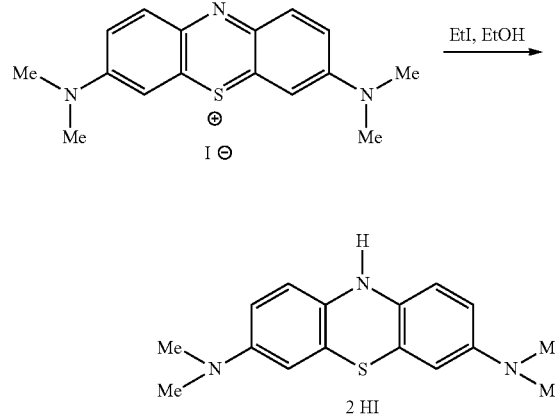

Thus, another aspect of the invention pertains to a method of preparing a DAPTZ compound of the following formula, for use in the methods of treatment described above:

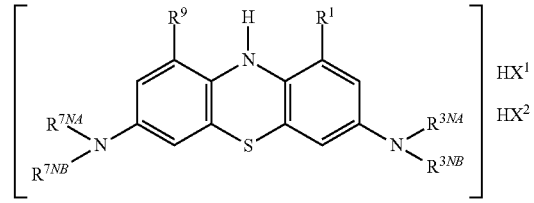

wherein $R^1$, $R^9$, $R^{3NA}$, $R^{3NB}$, $R^{7NA}$, $R^{7NB}$, $HX^1$ and $HX^2$ are as defined herein (for example, where $HX^1$ and $HX^2$ are each HI), comprising the step of:
(ii) reduction and iodide salt formation (RISF).

In one embodiment, the method comprises the steps of:
(i) iodide exchange (IE); and
(ii) reduction and iodide salt formation (RISF).

In one embodiment, the steps are performed in the order listed (i.e., any step in the list is performed at the same time as, or subsequent to, the preceding step in the list).

In one embodiment, the iodide exchange (IE) step is:
(i) iodide exchange (IE), wherein a 3,7-di(disubstituted amino)-thioninium salt is converted to the corresponding 3,7-di(disubstituted amino)-thioninium iodide, for example (where r is an anionic counter ion, for example, halide, for example, chloride or bromide):

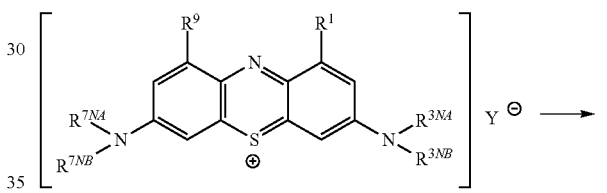

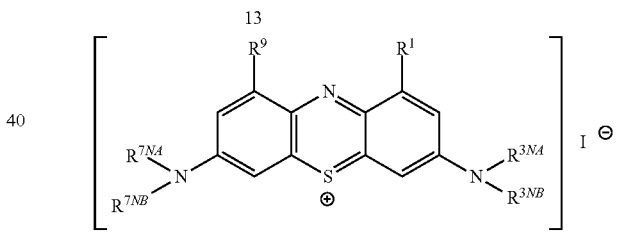

In one embodiment, iodide exchange (IE) is achieved by reaction with potassium iodide, for example, aqueous potassium iodide.

In one embodiment, the reduction and iodide salt formation (RISF) step is:
(ii) reduction and iodide salt formation (RISF), wherein a 3,7-di(disubstituted amino)-thioninium iodide is reduced and converted to the corresponding 3,7-diamino-10H-phenothiazine iodide compound, for example:

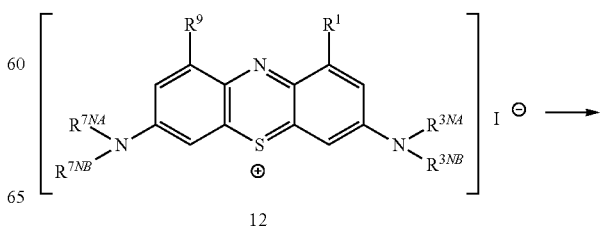

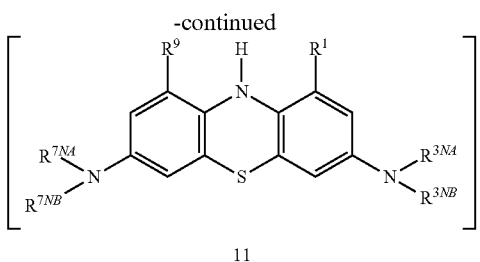

In one embodiment, reduction and iodide salt formation (RISF) is achieved by reaction with ethyl iodide, for example, ethyl iodide and ethanol.

In another approach, an appropriate thioninium salt, for example, ethyl thioninium semi zinc chloride, is simultaneously reduced and the ring amino group protected, for example, by reaction with phenylhydrazine, ethanol, acetic anhydride, and pyridine. The corresponding salt may then be prepared, for example, using concentrated aqueous hydrochloric acid, for example, at the same time as deprotection. An example of such a method is illustrated in the following scheme.

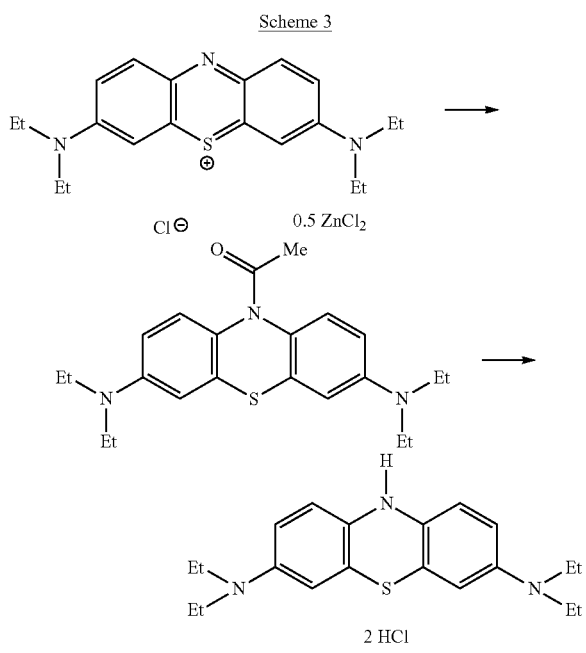

Thus, another aspect of the invention pertains to a method of preparing a 3,7-diamino-10H-phenothiazine (DAPTZ) compound of the following formula:

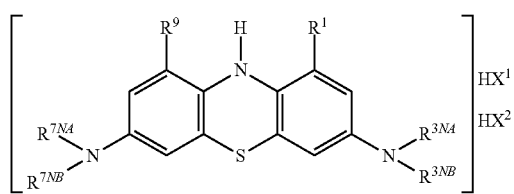

wherein $R^1$, $R^9$, $R^{3NA}$, $R^{3NB}$, $R^{7NA}$, $R^{7NB}$, $HX^1$ and $HX^2$ are as defined herein (for example, where $HX^1$ and $HX^2$ are each HI), comprising the step of:

comprising the step of:
(iv) salt formation (SF).

In one embodiment, the method comprises the steps of
(iii) ring amino deprotection (DP), and
(iv) salt formation (SF).

In one embodiment, the method comprises the steps of
(ii) ring amino protection (AP),
(iii) ring amino deprotection (DP), and
(iv) salt formation (SF).

In one embodiment, the method comprises the steps of
(i) reduction (RED)
(ii) ring amino protection (AP),
(iii) ring amino deprotection (DP), and
(iv) salt formation (SF).

In one embodiment, the steps are performed in the order listed (i.e., any step in the list is performed at the same time as, or subsequent to, the preceding step in the list).

In one embodiment, the step of (i) reduction (RED) and the step of (ii) ring amino protection (AP) are performed simultaneously (i.e., as one step).

For example, in one embodiment, the combined reduction (RED) step and ring amino protection (AP) step is:
(i) reduction (RED) and ring amino protection (AP), wherein a 3,7-di(disubstituted amino)-thioninium salt is reduced to give the corresponding 3,7-di(disubstituted amino)-10H-phenothiazine, and the ring amino group (—NH—) of the 3,7-di(disubstituted amino)-10H-phenothiazine is converted to a protected ring amino group (—$R^{prot}$) to give the corresponding protected 3,7-di(disubstituted amino)-10H-phenothiazine, for example:

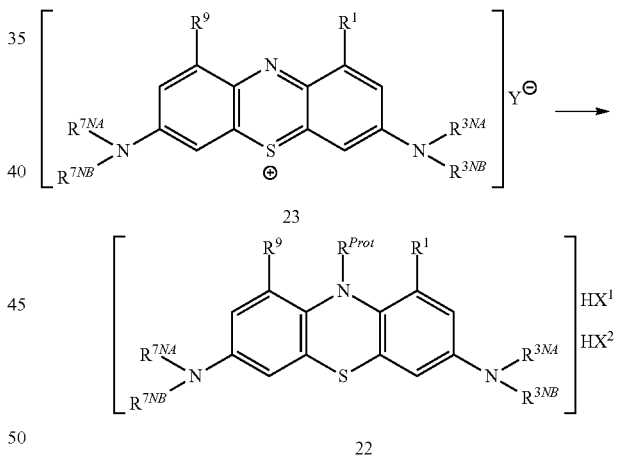

In one embodiment, Y represents Cr.

In one embodiment, the combined reduction (RED) step and ring amino protection (AP) step is achieved using phenylhydrazine and acetic anhydride, for example, phenylhydrazine, ethanol, acetic anhydride, and pyridine.

In one embodiment, the step of (iii) ring amino deprotection (DP) and the step of (iv) salt formation (SF) are performed simultaneously (i.e., as one step).

For example, in one embodiment, the combined ring amino deprotection (DP) step and salt formation (SF) step is:
(ii) ring amino deprotection (DP) and salt formation (SF), wherein the protecting group of a protected 3,7-di(disubstituted amino)-10H-phenothiazine is removed to give a 3,7-di(disubstituted amino)-10H-phenothiazine, and the corresponding salt is formed, for example:

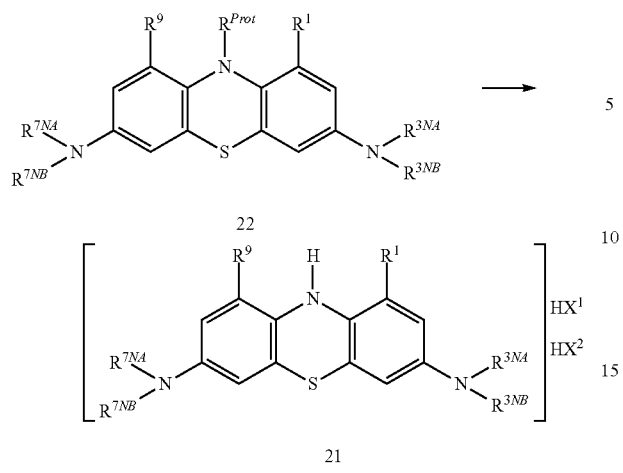

In one embodiment, the combined ring amino deprotection (DP) step and salt formation (SF) step may be performed using acid, for example, hydrochloric acid, for example, concentrated aqueous hydrochloric acid.

In a similar approach, an appropriate thioninium chloride (e.g., methyl thioninium chloride, ethyl thioninium chloride) is first reduced and acetylated to give the corresponding 1-(3,7-bis-dimethylamino-phenothiazin-10-yl)-ethanone, for example, by reaction with hydrazine ($NH_2NH_2$), methyl hydrazine ($MeNHNH_2$), or sodium borohydride ($NaBH_4$); and acetic anhydride (($H_3CCO)_2O$); for example, in the presence of a suitable base, for example, pyridine ($C_5H_5N$) or Hunig's base (diisopropylethylamine, $C_8H_{19}N$), for example, in a suitable solvent, for example, ethanol or acetonitrile. The reduced and acetylated compound is then deprotected (by removing the acetyl group), for example, by reaction with a suitable halic acid, for example, hydrochloric acid or hydrobromic acid, in a suitable solvent, for example, ethanol, and optionally with the addition of a suitable ether, for example, diethyl ether.

Specific examples are as follows:

Chemical Synthesis

Synthesis 1

3-Nitro-10H-phenothiazine

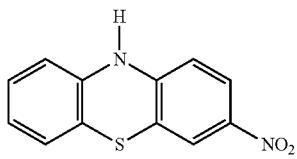 [SMILES: O=[N+]([O-])c1ccc2c(c1)Sc1ccccc1N2]

Sodium nitrite (20.00 g, 210 mmol) was added to a mixture of 10H-phenothiazine (20.00 g, 50 mmol), chloroform (100 cm³), and acetic acid (20 cm³), and the mixture was stirred for 1 hour at room temperature. Acetic acid (20 cm³) was then added and the mixture was stirred for a further 18 hours. The suspension was filtered and washed with acetic acid, ethanol, water, and finally ethanol to give a purple/brown solid. The residue was dissolved in hot DMF and allowed to cool before filtering the di-nitro compound as a purple solid. Concentration of the DMF solution and washing the precipitate with water and methanol gave the title mono-nitro compound (15 g, ~50%) as a brown solid; $v_{max}$ (KBr)/cm$^{-1}$: 3328 (NH), 3278 (NH), 3229 (NH), 3119 (CH), 3049 (CH), 1557 ($NO_2$), 1531 ($NO_2$); $\delta_H$ (250 MHz; DMSO): 6.64 (5H, m, ArH), 7.68 (1H, d, J 2.5, ArH), 7.79-7.84 (1H, dd, J 2.75, 6.5, ArH); $\delta_C$ (62.9 MHz; DMSO): 113.3 (ArC), 115.3 (ArC), 116.9 (ArC), 121.8 (ArC), 123.6 (ArC), 123.7 (ArC), 124.6 (ArC), 126.4 (ArC), 128.1 (ArC), 138.8 (ArC), 141.0 (ArC), 147.8 (ArC).

Synthesis 2

3,11-Dinitro-10H-phenothiazine

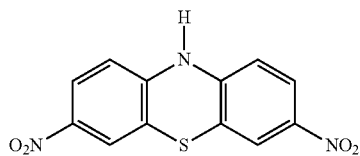 [SMILES: O=[N+]([O-])c1ccc2c(c1)Sc1cc([N+](=O)[O-])ccc1N2]

The procedure for the synthesis of 3-nitro-10H-phenothiazine was followed using 3-nitro-10H-phenothiazine (10.00 g, 41 mmol), chloroform (40 cm³), acetic acid (2×10 cm³), and sodium nitrite (11.86 g, 173 mmol). The residue obtained was recrystallised from DMF to yield the title di-nitro compound (6.60 g 56%) as purple needles; $v_{max}$ (KBr)/cm$^{-1}$: 3331 (NH), 3294 (NH), 3229 (NH), 3101 (CH), 3067 (CH), 1602 ($NO_2$), 1558 ($NO_2$); $\delta_H$ (250 MHz; DMSO): 6.73-6.76 (2H, d, J 9, ArH), 7.78 (2H, s, ArH), 7.89-7.85 (2H, d, J 9, ArH).

Synthesis 3

1-(3,7-Dinitro-phenothiazin-10-yl)-ethanone

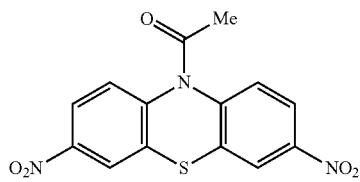

A solution of 3,11-dinitro-10H-phenothiazine (3.00 g, 10.37 mmol), acetic anhydride (15.88 g, 155.50 mmol), and pyridine (30 cm³) was stirred at reflux for 18 hours. The warm solution was then carefully poured over ice water. A precipitate formed and was filtered, dissolved in dichloromethane, dried over magnesium sulphate, filtered, and concentrated to give a brown/orange solid, which was purified by column chromatography ($SiO_2$, ethyl acetate:petroleum ether, 2:3, loaded as a dichloromethane solution) to give the title compound (2.46 g, 71%) as a light yellow solid which can be recrystallised from acetone to give light yellow needles; $v_{max}$ (KBr)/cm$^{-1}$: 3091 (CH), 3063 (CH), 1680 (C=O), 1575 ($NO_2$), 1510 ($NO_2$); $\delta_H$ (250 MHz; CDCl$_3$): 2.28 (3H, s, $CH_3$), 7.65-7.69 (2H, d, J 9, ArH), 8.22-8.26 (2H, dd, J 2.75, 8.75, ArH), 8.33-8.32 (2H, d, J 2.5, ArH); $\delta_C$ (62.9 MHz; CDCl$_3$): 168.2 (C=O), 146.3 (ArC), 143.3 (ArC), 133.6 (ArC), 127.8 (ArC), 123.4 (ArC), 122.9 (ArC), 23.1 ($CH_3$); m/z (ES) 331.0 (80%, [M]$^+$).

Synthesis 4

1-(3,7-Diamino-phenothiazin-10-yl)-ethanone

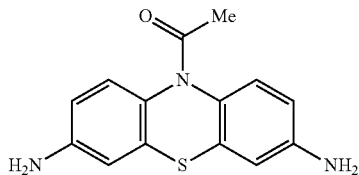 [SMILES: CC(=O)N1c2ccc(N)cc2Sc2cc(N)ccc21]

A mixture of 1-(3,7-dinitro-phenothiazin-10-yl)-ethanone (2 g, 6.04 mmol), tin (II) chloride dihydrate (14.17 g, 62.8 mmol), and ethanol (50 cm$^3$) was heated to reflux and stirred at this temperature for 5 hours. The mixture was then cooled to room temperature and poured over ice water. The pH was adjusted to 7 with 5% sodium hydrogen carbonate before the product was extracted with ethyl acetate (3×50 cm$^3$). The extracts were washed with brine and dried over magnesium sulphate, filtered, and concentrated to give the title compound (1.64 g, 100%) as a purple blue solid; $v_{max}$ (KBr)/cm$^{-1}$: 3445 (NH), 3424 (NH), 3368 (NH), 3322 (NH), 3203 (NH), 3054 (CH), 2995 (CH), 1706 (C=O), 1650 (NO$_2$), 1590 (NO$_2$); 5H (250 MHz; CDCl$_3$): 2.01 (3H, s, CH$_3$), 5.09-5.43 (4H, brd s, NH), 6.47-6.51 (2H, dd, J 1.5, 8.25, ArH), 6.61 (2H, s, ArH), 7.11-7.15 (2H, d, J 8, ArH); $\delta_C$ (62.9 MHz; CDCl$_3$): 169.1 (C=O), 147.2 (ArC), 128.1 (ArC), 127.6 (ArC), 127.3 (ArC), 112.3 (ArC), 111.5 (ArC), 22.6 (CH$_3$); m/z (ES) 293.9 (95%, [M+H, Na]$^+$), 272.0 (20%, [M+H]$^+$), 227.9 (100%, [M+H, -Ac]$^+$).

Synthesis 5

3,7-Diamino-phenothiazine bis(hydrogen chloride) (B4)

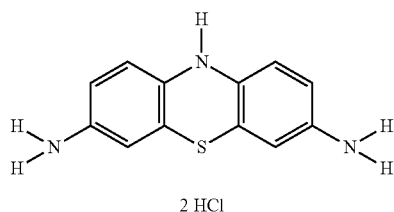 [SMILES: Nc1ccc2c(c1)Sc1cc(N)ccc1N2]

2 HCl 1-(3,7-Diamino-phenothiazin-10-yl)-ethanone (0.25 g, 0.921 mmol) was dissolved in aqueous hydrochloric acid (5 N, 10 cm$^3$) and the solution was heated to reflux and stirred for 30 minutes. Concentration of the reaction mixture gave the title compound as a light blue solid. $\delta_H$ (250 MHz; D$_2$O): 6.60 (2H, brd d, ArH), 7.07 (4H, brd s, ArH).

Synthesis 6

1-(3,7-Bis-dimethylamino-phenothiazin-10-yl)-ethanone

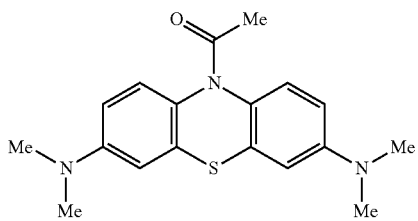 [SMILES: CC(=O)N1c2ccc(N(C)C)cc2Sc2cc(N(C)C)ccc21]

1-(3,7-Diamino-phenothiazin-10-yl)-ethanone (0.25 g 0.92 mmol) was dissolved in DMSO (3 cm$^3$). Toluene (10 cm$^3$), iodomethane (1.96 g, 13.8 mmol), tetrabutylammonium bromide (50 mg), and finally aqueous sodium hydroxide solution (50%, 1.25 cm$^3$) were added. The mixture was stirred at room temperature for 2 hours. Additional aqueous sodium hydroxide (50%, 1.25 cm$^3$) and iodomethane (1.96 g, 13.8 mmol) were then added. The mixture was allowed to stir for a further 3 hours at room temperature before a third aliquot of aqueous sodium hydroxide (50%, 1.25 cm$^3$) and iodomethane (1.96 g, 13.8 mmol) were added and the mixture stirred for a further 18 hours. The thick suspension was washed with water (3×75 cm$^3$) and the toluene extract collected. The water was extracted with dichloromethane (3×50 cm$^3$) and the extracts combined with the toluene, and dried over magnesium sulphate, filtered, and concentrated to give a deep purple solid. The residue was purified by column chromatography (SiO$_2$, ethyl acetate:petroleum ether, 2:3, loaded as a dichloromethane solution) to give the title compound product (0.12 g, 40%) as a light purple solid; $v_{max}$ (KBr)/cm$^{-1}$: 2910 (CH), 2876 (CH), 2856 (CH), 2799 (CH), 1659 (C=O), 1596 (NO$_2$), 1502 (NO$_2$); $\delta_H$ (250 MHz; CDCl$_3$): 2.16 (3H, s, CH$_3$), 2.93 (12H, s, NCH$_3$), 6.59-6.62 (2H, d, J 8.5, ArH), 6.69-6.71 (2H, d, J 2.75, ArH), 7.08-7.47 (2H, brd s, ArH); $\delta_C$ (62.9 MHz; CDCl$_3$): 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$).

Synthesis 7

N,N,N',N'-Tetramethyl-10H-phenothiazine-3,7-diamine bis(hydrogen chloride) (B3)

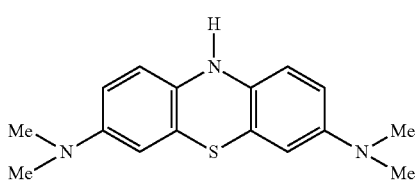

2 HCl 1-(3,7-Bis-dimethylamino-phenothiazin-10-yl)-ethanone (0.5 g, 1.84 mmol) was dissolved in aqueous hydrochloric acid (5 N, 15 cm$^3$), and the solution was heated to reflux temperature and stirred for 30 minutes. Concentration of the reaction mixture gave the title compound as a green/blue solid; $\delta_H$ (250 MHz; D$_2$O): 3.18 (12H, s, NCH$_3$), 6.67 (2H, d, J 8.5, ArH), 7.16 (4H, brd s, ArH); $\delta_C$(62.9 MHz; D$_2$O): 144.3 (ArC), 138.9 (ArC), 122.4 (ArC), 120.8 (ArC), 120.7 (ArC), 117.6 (ArC), 48.9 (NCH$_3$).

Synthesis 8

Methylthioninium Iodide

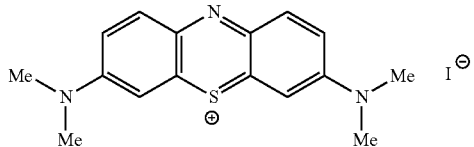 [SMILES: CN(C)c1ccc2nc3ccc(N(C)C)cc3[s+]c2c1 ; [I-]]

To a round bottom flask was added methylthioninium chloride (MTC, Methylene Blue) (2 g, 6.25 mmol) and water (50 cm$^3$) and the mixture stirred for 10 minutes or until the solid dissolved. Potassium iodide (1.56 g, 9.4 mmol) was then added to the mixture and a green black suspension formed. The reaction was heated to boiling and allowed to cool naturally giving the title compound (2.03 g, 79%) as bright green needles. Anal. Calcd for C$_{16}$H$_{18}$N$_3$SI: C, 46.72; H, 4.41; N, 10.22; S, 7.80; I, 30.85. Found: C, 46.30; H, 4.21; N, 10.14; S, 7.86; I, 29.34.

Synthesis 9

N,N,N',N'-Tetramethyl-10H-phenothiazine-3,7-diamine bis(hydrogen iodide) (B6)

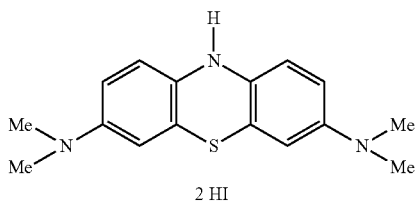 [SMILES: CN(C)c1ccc2c(c1)Sc1cc(N(C)C)ccc1N2]

To a round bottom flask was added methylthioninium iodide (2 g, 4.86 mmol), ethanol (100 cm$^3$) and ethyl iodide (75.8 g, 486 mmol) and the mixture was heated at reflux for 18 hours where the colour changed from green/blue to brown with a yellow precipitate. Once cooled to room temperature, the mixture was filtered and washed with diethylether (20 cm$^3$) to give the title compound (1.99 g, 76%) as a light green solid. $\delta_H$ (250 MHz; D$_2$O): 3.20 (12H, s, NCH$_3$), 6.76 (2H, d, J 8.5, ArH), 7.22 (2H, brd s, ArH); $\delta_C$ (62.9 MHz; D$_2$O): 145.0 (ArC), 139.3 (ArC), 122.6 (ArC), 121.1 (ArC), 120.9 (ArC), 117.9 (ArC), 48.9 (NCH$_3$).

Synthesis 10

1-(3,7-Bis-diethylamino-phenothiazin-10-yl)-ethanone

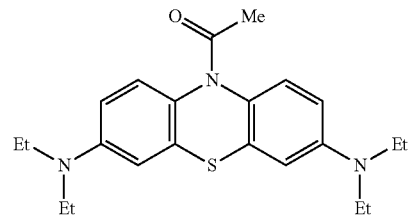 [SMILES: CCN(CC)c1ccc2c(c1)Sc1cc(N(CC)CC)ccc1N2C(C)=O]

To a dry 25 cm$^3$ round bottom flask was added ethylthioninium zinc chloride (0.5 g, 1.13 mmol) and ethanol (10 cm$^3$). Phenylhydrazine (0.134 g, 1.24 mmol) was then added dropwise under an atmosphere of nitrogen. The mixture was stirred 25° C. for 1 hour and concentrated under high vacuum. Pyridine (50 cm$^3$) and acetic anhydride was added and the mixture stirred for 18 hours at 60° C. The solution was opened to ice/water (250 cm$^3$) and the organics were extracted into ethyl acetate (3×50 cm$^3$). The extracts were washed with saturated copper sulphate solution and dried over magnesium sulphate, filtered, and concentrated to give the crude product as a brown oil, which was purified using flash column chromatography with an eluent of 40% ethylacetate:60% petroleum spirit 40-60° C. and silica 40-63µ 60 Å to give the title compound (0.18 g, 41%) as a green glassy solid. $\delta_H$ (250 MHz; CDCl$_3$): 7.0-7.5 (2H, brds, ArH), 6.64 (2H, s, ArH), 6.52 (2H, d, ArH), 3.35 (8H, q, 7, NCH$_2$), 2.18 (3H, s, CH$_3$), 1.16 (12H, t, 7, CH$_3$); $\delta_C$ (62.9 MHz; CDCl$_3$): 12.5 (CH$_3$), 22.9 (CH$_3$), 44.6 (NCH$_2$), 110.1 (ArC), 127.4 (ArC), 146.5 (ArC), 170.2 (C=O).

Synthesis 11

N,N,N',N'-Tetraethyl-10H-phenothiazine-3,7-diamine bis(hydrogen chloride)

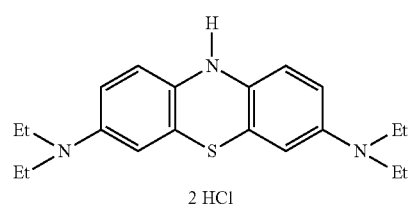 [SMILES: CCN(CC)c1ccc2c(c1)Sc1cc(N(CC)CC)ccc1N2]

To a 25 cm$^3$ round bottom flask was added 3,7-diethylamino-10-acetyl-phenothiazine (0.125 g, 0.33 mmol) and aqueous hydrochloric acid (5 M, 5 cm$^3$). The mixture was heated at 100° C. for 2 hours before cooling to room temperature and was concentrated to give the title compound (0.11 g, 81%) as a yellow green glassy solid. $\delta_H$ (250 MHz; CD$_3$OD): 7.07 (4H, brd, ArH), 6.65 (2H, brd, ArH), 3.35 (8H, brd, NCH$_2$), 0.97 (12H, brd, CH$_3$); $\delta_C$ (62.9 MHz; CD$_3$OD): 10.8 (CH$_3$), 55.1 (NCH$_2$), 116.6 (ArC), 120.4 (ArC), 121.5 (ArC), 123.6 (ArC), 132.6 (ArC), 144.5 (ArC).

Synthesis 12

1-(3,7-Bis-dimethylamino-phenothiazin-10-yl)-ethanone

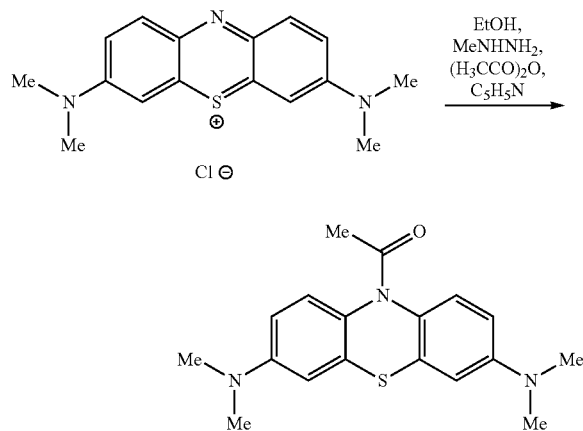 [SMILES: CN(C)c1ccc2nc3ccc(N(C)C)cc3[s+]c2c1 ; [Cl-] ; CC(=O)N1c2ccc(N(C)C)cc2Sc2cc(N(C)C)ccc21]

Synthesis using methylhydrazine/pyridine in two pots. To a 250 cm³ round bottom flask placed under an atmosphere of argon was added methylthioninium chloride trihydrate (26.74 mmol, 10 g), ethanol (100 cm³) and methylhydrazine (58.83 mmol, 2.71 g). The mixture was heated to 40° C. and stirred for 2 hours. The yellow/green suspension was cooled to 5° C. and filtered under argon, washed with ethanol (20 cm³) and dried to give leuco-methylene blue as a light green solid. To the leuco product was added acetic anhydride (40 cm³) and pyridine (10 cm³) and the solution was heated at 100° C. for 18 hours. The cooled mixture was then poured carefully over ice water while stirring to give a precipitate, which was filtered, washed with water, and dried at 60° C. for 2 hours to yield the title compound (5.82 g, 66%) as a light brown solid. Mp 137° C.; $v_{max}$(KBr)/cm⁻¹ 2910 (CH), 2876 (CH), 2856 (CH), 2799 (CH), 1659 (C=O), 1596 (NO₂), 1502 (NO₂); $\delta_H$ (250 MHz; CDCl₃) 2.16 (3H, s, CH₃), 2.93 (12H, s, NCH₃), 6.59-6.62 (2H, d, J 8.5, ArH), 6.69-6.71 (2H, d, J 2.75, ArH), 7.08-7.47 (2H, brd s, ArH); $\delta_C$ (62.9 MHz; CDCl₃) 170.3 (C=O), 148.9 (ArC), 127.2 (ArC), 127.1 (ArC), 127.0 (ArC), 110.9 (ArC), 110.7 (ArC), 40.7 (NCH₃), 22.9 (CH₃); m/z (ES) 284.2 (100%, [M−OAc]⁺), 328.1 (15%, [M+H]⁺), 350.1 (41%, [M+Na]⁺).

Synthesis 13

1-(3,7-Bis-dimethylamino-phenothiazin-10-yl)-ethanone

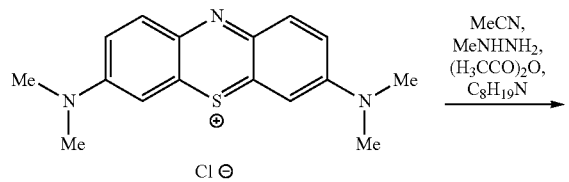

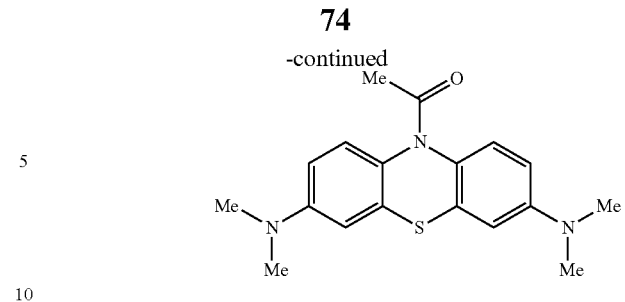

Synthesis using methylhydrazine/Hunig's base in one pot. To a 5000 cm³ reactor vessel under an atmosphere of nitrogen was added methylthioninium chloride trihydrate (0.54 mol, 200 g) and acetonitrile (1000 cm³). Methylhydrazine (1.07 mol, 49.36 g) was added dropwise at 1.5 mL per minute. The temperature of the mixture increased to 32° C. and was stirred for 20 minutes. The yellow/green suspension had acetic anhydride (5.35 mol, 541 g) added and then Hunig's base (diisopropylethylamine) (1.55 mol, 200 g) was added. The mixture was heated at 90° C. for 2 hours. The cooled mixture was then poured carefully into ice water (2000 cm³) in ten 200 cm³ portions while stirring to give a precipitate. The precipitate was stirred for 45 minutes before it was filtered, washed with water (3×250 cm³). and air dried for 30 minutes. The crude material was crystallised from hot ethanol (2750 cm³) to yield the title compound (112.1 g, 64%) as a light grey solid. Mp 137° C.; $v_{max}$(KBr)/cm⁻¹ 2910 (CH), 2876 (CH), 2856 (CH), 2799 (CH), 1659 (C=O), 1596 (NO₂), 1502 (NO₂); $\delta_H$ (250 MHz; CDCl₃) 2.16 (3H, s, CH₃), 2.93 (12H, s, NCH₃), 6.59-6.62 (2H, d, J 8.5, ArH), 6.69-6.71 (2H, d, J 2.75, ArH), 7.08-7.47 (2H, brd s, ArH); $\delta_C$ (62.9 MHz; CDCl₃) 170.3 (C=O), 148.9 (ArC), 127.2 (ArC), 127.1 (ArC), 127.0 (ArC), 110.9 (ArC), 110.7 (ArC), 40.7 (NCH₃), 22.9 (CH₃); m/z (ES) 284.2 (100%, [M−OAc]⁺), 328.1 (15%, [M+H]⁺), 350.1 (41%, [M+Na]⁺).

Synthesis 14

1-(3,7-Bis-dimethylamino-phenothiazin-10-yl)-ethanone

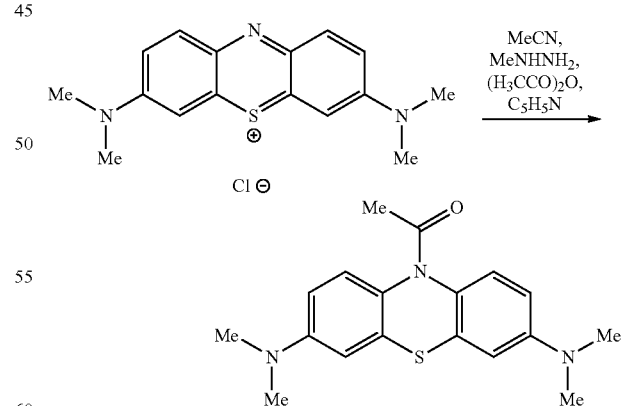

Synthesis using methylhydrazine/pyridine in one pot. To a 250 cm³ round bottom flask under an atmosphere of nitrogen was added methylthioninium chloride trihydrate (26.74 mmol, 10 g) and acetonitrile (50 cm³). Methylhydrazine (53.5 mmol, 2.46 g) was added in four equal portions over a 30 minutes time period. The temperature of the mixture was maintained at 35° C. with a cold water bath and was stirred for 30 minutes. The yellow/green suspension had acetic anhydride (267 mmol, 27.3 g) and pyridine (80.2 mmol, 6.35 g) was added. The mixture was heated at 90° C. for 2 hours. The cooled mixture was then poured carefully into ice water (200 cm³) in ten equal portions while stirring to give a precipitate. The precipitate was stirred for 30 minutes before it was filtered, washed with water (3×50 cm³) and air dried for 30 minutes. The crude material was crystallised from hot ethanol (120 cm³) to yield the title compound (5.97 g, 68%) as a light grey solid. Mp 137° C.; $v_{max}$(KBr)/cm$^{-1}$ 2910 (CH), 2876 (CH), 2856 (CH), 2799 (CH), 1659 (C=O), 1596 (NO$_2$), 1502 (NO$_2$); 5H (250 MHz; CDCl$_3$) 2.16 (3H, s, CH$_3$), 2.93 (12H, s, NCH$_3$), 6.59-6.62 (2H, d, J 8.5, ArH), 6.69-6.71 (2H, d, J 2.75, ArH), 7.08-7.47 (2H, brd s, ArH); $\delta_C$ (62.9 MHz; CDCl$_3$) 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$); m/z (ES) 284.2 (100%, [M−OAc]$^+$), 328.1 (15%, [M+M]$^+$), 350.1 (41%, [M+Na]$^+$).

Synthesis 15

1-(3,7-Bis-dimethylamino-phenothiazin-10-yl)-ethanone

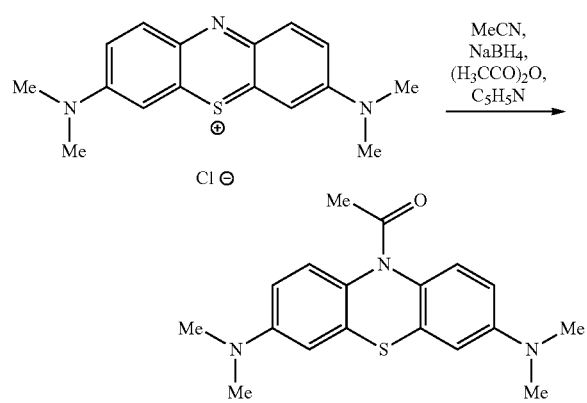

Synthesis using sodium borohydride/pyridine in one pot. To a 500 cm³ round bottom flask under an atmosphere of nitrogen was added methylthioninium chloride trihydrate (0.134 mol, 50 g) and acetonitrile (250 cm³). Sodium borohydride (0.174 mol, 6.6 g) was added in four equal portions over a 30 minute time period. The temperature of the mixture was maintained at 35° C. with a cold water bath and was stirred for 30 minutes. The yellow/green suspension had acetic anhydride (0.535 mol, 55 g) and pyridine (0.174 mol, 13.76 g) added. The mixture was heated at 90° C. for 2 hours. The cooled mixture was then poured carefully into ice water (250 cm³) in ten equal portions while stirring to give a precipitate. The precipitate was stirred for 30 minutes before it was filtered, washed with water (3×50 cm³), and air dried for 30 minutes. The crude material was crystallised from hot ethanol (500 cm³) to yield the title compound (26.7 g, 61%) as a light grey solid. Mp 137° C.; $v_{max}$(KBr)/cm$^{-1}$ 2910 (CH), 2876 (CH), 2856 (CH), 2799 (CH), 1659 (C=O), 1596 (NO$_2$), 1502 (NO$_2$); $\delta_H$ (250 MHz; CDCl$_3$) 2.16 (3H, s, CH$_3$), 2.93 (12H, s, NCH$_3$), 6.59-6.62 (2H, d, J 8.5, ArH), 6.69-6.71 (2H, d, J 2.75, ArH), 7.08-7.47 (2H, brd s, ArH); $\delta_C$ (62.9 MHz; CDCl$_3$) 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$); m/z (ES) 284.2 (100%, [M−OAc]$^+$), 328.1 (15%, [M+H]$^+$), 350.1 (41%, [M+Na]$^+$).

Synthesis 16

1-(3,7-Bis-dimethylamino-phenothiazin-10-yl)-ethanone

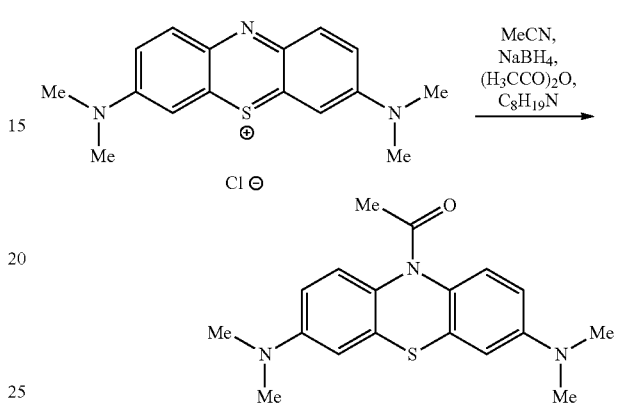

Synthesis using sodium borohydride/Hunig's base in one pot. To a 500 cm³ round bottom flask under an atmosphere of nitrogen was added methylthioninium chloride trihydrate (80.2 mmol, 30 g) and acetonitrile (150 cm³). Sodium borohydride (104 mmol, 3.94 g) was added in four equal portions over a 30 minute time period. The temperature of the mixture was maintained at 35° C. with a cold water bath and was stirred for 30 minutes. The yellow/green suspension had acetic anhydride (321 mmol, 32.75 g) and Hunig's base (diisopropylethylamine) (120 mmol, 15.55 g) added. The mixture was heated at 90° C. for 2 hours. The cooled mixture was then poured carefully into ice water (200 cm³) in ten equal portions while stirring to give a precipitate. The precipitate was stirred for 30 minutes before it was filtered, washed with water (3×50 cm³), and air dried for 30 minutes. The crude material was crystallised from hot ethanol (300 cm³) to yield the title compound (13.55 g, 52%) as a light grey solid. Mp 137° C.; $v_{max}$(KBr)/cm$^{-1}$ 2910 (CH), 2876 (CH), 2856 (CH), 2799 (CH), 1659 (C=O), 1596 (NO$_2$), 1502 (NO$_2$); $\delta_H$ (250 MHz; CDCl$_3$) 2.16 (3H, s, CH$_3$), 2.93 (12H, s, NCH$_3$), 6.59-6.62 (2H, d, J 8.5, ArH), 6.69-6.71 (2H, d, J 2.75, ArH), 7.08-7.47 (2H, brd s, ArH); $\delta_C$ (62.9 MHz; CDCl$_3$) 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$); m/z (ES) 284.2 (100%, [M−OAc]$^+$), 328.1 (15%, [M+H]$^+$), 350.1 (41%, [M+Na]$^+$).

Synthesis 17

1-(3,7-Bis-dimethylamino-phenothiazin-10-yl)-ethanone

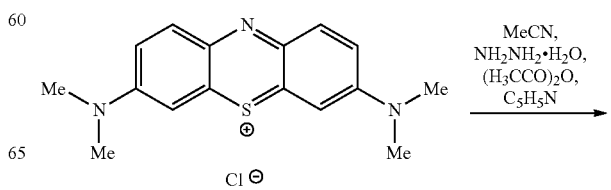

-continued

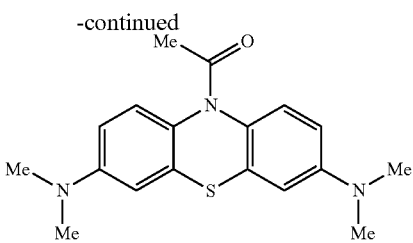

Synthesis using hydrazine monohydrate/pyridine in one pot. To a 250 cm³ round bottom flask under an atmosphere of nitrogen was added methylthioninium chloride trihydrate (26.74 mmol, 10 g) and acetonitrile (50 cm³). Hydrazine monohydrate (58.8 mmol, 2.95 g) was added and the mixture was heated to reflux and stirred for 10 minutes before cooling to 25° C. The yellow/green suspension had acetic anhydride (424 mmol, 43.3 g) and pyridine (124 mmol, 9.78 g) added. The mixture was heated at 90° C. for 2 hours. The cooled mixture was then poured carefully into ice water (100 cm³) in ten equal portions while stirring to give a precipitate. The precipitate was stirred for 30 minutes before it was filtered, washed with water (3×50 cm³), and air dried for 30 minutes. The crude material was crystallised from hot ethanol (100 cm³) to yield the title compound (4.87 g, 56%) as a light grey solid. Mp 137° C.; $\nu_{max}$(KBr)/cm$^{-1}$ 2910 (CH), 2876 (CH), 2856 (CH), 2799 (CH), 1659 (C=O), 1596 (NO$_2$), 1502 (NO$_2$); $\delta_H$ (250 MHz; CDCl$_3$) 2.16 (3H, s, CH$_3$), 2.93 (12H, s, NCH$_3$), 6.59-6.62 (2H, d, J 8.5, ArH), 6.69-6.71 (2H, d, J 2.75, ArH), 7.08-7.47 (2H, brd s, ArH); $\delta_C$ (62.9 MHz; CDCl$_3$) 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$); m/z (ES) 284.2 (100%, [M−OAc]$^+$), 328.1 (15%, [M+M]$^+$), 350.1 (41%, [M+Na]$^+$).

Synthesis 18

1-(3,7-Bis-dimethylamino-phenothiazin-10-yl)-ethanone

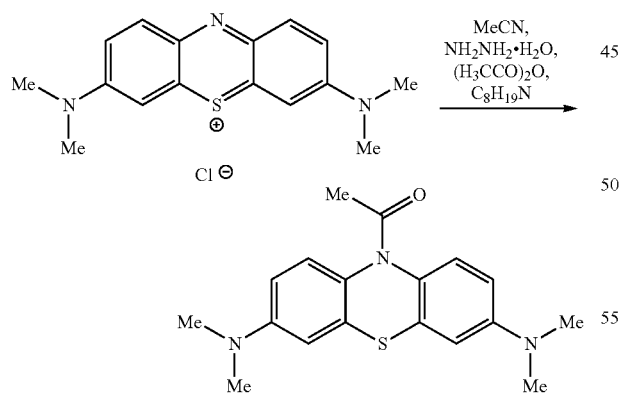

Synthesis using hydrazine monohydrate/Hunig's base in one pot. To a 250 cm³ round bottom flask under an atmosphere of nitrogen was added methylthioninium chloride trihydrate (80.2 mmol, 30 g) and acetonitrile (150 cm³). Hydrazine monohydrate (176.5 mmol, 8.84 g) was added and the mixture was heated to reflux and stirred for 10 minutes before cooling to 25° C. The yellow/green suspension had acetic anhydride (794 mmol, 81.2 g) and Hunig's base (diisopropylethylamine) (232 mmol, 29.97 g) added. The mixture was heated at 90° C. for 2 hours. The cooled mixture was then poured carefully into ice water (400 cm³) in ten equal portions while stirring to give a precipitate. The precipitate was stirred for 30 minutes before it was filtered, washed with water (3×100 cm³), and air dried for 30 minutes. The crude material was crystallised from hot ethanol (400 cm³) to yield the title compound (17.15 g, 65%) as a light grey solid. Mp 137° C.; $\nu_{max}$(KBr)/cm$^{-1}$ 2910 (CH), 2876 (CH), 2856 (CH), 2799 (CH), 1659 (C=O), 1596 (NO$_2$), 1502 (NO$_2$); $\delta_H$ (250 MHz; CDCl$_3$) 2.16 (3H, s, CH$_3$), 2.93 (12H, s, NCH$_3$), 6.59-6.62 (2H, d, J 8.5, ArH), 6.69-6.71 (2H, d, J 2.75, ArH), 7.08-7.47 (2H, brd s, ArH); $\delta_C$ (62.9 MHz; CDCl$_3$) 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$); m/z (ES) 284.2 (100%, [M−OAc]$^+$), 328.1 (15%, [M+H]$^+$), 350.1 (41%, [M+Na]$^+$).

Synthesis 19

3,11-Dinitro-10H-phenothiazine

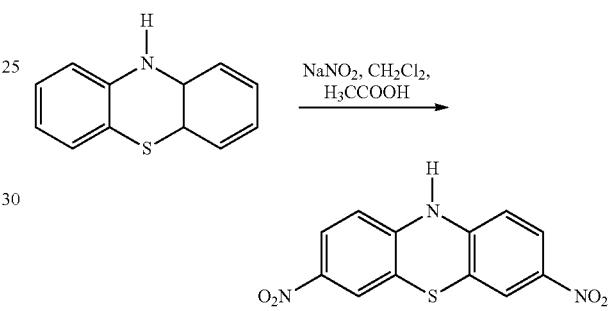

10H-Phenothiazine (20.00 g, 100 mmol), dichloromethane (100 cm³) and acetic acid (40 cm³) had sodium nitrite (20.07 g, 300 mmol) added and the mixture was stirred for 10 minutes at room temperature. Additional acetic acid (40 cm³), dichloromethane (100 cm³) and sodium nitrite (20.07 g, 300 mmol) were then added. A further 120 cm³ of acetic acid was added to try and break up the thick reaction mixture. The mixture was stirred for 3 hours. The suspension was filtered and washed with 100 cm³ each of ethanol, water, and finally ethanol to give a purple/brown solid. The residue was stirred in hot DMF and allowed to cool before filtering the dinitro product, which was washed with ethanol (150 cm³) and dried to give the title compound (24.88 g, 86%) as a brown solid; $\nu_{max}$(KBr)/cm$^{-1}$ 3331 (NH), 3294 (NH), 3229 (NH), 3101 (CH), 3067 (CH), 1602 (NO$_2$), 1558 (NO$_2$); $\delta_H$ (250 MHz; DMSO) 6.73-6.76 (2H, d, J 9, ArH), 7.78 (2H, s, ArH), 7.89-7.85 (2H, d, J 9, ArH).

Synthesis 20

1-(3,7-Bis-diethylamino-phenothiazin-10-yl)-ethanone

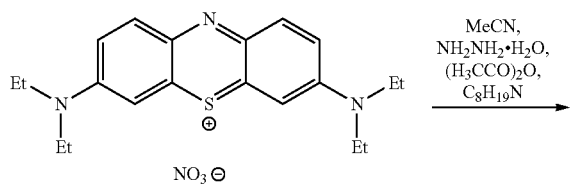

-continued

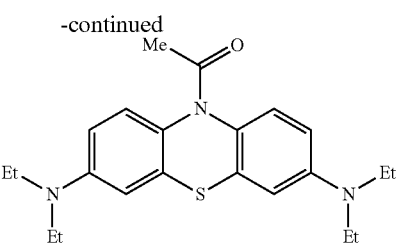

To a 250 cm³ round bottom flask under an atmosphere of nitrogen was added ethylthioninium nitrate monohydrate (7.13 mmol, 3 g) and acetonitrile (20 cm³). Hydrazine monohydrate (16.4 mmol, 0.82 g) was added and the mixture was heated to reflux and stirred for 10 minutes before cooling to 25° C. The brown solution had acetic anhydride (114 mmol, 11.65 g) and Hunig's base (diisopropylethylamine) (21.4 mmol, 2.77 g) was added. The mixture was heated at 90° C. for 2 hours. The cooled mixture was then poured carefully into ice water (40 cm³) in ten equal portions while stirring to give a precipitate. The precipitate was stirred for 30 minutes before it was filtered, washed with water (3×25 cm³) and air dried for 30 minutes. The crude material was crystallised from hot ethanol (50 cm³) to yield the title compound (1.73 g, 63%) as a light grey solid. $\delta_H$ (250 MHz; CDCl₃) 7.0-7.5 (2H, brds, ArH), 6.64 (2H, s, ArH), 6.52 (2H, d, ArH), 3.35 (8H, q, 7, NCH₂), 2.18 (3H, s, CH₃), 1.16 (12H, t, 7, CH₃); $\delta_C$ (62.9 MHz; CDCl₃) 12.5 (CH₃), 22.9 (CH₃), 44.6 (NCH₂), 110.1 (ArC), 127.4 (ArC), 146.5 (ArC), 170.2 (C=O).

Synthesis 21

N,N,N',N'-Tetraethyl-10H-phenothiazine-3,7-diamine bis(hydrogen chloride)

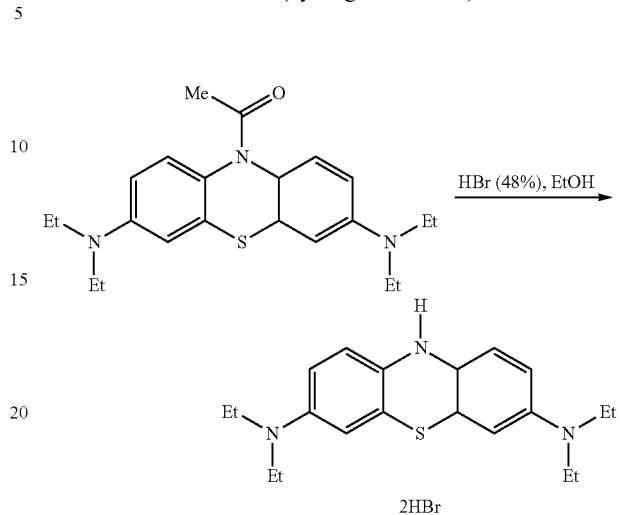

To a round bottom flask was added 1-(3,7-bis-diethylamino-phenothiazin-10-yl)-ethanone (0.5 g, 1.30 mmol), ethanol (5 cm³), and hydrochloric acid (37%, 1.3 cm³) and the solution was heated at 80° C. for 1 hour. Once cooled to room temperature, the mixture was concentrated giving the title compound (0.54 g, 100%) as a light green glass. $\delta_H$ (250 MHz; CD₃OD) 7.07 (4H, brd, ArH), 6.65 (2H, brd, ArH), 3.35 (8H, brd, NCH₂), 0.97 (12H, brd, CH₃); $\delta_C$ (62.9 MHz; CD₃OD) 10.8 (CH₃), 55.1 (NCH₂), 116.6 (ArC), 120.4 (ArC), 121.5 (ArC), 123.6 (ArC), 132.6 (ArC), 144.5 (ArC).

Synthesis 22

N,N,N',N'-Tetraethyl-10H-phenothiazine-3,7-diamine bis(hydrogen bromide)

To a round bottom flask was added 1-(3,7-bis-diethylamino-phenothiazin-10-yl)-ethanone (0.5 g, 1.30 mmol), ethanol (5 cm³), and hydrobromic acid (48%, 0.75 cm³) and the solution was heated at 80° C. for 1 hour. Once cooled to room temperature, the mixture was concentrated giving the title compound (0.65 g, 100%) as a light yellow glass. $\delta_H$ (250 MHz; D₂O) 7.05 (4H, brd, ArH), 6.79 (2H, brd d, ArH), 3.43 (8H, brd, NCH₂), 1.05 (12H, brd t, CH₃); $\delta_C$ (62.9 MHz; D₂O) 12.3 (CH₃), 56.2 (NCH₂), 117.9 (ArC), 121.4 (ArC), 122.4 (ArC), 124.5 (ArC), 133.5 (ArC), 145.1 (ArC).

Synthesis 23

N,N,N',N'-Tetramethyl-10H-phenothiazine-3,7-diamine bis(hydrogen chloride)

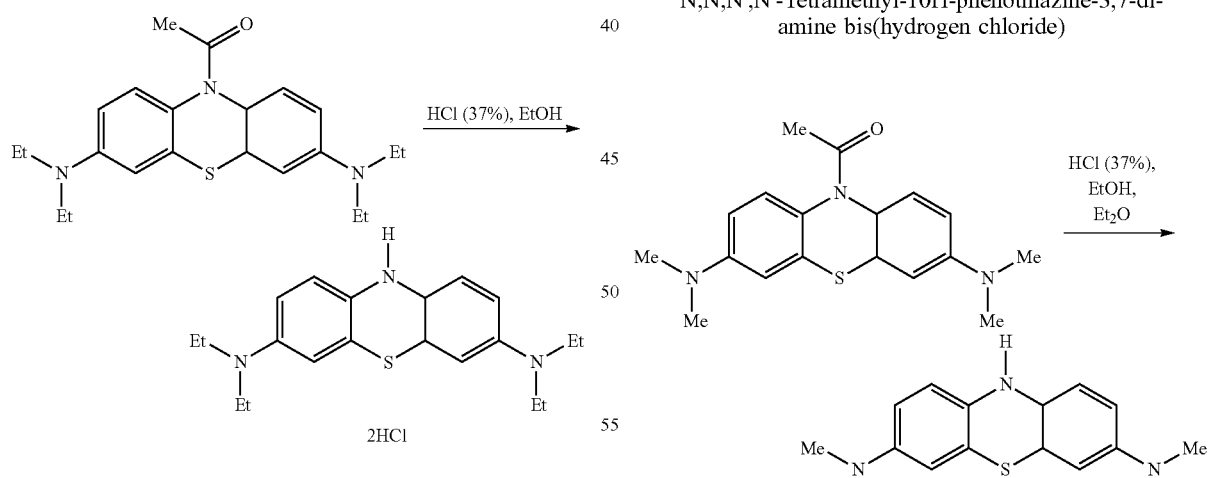

To a round bottom flask was added 1-(3,7-bis-dimethylamino-phenothiazin-10-yl)-ethanone (1 g, 3.05 mmol), ethanol (10 cm³), and hydrochloric acid (37%, 3 cm³) and the solution was heated at 80° C. for 1 hour. Once cooled to room temperature, diethyl ether was added while stirring until a constant turbid solution was obtained. After some time, a precipitate formed, which was filtered and washed with diethyl ether (10 cm³) giving the title compound (0.98 g, 90%) as a light green solid. Mp (dec) 230° C.; ν$_{max}$(KBr)/cm$^{-1}$ 3500-3229 (NH), 3061 (CH), 3021 (CH), 2948 (CH), 2879 (CH), 2679 (CH), 2601 (CH), 1604 (CH), 1483 (CH), 1318 (CH); δ$_H$ (250 MHz; D$_2$O) 3.18 (12H, s, NCH$_3$), 6.67 (2H, d, J 8.5, ArH), 7.16 (4H, brd s, ArH); δ$_C$ (62.9 MHz; D$_2$O) 144.3 (ArC), 138.9 (ArC), 122.4 (ArC), 120.8 (ArC), 120.7 (ArC), 117.6 (ArC), 48.9 (NCH$_3$); m/z (ES) 286.1 (100%, [M–H, 2Cl]$^+$), 285.1 (40%), 284.1 (41%, [M–3H, 2Cl]$^+$).

Synthesis 24

N,N,N',N'-Tetramethyl-10H-phenothiazine-3,7-diamine bis(hydrogen bromide)

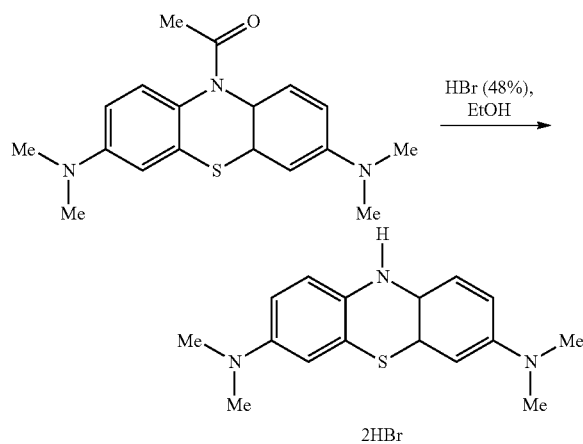

To a round bottom flask was added 1-(3,7-bis-dimethyl-amino-phenothiazin-10-yl)-ethanone (1 g, 3.05 mmol), ethanol (10 cm³), and hydrobromic acid (48%, 4 cm³) and the solution was heated at 80° C. for 1 hour. Once cooled to room temperature, a precipitate formed, which was filtered and washed with diethyl ether (10 cm³) giving the product (1.22 g, 89%) as a light mustard solid. Mp (dec) 230° C.; ν$_{max}$ (KBr)/cm$^{-1}$ 3500-3229 (NH), 3061 (CH), 3021 (CH), 2948 (CH), 2879 (CH), 2679 (CH), 2601 (CH), 1604 (CH), 1483 (CH), 1318 (CH); δ$_H$ (250 MHz; D$_2$O) 3.18 (12H, s, NCH$_3$), 6.66 (2H, d, J 8.75, ArH), 7.15 (4H, s, ArH); δ$_C$ (62.9 MHz; D$_2$O) 144.3 (ArC), 138.9 (ArC), 122.4 (ArC), 120.8 (ArC), 120.7 (ArC), 117.6 (ArC), 48.9 (NCH$_3$).

Synthesis 25

N,N,N',N'-Tetraethyl-10H-phenothiazine-3,7-diamine bis(hydrogen bromide)

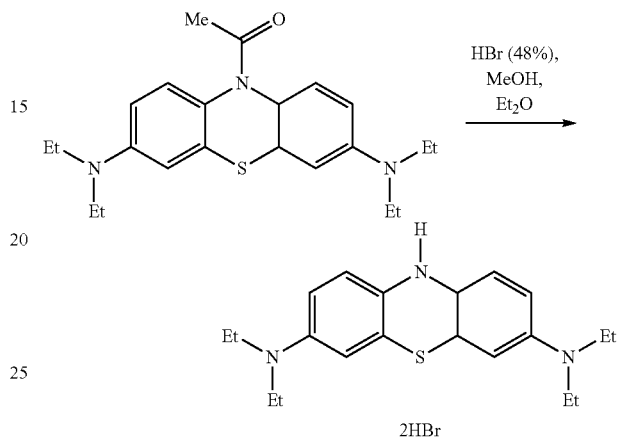

To a round bottom flask was added 1-(3,7-bis-diethyl-amino-phenothiazin-10-yl)-ethanone (1.0 g, 2.60 mmol), methanol (10 cm³), and hydrobromic acid (48%, 2.94 cm³) and the solution was heated at 80° C. for 1 hour. Once cooled to 5° C., the mixture had diethyl ether added, giving a cloudy solution. The solution was stirred for 30 minutes and gave the title compound (0.83 g, 63%) as a light yellow solid. δ$_H$ (250 MHz; D$_2$O) 7.05 (4H, brd, ArH), 6.79 (2H, brd d, ArH), 3.43 (8H, brd, NCH$_2$), 1.05 (12H, brd t, CH$_3$); δ$_C$ (62.9 MHz; D$_2$O) 12.3 (CH$_3$), 56.2 (NCH$_2$), 117.9 (ArC), 121.4 (ArC), 122.4 (ArC), 124.5 (ArC), 133.5 (ArC), 145.1 (ArC).

Example 10—Other Cognitive or CNS Disorders

Methods of treatment, prophylaxis, diagnosis or prognosis of the present invention, utilising DAPTZ compounds in oxidised or reduced form, may in any aspect be applied to any one or more of the following diseases.

| Protein | Disease | Aggregating domain and/or mutations | Fibril subunit size (kDa) | Reference |
|---|---|---|---|---|
| Diseases of protein aggregation | | | | |
| Neuro-degenerative disorders | | | | |
| Prion protein | Prion diseases (CJD, nvCJD, Fatal familial insomnia, Gerstmann-Straussler-Scheinker syndrome, Kuru) | Inherited and sporadic forms PrP-27-30; many mutations. | 27 | Prusiner (1998) |
| | | Fibrillogenic domains: 113-120, 178-191, 202-218. | | Gasset et al. (1992) |

| Protein | Disease | Aggregating domain and/or mutations | Fibril subunit size (kDa) | Reference |
|---|---|---|---|---|
| Tau protein | Alzheimer's disease, Down's syndrome, FTDP-17, CBD, post-encephalitic parkinsonism, Pick's disease, parkinsonism with dementia complex of Guam | Inherited and sporadic forms | 10-12 | Wischik et al. (1988) |
| | | Truncated tau (tubulin-binding domain) 297-391. Mutations in tau in FTDP-17. Many mutations in presenilin proteins. | | Hutton et al. (1998) Czech et al. (2000) |
| Amyloid β-protein | Alzheimer's disease, Down's syndrome | Inherited and sporadic forms Amyloid β-protein; 1-42(3). 11 mutations in APP in rare families. | 4 | Glenner & Wong, (1984) Goate et al. (1991) |
| Huntingtin | Huntington's disease | N-termini of protein with expanded glutamine repeats. | 40 | DiFiglia et al. (1997) |
| Ataxins (1, 2, 3, 7) | Spinocerebellar ataxias (SCA1, 2, 3, 7) | Proteins with expanded glutamine repeats. | | Paulson et al. (1999) |
| Atrophin | Dentarubropallidoluysian atrophy (DRPLA) | Proteins with expanded glutamine repeats. | | Paulson et al. (1999) |
| Androgen receptor | Spinal and bulbar muscular atrophy | Proteins with expanded glutamine repeats. | | Paulson et al. (1999) |
| Neuroserpin | Familial encephalopathy with neuronal inclusion bodies (FENIB) | Neuroserpin; S49P, S52R. | 57 | Davis et al. (1999) |
| α-Synuclein | Parkinson's disease, dementia with Lewy bodies, multiple system atrophy | Inherited and sporadic forms | 19 | Spillantini et al. (1998) |
| | | A53T, A30P in rare autosomal-dominant PD families. | | Polymeropoulos et al. (1997) |
| Cystatin C | Hereditary cerebral angiopathy (Icelandic) | Cystatin C less 10 residues; L68Q. | 12-13 | Abrahamson et al. (1992) |
| Superoxide dismutase 1 | Amyotrophic lateral sclerosis | SOD1 mutations. | | Shibata et al. (1996) |

REFERENCES FOR EXAMPLE 10

Abrahamson, M., Jonsdottir, S., Olafsson, I. & Grubb, A. (1992) Hereditary cystatin C amyloid angiopathy identification of the disease-causing mutation and specific diagnosis by polymerase chain reaction based analysis. *Human Genetics* 89, 377-380.

Czech, C., Tremp, G. & Pradier, L. (2000) Presenilins and Alzheimer's disease: biological functions and pathogenic mechanisms. *Progress in Neurobiology* 60, 363-384.

Davis, R. L., Shrimpton, A. E., Holohan, P. D., Bradshaw, C., Feiglin, D., Collins, G. H., Sonderegger, P., Kinter, J., Becker, L. M., Lacbawan, F., Krasnewich, D., Muenke, M., Lawrence, D. A., Yerby, M. S., Shaw, C.-M., Gooptu, B., Elliott, P. R., Finch, J. T., Carrell, R. W. & Lomas, D. A. (1999) Familial dementia caused by polymerization of mutant neuroserpin. *Nature* 401, 376-379.

DiFiglia, M., Sapp, E., Chase, K. O., Davies, S. W., Bates, G. P., Vonsattel, J. P. & Aronin, N. (1997) Aggregation of huntingtin in neuronal intranuclear inclusions and dystrophic neurites in brain. *Science* 277, 1990-1993.

Gasset, M., Bladwin, M. A., Lloyd, D. H., abriel, J.-M., Holtzman, D. M., Cohen, F. E., Fletterick, R. & Prusiner, S. B. (1992) Predicted a-helical region of the prion protein when synthesized as peptides form amyloid. *Proceedings of the National Academy of Sciences, USA* 89, 10940-10944.

Glenner, G. G. & Wong, C. W. (1984) Alzheimer's disease: initial report of the purification and characterisation of a novel cerebrovascular amyloid protein. *Biochemical and Biophysical Research Communications* 120, 885-890.

Goate, A., Chartier-Harlin, M.-C., Mullan, M., Brown, J., Crawford, F., Fidani, L., Giuffra, L., Haynes, A., Irving, N., James, L., Mant, R., Newton, P., Rooke, K., Rogues, P., Talbot, C., Pericak-Vance, M., Roses, A., Williamson, R., Rossor, M., Owen, M. & Hardy, J. (1991) Segregation of a missense mutation in the amyloid precursor protein gene with familial Alzheimer's disease. *Nature* 349, 704-706.

Hutton, M., Lendon, C., Rizzu, P., Baker, M., Froelich, S., Houlden, H., Pickering-Brown, S., Chakraverty, S., Isaacs, A., Grover, A., Hackett, J., Adamson, J., Lincoln, S., Dickson, D., Davies, P., Petersen, R. C., Stevens, M., de Graaf, E., Wauters, E., van Baren, J., Hillebrand, M., Joosse, M., Kwon, J. M., Nowotny, P., Che, L. K., Norton, J., Morris, J. C., Reed, L. A., Trojanowski, J. Q., Basun, H., Lannfelt, L., Neystat, M., Fahn, S., Dark, F., Tannenberg, T., Dodd, P. R., Hayward, N., Kwok, J. B. J., Schofield, P. R., Andreadis, A., Snowden, J., Craufurd, D., Neary, D., Owen, F., Oostra, B. A., Hardy, J., Goate, A., van Swieten, J., Mann, D., Lynch, T. & Heutink, P. (1998) Association of missense and 5'-splice-site mutations in tau with the inherited dementia FTDP-17. *Nature* 393, 702-705.

Paulson, H. L. (1999) Human genetics '99: trinucleotide repeats. *American Journal of Human Genetics* 64, 339-345.

Polymeropoulos, M. H., Lavedan, C., Leroy, E., Ide, S. E., Dehejia, A., Dutra, A., Pike, B., Root, H., Rubenstein, J., Boyer, R., Stenroos, E. S., Chandrasekharappa, S., Athanassiadou, A., Papaetropoulos, T., Johnson, W. G., Lazzarini, A. M., Duvoisin, R. C., Di Iorio, G., Golbe, L. I. & Nussbaum, R. L. (1997) Mutation in the a-synuclein gene identified in families with Parkinson's disease. *Science* 276, 2045-2047.

Prusiner, S. B., Scott, M. R., DeArmond, S. J. & Cohen, F. E. (1998) Prion protein biology. *Cell* 93, 337-348.

Shibata, N., Hirano, A., Kobayashi, M., Siddique, T., Deng, H. X., Hung, W. Y., Kato, T. & Asayama, K. (1996) Intense superoxide dismutase-1 immunoreactivity in intracytoplasmic hyaline inclusions of familial amyotrophic lateral sclerosis with posterior column involvement. *Journal of Neuropathology and Experimental Neurology* 55, 481-490.

Spillantini, M. G., Crowther, R. A., Jakes, R., Hasegawa, M. & Goedert, M. (1998) a-Synuclein in filamentous inclusions of Lewy bodies from Parkinson's disease and dementia with Lewy bodies. *Proceedings of the National Academy of Sciences, USA* 95, 6469-6473.

Wischik, C. M., Novak, M., Thøgersen, H. C., Edwards, P. C., Runswick, M. J., Jakes, R., Walker, J. E., Milstein, C., M., R. & Klug, A. (1988) Isolation of a fragment of tau derived from the core of the paired helical filament of Alzheimer's disease. *Proceedings of the National Academy of Sciences, USA* 85, 4506-4510.

Example 11—Standard Dissolution Test

Title:
Simulated Intestinal Fluid Dissolution for DAPTZ containing capsules.

Performed by:
Encap Drug Delivery, Units 4, 5 & 6, Oakbank Park Way, Livingston, West Lothian, EH53 0TH, Scotland, UK.

1. Purpose

This method is suitable for use as a Dissolution Test Method for the purpose of providing data for the determination of % dissolution over time of DAPTZ containing dosage units in simulated Intestinal Fluid (SIF), as described in the USP (www[dot]usp[dot]org) as dissolution media.

The method is exemplified with 30 mg, 60 mg and 100 mg MTC capsules formulated in Gelucire 44/14 and employs the standard USP<711>Dissolution, Apparatus2 (paddle and sinker). Where relevant below, the MTC can be replaced by an alternative DAPTZ compound at the appropriate loading and.

2. Method Conditions 2.1. Reagents

Water—Lab. grade or equivalent
Potassium Dihydrogen Orthophosphate—Lab. grade or equivalent
Sodium Hydroxide—Lab. grade or equivalent
Pancreatin—USP Grade
Hydrochloric Acid—Lab. grade or equivalent 2.2. Safety Reagents are poss. irritant and poss. harmful.

2.3. Dissolution Conditions

Dissolution Apparatus
Apparatus—USP<711>Dissolution, Appartus2 (paddle and sinker)
Sample—1 capsule placed in a sinker
Rotation rate—75 rpm
Temperature—37° C.±0.5° C.
Dissolution Medium—1000 ml Simulated Intestinal Fluid
Sampling Times—15, 30, 45, 60 minutes
Test duration—60 minutes
Sample size—5 ml (not replaced) (Do not filter)
UV Spectrophotometer Conditions
Determination wavelength—665 nm
Reference—Dilute SIF
Path Length—10 mm
Band Width—2.0 nm 2.4. Preparation of Simulated Intestinal Fluid (SIF)

For each liter required, dissolve 6.8 g of potassium dihydrogen orthophosphate in 250 ml of water, mix and add 77 ml of 0.2N Sodium Hydroxide and 500 ml of water. Add 10.0 g of pancreatin mix, USP, and adjust the resulting solution with either 0.2N Sodium Hydroxide or 0.2N Hydrochloric acid to a pH of 6.8±0.1. Dilute with water to 1000 ml. This solution must be prepared fresh every day.

2.5. Standard Solutions (Prepare in Duplicate)

Accurately weigh approximately 100 mg of MTC into a 100 ml volumetric flask. Dissolve in 80 ml of 50/50 ethanol water with 15 mins sonication and then make to volume with 50/50 ethanol/water and mix well (1000 µg/ml). Transfer 5.0 ml of this solution to a 100 ml volumetric flask and make this flask to volume with SIF and mix well (50 µg/ml). Transfer 4.0 ml of this solution to a 100 ml volumetric flask and make this flask to volume with water and mix well. (2.0 µg/ml). This is the standard solution.

2.6. Dissolution Procedure

Add 1000 ml of Simulated Intestinal Fluid to each of the six dissolution vessels. Insert the paddles at the correct rotation speed and allow to equilibrate to 37° C.±0.5° C. Place six individual capsules into stainless steel sinkers and add one to each vessel noting the time. At each of the specified times withdraw a 5 ml sample.

2.7 Preparation of Background Reference

Transfer 4.0 ml of SIF to a 100 ml volumetric flask and make to volume with water and mix well. This solution is to be used as the background reference in the UV Spectrophotometer.

2.8 Sample Preparation

For the 30 mg capsules transfer 3.0 ml of this solution to a 50 ml volumetric flask and make to volume with water and mix well (1.8 µg/ml).

For the 60 mg capsules transfer 3.0 ml of this solution to a 100 ml volumetric flask and make to volume with water and mix well (1.8 µg/ml).

For the 100 mg capsules transfer 1 ml of this solution to a 50 ml volumetric flask and make to volume with water and mix well (2.0 µg/ml). These are the sample solutions.

2.9. Procedure

Determine the standard and sample solutions on a UV Spectrophotometer that has been turned on and allowed to warm to operating temperature.

2.10 Standard Verification

Verify the mean response factors of two standard solutions. Standard 2 must verify as 98-102% of standard 1.

2.11 Calculations

Conduct all calculations to 2 decimal places

Determine the MTC % release of each sample relative to the reference standard using the appropriate equation:

% release for 100 mg capsule=$Asam/Astd \times Wstd/(100 \text{ mg}) \times P \times 100$ % release for 60 mg capsule=$Asam/Astd \times Wstd/(60 \text{ mg}) \times 2/3 \times P \times 100$ % release for 30 mg capsule=$Asam/Astd \times Wstd/(30 \text{ mg}) \times 1/3 \times P \times 100$ Asam is the MTC Absorbance for the individual sample at 665 nm Astd is the mean MTC Absorbance of the two standards at 665 nm Wstd is the mean weight of MTC standards used (mg)

P is the Purity of reference standard used, as a decimal (eg 0.999)

(Where the input material is used as a standard a correction factor of 1 is applied for P)

Plot the MTC % Release against the dissolution time on one graph where individual vessels are plotted separately.

Plot the mean MTC % Release, across all six vessels, against the dissolution time on one graph.

Thus generally the following equation can be used.

% release for $x$ mg capsule=$Asam/Astd \times Wstd/(x) \times d \times P \times 100$ It will be appreciated by those skilled in the art that 'd' is the correction, if required, for dilution in sample preparation as in step 2.8 above.

2.12 Standard Test for Simulated Gastric Fluid (SGF)

This standard test is carried out as described above but using SGF in place of SIF. SGF is prepared according to USP29 as follows:

Gastric Fluid, Simulated, TS-Dissolve 2.0 g of sodium chloride and 3.2 g of purified pepsin, that is derived from porcine stomach mucosa, with an activity of 800 to 2500 units per mg of protein, in 7.0 mL of hydrochloric acid and sufficient water to make 1000 mL. [Pepsin activity is described in the Food Chemicals Codex specifications under *General Tests and Assays*]. This test solution has pH of about 1.2.

Example 12—Quantitative Models for the Progression and Treatment of Alzheimer's Disease The chemical process underlying Alzheimer's Disease is the aggregation and truncation of tau proteins. In this Example, we use kinetic models of the tau reaction pathway in order to describe the progression of the disease and the effect of treatment, and to compare the effectiveness of treatments which target different parts of the pathway.

1. Formulating an Equilibrium Model

FIG. 37A shows the binding of a tau protein to an aggregate of truncated tau proteins, followed by the truncation of the tau protein to form a larger aggregate. Within the cell this reaction is embedded in a larger pathway, with paths for the creation of new tau proteins and for the clearance of aggregates.

FIG. 37B shows a natural model. Here, S denotes the amount of soluble tau protein, and A the amount of aggregated truncated tau. In order to produce a kinetic model, we need to specify rates. It is known that the rate of aggregation of tau increases with both the availability of S and the availability of A [Wischik, C. M., Edwards, P. C., Lai, R. Y. K., Roth, M. & Harrington, C. R. (1996) Selective inhibition of Alzheimer disease-like tau aggregation by phenothiazines. Proceedings of the National Academy of Sciences, USA 93, 11213-11218]. It is natural to assume that there is a feedback mechanism involved in the creation of S, and thus that the rate of production of S depends on the amount of S [Lai, R. Y. K., Gertz, H.-J., Wischik, D. J., Xuereb, J. H., Mukaetova-Ladinska, E. B., Harrington, C. R., Edwards, P. C., Mena, R., Paykel, E. S., Brayne, C., Huppert, F. A., Roth, M. & Wischik, C. M. (1995) Examination of phosphorylated tau protein as a PHF-precursor at early stage Alzheimer's disease. Neurobiology of Aging 16, 433-445.]. For the other pathways shown, we will make the standard kinetic assumption that the rate of a reaction is proportional to the amount of reagent.

This gives us the kinetic model shown in FIG. 37C. By this picture we mean, for example, that if S(t) is the amount of soluble tau protein at time t then $$d/dt\, S(t) = \lambda(S(t)) - k_{S0} S(t) - kA(t) S(t) \qquad \text{[equation 1]}$$

Timescales of Disease Progression and of Kinetics

A crucial aspect of this model is the timescale over which Alzheimer's Disease progresses, and its relationship with the timescale over which equations like equation 1 operate. It is our position that the dynamics of the kinetic equations occur over hours or days, and that the progression of the disease is a due to the slow change of parameters like $k_{A0}$ over the timescale of years. A contrary position was adopted in Wischik et al. (1995), namely that the timescale of the kinetics is measured in years, and that the progression of the disease reflects the gradual increase of A(t) as modelled by the kinetics.

There are two main pieces of evidence for the separation of timescales. First, in vitro experiments [WO96/30766], in which soluble tau is incubated with solid-phase truncated tau, show that most of the soluble tau has bound within a matter of hours. The second piece of evidence comes from in vivo experiments on transgenic mice which express human truncated tau protein [WO 02/059150]. These mice slowly develop Alzheimer's disease tau pathology over periods of months, as measured both by cognitive tests and by neuropathological examination [Zabke, C., Dietze, S., Stamer, K., Rickard, J. E., Harrington, C. R., Theuring, F., Seng, K. M. & Wischik, C. W. (2008) Early and advanced stages of tau aggregation In transgenic mouse models.

International Conference on Alzheimer's Disease, Chicago, 26-31 Jul. 2008, P1-054]. When treated with daily oral doses of MTC over a period of 17 days, the Alzheimer's disease pathology was reduced [Harrington, C., Rickard, J. E., Horsley, D., Harrington, K. A., Hindley, K. P., Riedel, G., Theuring, F., Seng, K. M. & Wischik, C. M. (2008) Methylthioninium chloride (MTC) acts as a tau aggregation inhibitor (TAI) in a cellular model and reverses tau pathology in transgenic mice models of Alzheimer's disease. International Conference on Alzheimer's Disease, Chicago, 26-31 Jul. 2008, O1-06-04]. Therefore the timescale of the kinetics is of the order of days, while the timescale of the progression of the disease is much longer, measured in months for these mice.

Our mathematical technique must therefore be this: we suppose that any patient has rate constants which depend on how long he has had the disease, say $k_{A0}(a)$ etc. where a is the number of years since onset; and we suppose that the resulting levels of S and A are the equilibrium values of the dynamical system. To be concrete, we need to solve equations like this modified form of equation 1:

$$\lambda(S) - k_{S0}S - kAS = 0. \qquad \text{[equation 2]}$$

We have omitted t, since we are not interested in the dynamics of the system but only in the equilibrium behaviour. We will sometimes write S(a) etc. to emphasize the dependence on the values of the rate constants.

Accounting for the Creation of New Aggregates

The aggregation reaction (FIG. 37A) starts with one aggregate molecule and finishes with one aggregate molecule, so it describes the growth of existing aggregates and not the creation of new aggregates. Likewise in the kinetic system (FIG. 37C), if we do not model the creation of aggregates then the pool of A will steadily decrease, meaning that the equilibrium solution is A=0.

The simplest way to account for the creation of new aggregates is by altering the stoichiometry of the aggregation reaction. Specifically, we will assume the scheme shown in FIG. 37D (though the actual values of $n_1$ and $n_2$ are unknown).

For example, if $n_1=2.3$ and $n_2=1.87$ then from 230 tau molecules and 100 aggregate molecules there are 87 new aggregate molecules produced.

Summary of Model

We have proposed the dynamical system model shown in FIG. 37E.

The equations for the equilibrium state of this system are:

$$\lambda(S) = k_{S0}S + n_1 kAS \qquad \text{[equation 3]}$$

$$n_2 kAS = kAS + k_{A0}(a)A \qquad \text{[equation 4]}$$

In the remainder of this Example we describe several experiments which let us quantify the rate constants and thus to predict the effect of treatment.

2. Quantifying the Progression of Disease

Lai et al. (1995) studied a number of Alzheimer's patients post-mortem and found a relationship between A and S:

$$S = f(A) = \alpha/A^\beta - 1 \qquad \text{[equation 5]}$$

where $\alpha = 2450$ and $\beta = 0.3459$.

Mukaetova-Ladinska et al. (Mukaetova-Ladinska, E. B., Garcia-Siera, F., Hurt, J., Gertz, H. J., Xuereb, J. H., Hills, R., Brayne, C., Huppert, F. A., Paykel, E. S., McGee, M., Jakes, R., Honer, W. G., Harrington, C. R. & Wischik, C. M. (2000) Staging of cytoskeletal and β-amyloid changes in human isocortex reveals biphasic synaptic protein response during progression of Alzheimer's disease. American Journal of Pathology 157, 623-636) studied a number of Alzheimer's patients pre- and post-mortem, and found a relationship between PHF levels and the patient's Braak stage B:

$$PHF = g(B) = \text{Exp}(\gamma B/(\delta - B)) - 1 \qquad \text{[equation 1]}$$

where $\gamma = 4.8383$ and $\delta = 9.8156$.

It is reasonable to assume that PHF levels are proportional to levels of tau aggregates:

$$A = \varepsilon PHF \qquad \text{[equation 2]}$$

though ε is unknown.

Ohm et al. [Ohm, T. G., Müller, H., Braak, H. & Bohl, J. (1995) Close-meshed prevalence rates of different stages as a tool to uncover the rate of Alzheimer's disease-related neurofibrillary changes. Neuroscience 64, 209-217] studied the distribution of Braak stage within a population, and in the appendix we describe how from his data we can obtain a relationship between mean Braak stage B and the time a since the onset of dementia, in years:

$$B = h(a) = *** \qquad \text{[equation 8]}$$

Using these three relationships, we can rewrite the equilibrium equations 3-4 to obtain:

$$\lambda(S) = k_{S0}S + n_1 kf^{-1}(S)S \qquad \text{[equation 9]}$$

$$k_{A0}(a) = (n_2 - 1)kf(\varepsilon g(h(a))) \qquad \text{[equation 10]}$$

3. Quantifying the Effect of a Drug

WO 02/055720 describes a cell model for Alzheimer's disease, and measurements demonstrating the effect of MTC on levels of A. The cells have been genetically modified to produce soluble tau S at a constant rate. On its own, this does not spontaneously form aggregates, and so the cells have been further modified to produce truncated tau T at a constant rate. We assume that the cells have a normal mechanism for destroying T, and that the effect of the drug is to open up a pathway by which A is dissolved and turns into T. For simplicity, we assume that here S is only used in the Alzheimer's pathway. We therefore have the kinetic model shown in FIG. 37F.

We have written $k_{AT}(d)$ to emphasize that this rate constant depends on the dose level d, and we will assume that $k_{AT}(0) = 0$. We should strictly write $k_{A0}(a_{cell})$, where $a_{cell}$ is the time in years since the onset of the disease for these cells, though we will suppress this in our equations.

The equilibrium equations for this system are:

$$\lambda = kASn_1 \qquad \text{[equation 11]}$$

$$\mu + k_{AT}(d)A = T(k_{T0} + k_{TA}) \qquad \text{[equation 12]}$$

$$k_{TA}T + n_2 kAS = kAS + A(k_{AT}(d) + k_{A0}) \qquad \text{[equation 13]}$$

Using equations 11 and 12, we can eliminate S and T from equation 12 to obtain:

$$A = [(n_2-1)/n_1 \lambda + k_{TA}/(k_{T0}+k_{TA})\mu]/[k_{A0}+k_{AT}(d)k_{T0}/(k_{T0}+k_{TA})]$$

Writing A(0) for the baseline level of aggregate tau, in the absence of any drug, then:

$$A(0) = [(n_2-1)/n_1 \lambda + k_{TA}/(k_{T0}+k_{TA})\mu]/k_{A0}$$

These two equations cancel conveniently, and tell us that:

$$k_{AT}(d)/k_{A0} = (1 + k_{TA}/k_{T0})(A(0)/A(d) - 1)$$

(We have written A(d) here to emphasize that the observed level of aggregates A is a function of the dose d).

WO 02/055720 reports that:

$$A(d)/A(0)=g(d)=\zeta d^\theta/(\eta^\theta+d^\theta)+1 \quad \text{[equation 14]}$$

where $\zeta=-1.0665$, $\eta=51.735$ and $\theta=1.3328$.

4. Quantifying the Combined Effect

We can now ask: how to we expect the drug would alter the progression of the disease? Our kinetic model is now that shown in FIG. 37G, with equilibrium equations:

$$\lambda(S)=k_{S0}S+n_1kAS \quad \text{[equation 15]}$$

$$k_{AT}(d)A=T(k_{T0}+k_{TA}) \quad \text{[equation 16]}$$

$$k_{TA}T+n_2kAS=kAS+A(k_{AT}(d)+k_{A0}(a)) \quad \text{[equation 17]}$$

We wish to solve these equations for $A=A(a,d)$. To do this, it is most convenient to use equation 16 to express T in terms of A:

$$T=Ak_{AT}(d)/(k_{T0}+k_{TA})$$

and then to substitute into 17 to find an expression for $S=S(a,d)$ $$(n_2-1)kS(a,d)=k_{A0}(a)+k_{AT}(d)k_{T0}/(k_{T0}+k_{TA})$$

and finally to use equations 15 and 9 to turn this into an expression for $A(a,d)$ $$A(a,d)=f^{-1}(S(a,d)) \quad \text{[equation 18]}$$

The expression for $S(a,d)$ can more usefully be written as a ratio involving $S(a_0,0)$ where $a_0$ is the time since the onset of the disease at which treatment was begun. We shall also substitute in the expressions we have obtained for $k_{A0}(a)$ and $k_{AT}(d)$, to give:

$$S(a,d)/S(a_0,0)=k_{A0}(a)/k_{A0}(a_0)+k_{A0}(a_{cell})/k_{A0}(a_0)(1/g(d)-1) \quad \text{[equation 19]}$$

The formula for $g(d)$ is given above in equation 14, the formula for f is given in equation 8, and the formula for $k_{A0}(a)$ is given in equation 9.

Interpretation of the result.

If we let $d=0$, equation 19 gives:

$$S(a,0)/S(a_0,0)=k_{A0}(a)/k_{A0}(a_0)$$

As a increases, the pathway by which aggregates are cleared degenerates, and $k_{A0}(a)$ decreases towards 0; thus $S(a,0)$ decreases towards 0 and, according to equation 18, A increases to infinity. By treating with the drug at some fixed dose, we prevent S from decreasing below a certain threshold:

$$S_{thresh}=k_{A0}(a_{cell})/k_{A0}(a_0)(1/g(d)-1)$$

which means that we prevent A from increasing above a certain threshold $f^{-1}(S_{thresh})$. In words, this treatment does not merely retard the progression of the disease, it stops it.

5. An Alternative Treatment Model

It has been suggested that one might treat Alzheimer's disease inter alia by inhibiting the tau-tau binding reaction (Wischik, C. M., Edwards, P. C., Lai, R. Y. K., Roth, M. & Harrington, C. R. (1996) Selective inhibition of Alzheimer disease-like tau aggregation by phenothiazines. Proceedings of the National Academy of Sciences, USA 93, 11213-11218). What effect would this have on the progression of the disease? Consider the kinetic model shown in FIG. 37H where $k(d)$ is the value of the rate constant, after the reaction has been inhibited by this putative drug at dose d. The equilibrium equations are:

$$\lambda(S)=k_{S0}S+n_1k(d)AS$$

$$n_2k(d)AS=k(d)AS+Ak_{A0}(a)$$

Solving these, and substituting in equation 8, we obtain:

$$S(a,d)/S(a_0,0)=[k_{A0}(a)/k_{A0}(a_0)]/[k(d)/k(0)]$$

$$A(a,d)=f^{-1}(S(a,d))/[k(d)/k(0)]$$

It can be seen that the level of $S(a,d)$ decreases to 0 as time a increases, for any fixed dose d. Therefore the level of A increases to infinity. In words, a treatment based purely on inhibition of the tau-tau binding reaction would retard the progression of the disease, but it could not halt it.

6. Numerical Results

FIG. 37I illustrates these results numerically. The left plot shows the effect of a drug which creates a new pathway A→T, as described in Section 3; the left plot shows the effect of a drug which inhibits the pathway S+A→A, as described in Section Error! Reference source not found. Rather than plotting the level of tau aggregates A, we have plotted MMSE, using the relationship between MMSE and Braak stage B derived from data in Ohm et al. (1995).

$$MMSE=\sigma(\tau-B)/(\rho-B)$$

where $\sigma=56.2204$, $\tau=6.5969$ and $\rho=11.599$, together with the relationships in equations 6 and 7, and setting $\varepsilon=1$. We plot this as a function of number of years since the beginning of treatment, for a patient who started treatment at MMSE=15. The dotted line shows the deterioration of MMSE with no treatment; the other lines show the effect of treatment at various dose levels. The dose levels we are illustrating here are (for the left plot) $d=25$, 50 and 90; and (for the right plot) $k(d)/k(0)=45\%$, 20%, 7%.

7. Implications for Clearance of Tau Aggregates for Disease Progression

These figures (FIG. 37I) illustrate what we have already explained algebraically, namely that inhibiting tau-tau aggregation can only retard the progression of the disease, whereas it can be halted by opening a new pathway for dissolution of aggregates. This can be depicted schematically in FIG. 39. Tau aggregation can be prevented by affecting two sites: firstly by inhibiting the input of tau into the cycle of aggregation and secondly by enhancing the clearance of aggregates from the aggregation cycle (FIG. 39). The level of aggregated tau or paired helical filaments progresses steadily with advancing age. If the input of tau is prevented, then the level of PHFs will decrease to a certain level, predicted by Braak staging, after which time the rate of progression will continue as before. Only when the clearance of aggregated tau is enhanced will their levels of tau begin to decrease over time (FIG. 39). In such circumstances, a drug having such an effect can be said to be disease-modifying. It has been discussed by Wischik et al. (Wischik, C. M., Lai, R. Y. K. & Harrington, C. R. (1997) Modelling prion-like processing of tau protein in Alzheimer's disease for pharmaceutical development. In Microtubule-Associated Proteins: Modifications in Disease. (Eds. J. Avila, R. Brandt, & K. S. Kosik) Harwood Academic Publishers, Amsterdam, 185-241) that tau aggregation can be seeded by proteins arising from age-related mitochondrial turnover (e.g. core protein 2 of complex III, porin and ATP synthetase subunit 9). These aggregates of tau can either assemble into PHFs and/or enter the endosomal-lysosomal clearance pathway, adding to the congestion of this pathway with advancing age (FIG. 40). Enhanced clearance of tau aggregates from this pathway that will decrease the metabolic burden within the neuron. This Example demonstrates how this could halt the progression of the disease, rather than just retard its progression.

The invention claimed is:

1. A method of treating a cognitive or CNS disorder in a patient, comprising orally administering to said patient a delayed-release formulation of a dosage unit containing
a 3,7-diaminophenothiazine (DAPTZ) compound in stable crystalline reduced form as active ingredient, selected from compounds of the following formula and pharmaceutically acceptable salts, solvates, and hydrates thereof:

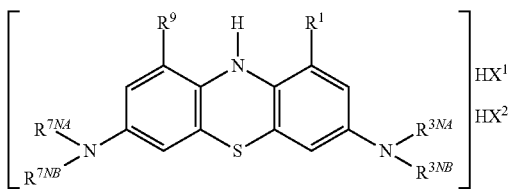

wherein:
each of $R^1$ and $R^9$ is independently selected from: —H;
each of $R^{3NA}$ and $R^{3NB}$ is independently selected from: —H, $C_{2-4}$alkenyl, and halogenated $C_{1-4}$alkyl;
each of $R^{7NA}$ and $R^{7NB}$ is independently selected from: —H, $C_{2-4}$alkenyl, and halogenated $C_{1-4}$alkyl;
each of $HX^1$ and $HX^2$ is independently a protic acid, wherein $X^1$ is an element or compound forming the conjugate base of the protic acid $HX^1$, and $X^2$ is an element or compound forming the conjugate base of the protic acid $HX^2$; and
wherein if any of $HX^1$ and $HX^2$ are hydrohalic acids, then each are independently selected from HCl or HBr,
wherein the delayed-release formulation releases less than 50% of the compound in 6 hours.

2. The method of claim 1 wherein the delayed-release formulation of the reduced DAPTZ compound contains between 100-1000 mg of the DAPTZ compound.

3. The method of claim 2 wherein the delayed-release formulation is given once per day to the patient.

4. The method of claim 1 wherein the delayed-release formulation releases less than 50% 8 hours.

5. The method of claim 1 wherein the dosage unit is gastroretained.

6. The method of claim 5 wherein the gastroretained dosage unit is held in the stomach for at least 30 minutes, and optionally at least 1, 2, 3, 4, 5, 6, 8, 12 hours or more.

7. The method of claim 5 wherein the gastroretained dosage unit comprises at least 50, 60, 70, 80, 90 or 100 mg DAPTZ compound.

8. The method of claim 5 wherein the gastroretained dosage unit comprises either (i) particles that have bioadhesive properties and a propensity to float on the stomach contents or (ii) a swelling system, in either case such as to achieve a size after ingestion of greater than 15 mm.

9. The method of claim 1 wherein the dosage unit is provided as a pharmaceutical composition comprising the DAPTZ compound and a pharmaceutically acceptable carrier, diluent, or excipient.

10. The method of claim 1 wherein the pharmaceutical composition is for a combination therapy and comprises in addition to the DAPTZ compound a further active ingredient selected from: a cholinesterase inhibitor; an NMDA receptor antagonist; a muscarinic receptor agonist; an inhibitor of conversion of amyloid precursor protein to beta-amyloid.

11. The method of claim 1, wherein each of $R^1$ and $R^9$ is independently —H.

12. The method of claim 1, wherein each of $R^{3NA}$ and $R^{3NB}$ and $R^{7NA}$ and $R^{7NB}$ is independently -Me, -Et, -nPr, -nBu, —CH$_2$—CH=CH$_2$, or —CF$_3$.

13. The method of claim 1, wherein the groups —N($R^{3NA}$)($R^{3NB}$) and —N($R^{7NA}$)($R^{7NB}$) are the same, and are selected from: —NMe$_2$ and -NEt$_2$.

14. The method of claim 1, wherein each of the groups —N($R^{3NA}$)($R^{3NB}$) and —N($R^{7NA}$)($R^{7NB}$) is: —NMe$_2$.

15. The method of claim 1, wherein each of $HX^1$ and $HX^2$ is independently a monoprotic acid.

16. The method of claim 1, wherein each of $HX^1$ and $HX^2$ is independently a hydrohalide acid.

17. The method of claim 1, wherein $HX^1$ and $HX^2$ are each HCl.

18. The method of claim 1, wherein $HX^1$ and $HX^2$ are each HBr.

19. The method of claim 1, wherein each of $HX^1$ and $HX^2$ is an organic acid.

20. The method of claim 19 wherein each of $HX^1$ and $HX^2$ is independently selected from $H_2CO_3$ and $CH_3COOH$.

21. The method of claim 1, wherein:
each of $R^1$ and $R^9$ is —H;
each of $R^{3NA}$ and $R^{3NB}$ is -Me;
each of $R^{7NA}$ and $R^{7NB}$ is -Me;
each of $HX^1$ and $HX^2$ is independently a monoprotic acid.

22. The method of claim 1 wherein the cognitive or CNS disorder is a tauopathy and wherein the treatment of the tauopathy is such that the DAPTZ compound causes inhibition of the aggregation of the tau protein associated with said tauopathy and also dissolution of tau aggregates in the brain of the patient or subject.

23. The method of claim 22 wherein the cognitive or CNS disorder is selected from Alzheimer's disease, Pick's disease, Progressive supranuclear palsy (PSP), fronto-temporal dementia with parkinsonism linked to chromosome 17, disinhibition-dementia-parkinsonism-amyotrophy complex, pallido-ponto-nigral degeneration, Guam-ALS syndrome; pallido-nigro-luysian degeneration, cortico-basal degeneration; Down's syndrome; and postencephalitic parkinsonism; parkinsonism with dementia complex of Guam.

24. The method of claim 1 wherein the cognitive or CNS disorder is selected from:
CJD, nvCJD, fatal familial insomnia, Gerstmann-Straussler-Scheinker syndrome or Kuru where the protein is prion protein;
Huntington's disease where the protein is huntingtin;
Spinocerebellar ataxia 1, 2, 3, or 7 where the protein is ataxin 1, 2, 3 or 7;
Dentatorubropallidoluysian atrophy where the protein is atrophin;
Spinal and bulbar muscular atrophy where the protein is androgen receptor;
Familial encephalopathy with neuronal inclusion bodies where the protein is neuroserpin;
Hereditary cerebral angiopathy (Icelandic) where the protein is cystatin C; and
Amyotrophic lateral sclerosis where the protein is superoxide dismutase 1.

25. The method of claim 1 wherein the cognitive or CNS disorder is mild cognitive impairment.

26. The method of claim 1 wherein the cognitive or CNS disorder is a synucleinopathy, which is optionally Parkinson's Disease, dementia with Lewy bodies, multiple system atrophy, drug-induced parkinsonism, or pure autonomic failure (PAF).

27. The method of claim 1 wherein the patient also has a haematological disorder, the effects of which may otherwise be exacerbated by the DAPTZ compound.

28. The method of claim 27 wherein the haematological disorder is selected from a haemoglobinopathy, an anemia, a haematological malignancy, and a coagulopathy.

29. The method of claim 28 wherein:
   (i) the haemoglobinopathy is sickle-cell disease, thalassemia, or methaemoglobinemia;
   (ii) the anemia is a haemolytic anemia;
   (iii) the haematological malignancy is lymphoma, myeloma, plasmacytoma or leukemia; and
   (iv) the coagulopathy is hemophilia.

* * * * *

UNITED STATES PATENT AND TRADEMARK OFFICE
CERTIFICATE OF CORRECTION

PATENT NO. : 10,188,658 B2
APPLICATION NO. : 14/866035
DATED : January 29, 2019
INVENTOR(S) : Claude Michel Wischik et al.

Page 1 of 1

It is certified that error appears in the above-identified patent and that said Letters Patent is hereby corrected as shown below:

In the Claims

Column 93, Line 24, the portion reading - –H, $C_{2-4}$alkenyl, and halogenated $C_{1-4}$alkyl; - should read -- –H, $C_{1-4}$alkyl, $C_{2-4}$alkenyl, and halogenated $C_{1-4}$alkyl; --.

Column 93, Line 26, the portion reading - –H, $C_{2-4}$alkenyl, and halogenated $C_{1-4}$alkyl; - should read -- –H, $C_{1-4}$alkyl, $C_{2-4}$alkenyl, and halogenated $C_{1-4}$alkyl; --.

Signed and Sealed this
Ninth Day of April, 2019

Andrei Iancu
*Director of the United States Patent and Trademark Office*